US011566280B2

(12) United States Patent
Chatre et al.

(10) Patent No.: US 11,566,280 B2
(45) Date of Patent: Jan. 31, 2023

(54) METHOD, PROBE AND KIT FOR DNA IN SITU HYBRIDIZATION AND USE THEREOF

(71) Applicants: INSTITUT PASTEUR, Paris (FR); CENTRE NATIONAL DE LA RECHERCHE SCIENTIFIQUE, Paris (FR)

(72) Inventors: Laurent Arnaud Chatre, Vincennes (FR); Miria Ricchetti, Paris (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 343 days.

(21) Appl. No.: 15/965,681

(22) Filed: Apr. 27, 2018

(65) Prior Publication Data

US 2019/0330691 A1    Oct. 31, 2019

Related U.S. Application Data

(62) Division of application No. 14/005,364, filed as application No. PCT/EP2012/054739 on Mar. 16, 2012, now Pat. No. 9,957,555.

(30) Foreign Application Priority Data

Mar. 17, 2011   (EP) ..................................... 11290139

(51) Int. Cl.
*C12Q 1/6841* (2018.01)
*C12Q 1/6851* (2018.01)
*C12Q 1/6876* (2018.01)

(52) U.S. Cl.
CPC .......... *C12Q 1/6841* (2013.01); *C12Q 1/6851* (2013.01); *C12Q 1/6876* (2013.01); *C12Q 2563/107* (2013.01)

(58) Field of Classification Search
None
See application file for complete search history.

(56) References Cited

U.S. PATENT DOCUMENTS

| | | | | |
|---|---|---|---|---|
| 5,541,308 A * | 7/1996 | Hogan | ................. | C12Q 1/6811 536/23.1 |
| 6,462,190 B1 * | 10/2002 | Michikawa | .......... | C12Q 1/6876 435/252.3 |
| 2006/0057564 A1 * | 3/2006 | Wang | ................... | C12Q 1/6883 435/6.11 |

* cited by examiner

*Primary Examiner* — Katherine D Salmon
(74) *Attorney, Agent, or Firm* — Arrigo, Lee, Guttman & Mouta-Bellum LLP

(57) ABSTRACT

The invention relates to a method for the detection of the occurrence of initiation of replication events in genomic DNA in a eukaryotic cell, involving contacting said eukaryotic cell comprising said genomic DNA with a first nucleotide probe, under conditions enabling in situ hybridization of said first nucleotide probe with a target region in the DNA genome, wherein said target region comprises a nucleic acid sequence which has no identified corresponding annealing RNA in a metabolically active cell and therefore remains RNA-free during transcription and replication of said DNA genome and detecting said first nucleotide probe hybridized to said DNA. Further detection of at least one RNA molecule can be achieved. The invention also relates to a nucleic acid molecule suitable for use as a probe, hybridizing with a target region in a eukaryotic genomic DNA, and comprising a nucleic acid sequence which has no identified corresponding annealing RNA in the metabolically active cell containing said eukaryotic genomic DNA and therefore remains RNA-free during transcription and replication of said DNA genome. The invention also encompasses kit(s) for carrying out in situ hybridization and use of the method(s), nucleic acid molecule(s) or kit(s) of the invention in the detection of mitochondrial disease(s), neoplasic diseases(s) or cancer(s), or in the testing of the cytotoxicity of organic or chemical compounds, especially drugs, on eukaryotic cells.

4 Claims, 48 Drawing Sheets

Specification includes a Sequence Listing.

IMR-90 primary fibroblasts

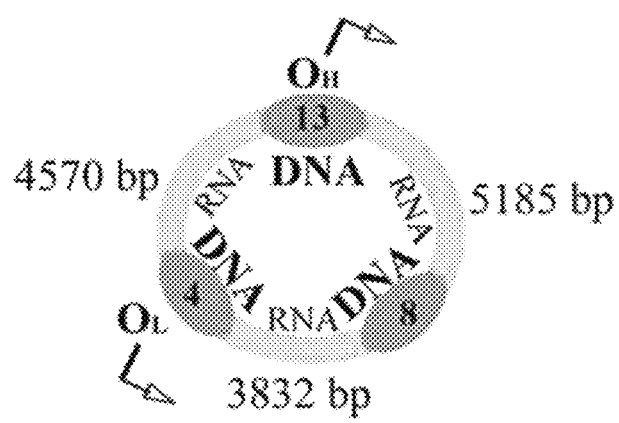
FIG. 3A
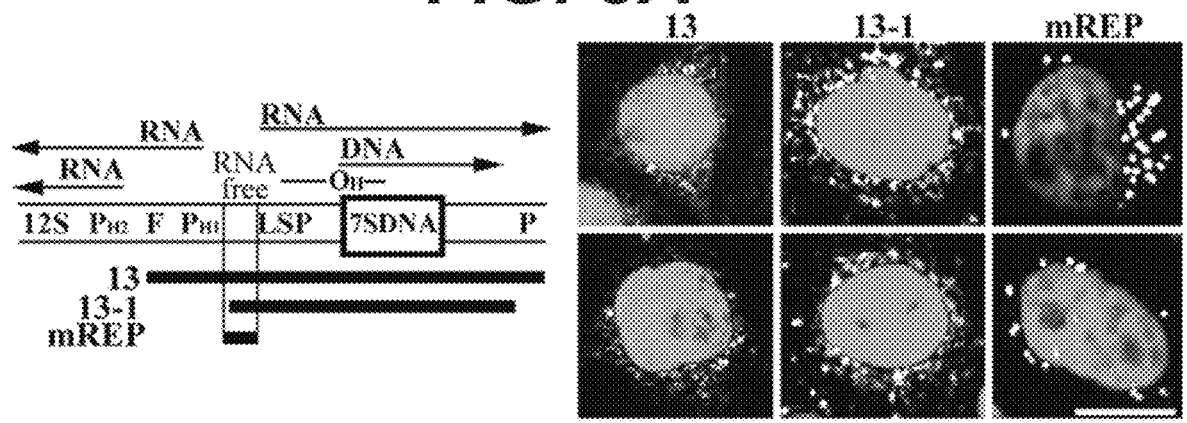
FIG. 3B
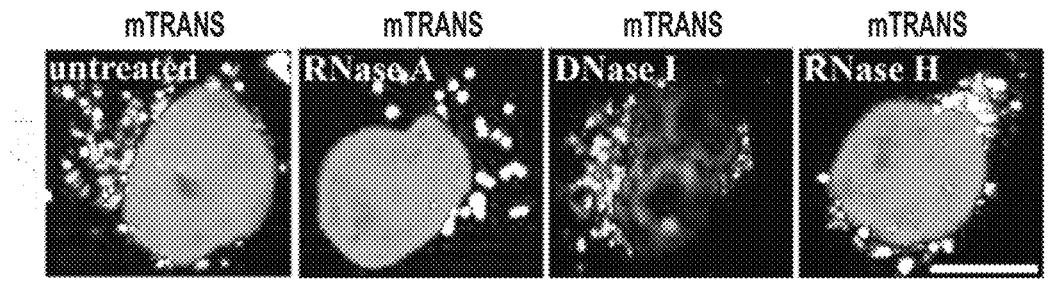
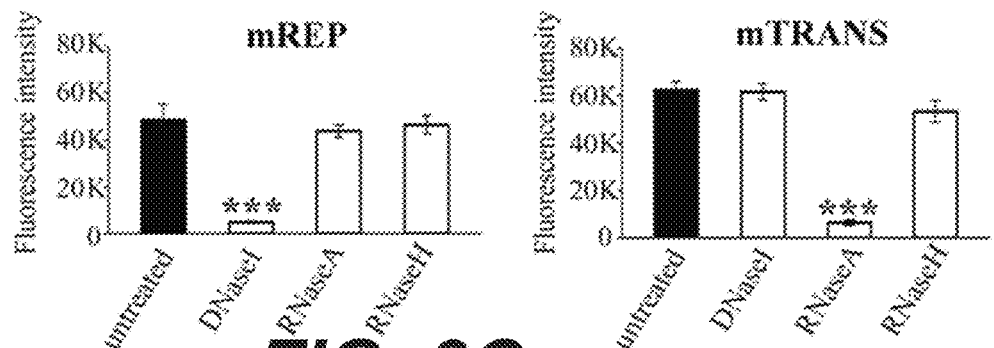
FIG. 3C mtDNA probe (1 to 14)
TOM22

| Probe | % of co-localization with | | |
|---|---|---|---|
| | 2 | 3 | 4 |
| 2 | - | 92.1 ± 1.4 | 22.6 ± 3.2 |
| 3 | 84.3 ± 1.9 | - | 26.8 ± 3.2 |
| 4 | 44.8 ± 3.0 | 50.5 ± 4.2 | - |

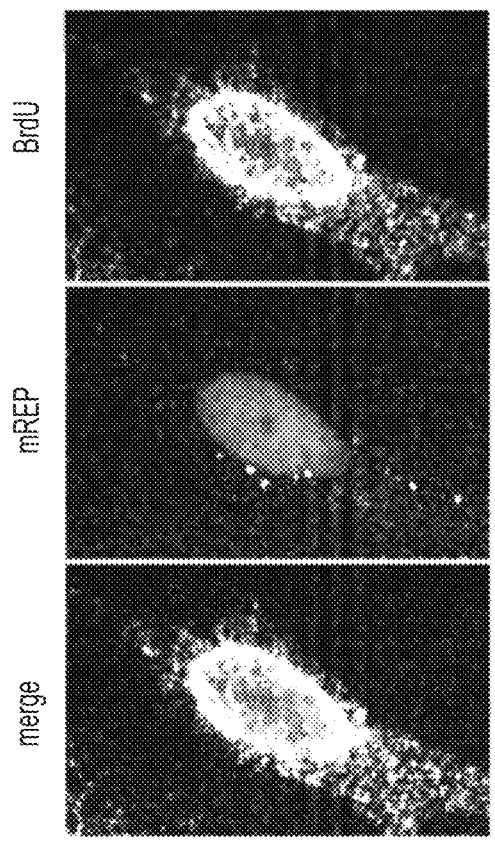
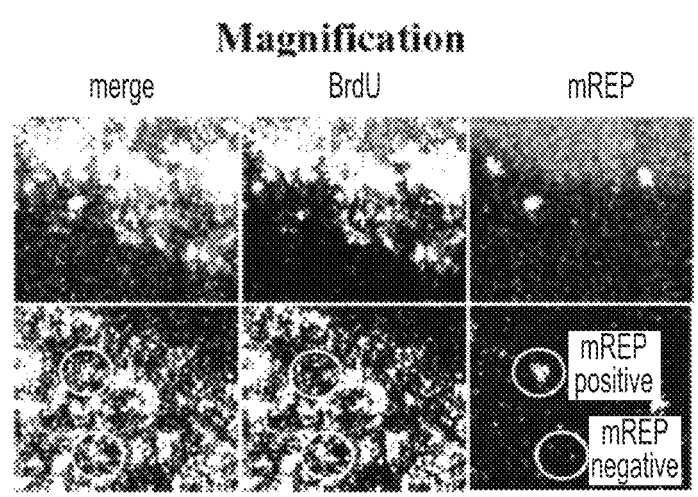
FIG. 12C

Human mREP sequence (99)

ACATTATTTTCCCCTCCCACTCCCATACTACTAATCTCATCAATACAACCCCGCCCATCCTAC
CCAGCACACACACCGCTGCTAACCCCATACCCC

FIG. 13A mREP - Human polymorphism - variations

ACATTATTTTCCCCTCCCACTCCCATACTACTAATCTCATCAATACAACCCCGCCCATCCTAC
CCAGCACACACACCGCTGCTAACCCCATACCC

FIG. 13B

-> Homo sapiens NC_012920.1

```
HsmREP    ACATTATTTTCCCCTCCCACTCCCATACTACTAATCTCATCAATACAACCCCGCCCATC
Hs        ACATTATTTTCCCCTCCCACTCCCATACTACTAATCTCATCAATACAACCCCGCCCATC
          ************************************************************

HsmREP    CTACCCAGCACACACACACCGCTGCTAACCCCATACCCC
Hs        CTACCCAGCACACACACACCGCTGCTAACCCCATACCCC
          ***************************************
```

-> Pan troglodytes NC_001643.1

```
HsmREP    ACATTATTTTCCCCTCCCACTCCCATACTACTAATCTCATCAATACAACCCC-GCCCAT
Pt        ACATGCCCTCCCCCCTCAACTCCCATTCTACTAGCCCCAGCAACGTAACCCCCTACTCAC
          ****  *  ****  * *******  *****   *  ** ***  *******  *  **

HsmREP    CCTACCCAGCACACACACACCGCTGCTAACCCCATACCCC
Pt        CCTACTCA--ACACATATACCGCTGCTAACCCCATACCCT
          *****  **   ***** * ********************
```

-> Pan paniscus NC_001644.1

```
HsmREP    ACATTATTTTCCCCTCCCACTCCCATACTACTAATCTCATCAATACAACCCC-GCCCAT
Panp      ACATGTCCTCCCCCCTCAACTCCCATTCCACTAGCCCCAACAACATAACCCCCTGCCCAC
          ****   *  *****   *******  * **** *  ** *** * *******  ****

HsmREP    CCTACCCAGCACACACACACCGCTGCTAACCCCATACCCC
Panp      CCCACTCAGCACATATAC--CGCTGCTAACCCTATACCCT
          **  ** ******* * **  *************  ******
```

FIG. 13C

-> Gorilla gorilla NC_001645.1

```
HsmREP    ACAT-TATTTTCCCTCCCACTCCCATACTACTA-----ATCTCATCAATACAACCCCCG
Gg        GTATGCACTTTTAACAGTCACCCCTCAACTAACATAGTCAGCCCACCAGTACAACCCCCG
          * **  * ***  **  ** * ***  ****  *    * **  ** * **********

HsmREP    CCCATCCTACCCAGCACACACACACCGCTGCTAACCCCATACCCC
Gg        CCCGCCCTA----GCA-ACACACACTGCTGCTGATCCTATACCCC
          *** * ****    *** ******** ***** * ** ******
```

-> Pongo pygmaeus NC_001646.1

```
HsmREP    ACAT-TATTTTCCCTCCCACTCCCATACTACTA-ATCTCATCAATA----CAACC--CC
Pp        ATGTGCACTTTCAACAGGCACCCCTCAACTAACACAACCCACTTTTAATTTCCACCTACC
          *  *   * ***  **  ***  ** *  ** *  * * **  *      * ***  **

HsmREP    CGCCCATCCTACCCAGCA----CACACACACCGCTGCTAACCCCATACCCC
Pp        AACCCATCCTGCCCTGCCTTCCCACAAACACCACTACTACCCCCACACCTC
          * *******   ** ***     ***** ***  ** **    *** ** *
```

-> Hybolates lar NC_002082.1

```
HsmREP    ACATT--ATTTTCCCTCCCACTCCCATACTACTAATCTCATCAATACAACCCCGCCCA
Hl        ACATTCCATATTCCAGCCGAGCATCCAATCCACTAAAGGTGCTAAT-TAATTCATGCTTG
          *****   **  ** **  *  * ****   * ***        *** *  * *  * *

HsmREP    TCCTACCCAGCACACACACACCGCTGCTAACCCCATACCCC
Hl        TTGGACATAGCAATAACCAACCAACG-TAACCCCAAACCAC
          *   ** * ****  **  *** ** * ** ********  ****
```

-> Cebus albifrons NC_002763.1

```
HsmREP    ACATTATTTTCCCCTCCCACTCCCATACTACTAATCTCATCAATACAACCCCCGCCCATC
Ca        GCATTTGGTTCCTACCTCAGGGCCATCTCACTAAGACCGTGTCCACGTTCCTCTTAAATA
          ****   ****  ***  *     ****   ****  *   *  ** *  *    **
```
```
HsmREP    CTACCCAGCACACACACACCGCTGCTAACCCCATACCCC
Ca        AGACATCACGATGGTGTGGCGCTATCACCCTCTTAACCG
          **  *         ****  * ** *  * *  **  *
```

-> Capra hircus NC_005044.2

```
HsmREP    ACATTATTTTCCCCTCCCAC-----TCC---CATACTACTAATCT-----CATCAATACA
Ch        ACACAAACTTCCCACTCCACAAGCTTACAGACATGCCAACAACCACACGTATAAAAACA
          *** *  * ***** ***** ****  * * * ** ***  *     *   **  ***

HsmREP    ACCCCGCCCATCCTACCCAGCACACACACACCGCTGCTAACCCCATACCCC
Ch        TCCCAATCCTAACCCAACTTAGATACCCACACAAACGCCAACACCACACAAT
          *** * * ** ****   ***  **   *** ***    **  *  **  **
```

FIG. 13C CONT.

-> Mus musculus NC_005089.1

```
HsmREP  ACATTATTTTCCCCTCCCACTCCCATACTACTAATCT-----CATCAATACAACCCCGC
Mm      ATATGACTATCCCCTTCCCCATTTGGTCTATTAATCTACCATCCTCCGTGAAACCAACAA
         *  * *   ******  **  **  *  *** ******   *  **  *   ***  *

HsmREP  CCATCCTACCCAGCACACACACACCGCTGCTAACCCCATACCCC
Mm      CCCGCCCACCAATGCCCTCTTCTCGCTCCGGGCCCATTAAACT
        **  * * ***  *   *   * * *** *    *** **  *
```

-> Oryctolagus cuniculus NC_001913.1

```
HsmREP  ACATTATTT--TCCCCTCCCACTCCCATACTACTAATCTCATCAATACAACCCCGCCCA
Oc      AGACCATCAAATCTACACACACCACTCAACTCTTACCCATACGACTATCCCTCTCCCCA
        *  *  *     **  ** ****  **  ***  **   **** * *      ****

HsmREP  TCCTACCCAGCACACACACACCGCTGCTAACCCCATACCCC
Oc      GTCCTCTCACAACTTACCATCCTCCGTGAAACCAACAACCC
         *  * **  *  *   ** **  **  * *  ** * ***
```

-> Canis lupus NC_008092.1

```
HsmREP  ACAT-TATTTTCCCCTCCCACTCCCATACTACTAATCTCATCAATACAACCCCGCCCAT
Cl      ACTTATACAAACCCCCCTTACCCCCGTAAACTCATGTCATCTATTATACACTTATTTAT
        * *  **  *  **** *  ***  *  * * **  *****  **  ***  * * **

HsmREP  CCTACCCAGCACACACACACCGCTGCTAACCCCATACCCC
Cl      GTCCGCCAAACCCCAAAAACAGGACTAAGTGCATACAAT
         *   *  * *  *  *  * *    ****  *****
```

-> Rattus sordidus NC_014871.1

```
HsmREP  ACATTA-TTTTCCCCTCCCACTCCCATACTACTAATCTCA-TCAATACAACCCCGCCCA
Rs      TCATAAACCTTTCTCTTCCATATGACTATCCCTGACCCAATTGGTCTATATTTCTACCA
         ***    **   ** * **   **  **  ** *   *    *  *   *  *  ***

HsmREP  TCCTACCCAGCACACACACACCGCT-GCTAACCCCATACCCC
Rs      TCCTCCGTGAAATCAACAACCCGCCCACTAGTCCCCCTCTCC
        **** *     *   ***  **  * ***  *  **   * *
```

-> Felis catus NC_001700.1

```
HsmREP  ACATTATTTTCCCCTCCCACTCCCA--TACTACTAATCTCATCAATACAACCCCGCCCA
Fc      ATACTAAATCATAACTCTGTTCGCAGTTATCTATAGATATACCGACCTGACTCTAATTCG
        *  ** *    *  **  *  *  **   **  **  *   *   *   ** **  * *

HsmREP  TCC-TACCCAGCA----CACACACCGCTGCTAACCCCATACCCC
Fc      TCCCTATCGAACAACATTTTACATGTCTACGTTAGCCCACATCCC
        ***  **  * ***    *  **   *    **  ** *** *** 
```

FIG. 13C CONT.

-> Castor canadensis NC_015108.1

```
HsmREP    ACATTATTTTCCCCTCCCACTC-CCATACTACTAAT--CTCATCAATACAACCCCGCCC
Cc        ACAGTCTCTTAATCTACCATCCTCCGTGAAACCAGCAACCCGCTCGGGGAATGTCCCCTC
          ***  *  **    **  ***   *  **  *      **  *    **    **  *  *

HsmREP    ATCCTACCCAGCACACACACACCGCTGCTAACCCCATACCCC
Cc        TTCTCGCTCCGGGCCCATACAACTTGGGGTTCTATTCTGA
          **    *   *    *  **  ***  *      *    *  **  *
```

-> Gallus gallus NC_001323.1

```
HsmREP    ACATTATTTTCCCCTCCCACTCCCATACTACTAATCTCATCAATACAACCCCGCCCATC
Ggal      CCATTCTTTCCCCCTACACCCCTCGCCCTACTTGCCT--TCCACCGTACCTCTGGTTCCT
          *** *** *****  *    *     *    ****    **    **     *** *  *

HsmREP    CTACCCAGCACA---CACACACCGCTGCTAACCCCATACCCC
Ggal      CGGTCAGGCACATCCATGCATAACTCCTGAACTTTCTCACT
          *     *****      **    **   **  **  *  *        *  *
```

-> Danio rerio NC_002333.2

```
HsmREP    ACATTATTTTCCCCTCCCACTCCCATACTACTAATCTCATCAATACAACCCCGCCCATC
Dr        ACTATATATTATTATCTCCCCTTTTGGTA-TACGCGACAA-ACCCCTTACCCCCTT
          **  ***  **      **  *  *     *  **  **  *   *  *** **   **    *** *

HsmREP    CTACCCAGCACACACA--CACCGCTGCTAACCCCATACCCC
Dr        ACGTCCAGCGATTCCTGTTATCCTTGTCAAACCCCTAAACC
          * **** *       *   *  *   **  **  **  **    **
```

FIG. 13C CONT.

| PL-OH | 7S | large foci |
|---|---|---|
| RNA/DNA | RNA | prevalent pattern (1) |
| - | RNA a/o RNA/DNA | pattern (2) |
| DNA | RNA a/o RNA/DNA | pattern (3) |
| DNA a/o RNA/DNA | RNA/DNA | pattern (4) |
| DNA a/o RHR-RNA/DNA | RNA a/o RHR-RNA/DNA | pattern (5) |
| - | DNA | pattern (6) |

*FIG. 15D*

| Probe | forward primer | reverse primer | reference |
|---|---|---|---|
| RT-qPCR primers | | | |
| TBP | CTTCACAGGTCAAAGGTTTAC | GCTGAGGTTGCAGGAATTGA | Marey et al. 2005. FEBS Journal 272(2) |
| 12S (1) | CTGCTCGCCAGAACACTACG | TGAGCAAGAGGTGGTGAGGT | Suissa et al. 2009. PLoS Genetics 5(5):e1000474 |
| 12S (2) | AAACTGCTCGCCAGAACACT | CATGGGCTACACCTTGACCT | Ishumm et al. 2010. NAR 38(16) |
| 16S (1) | GTATGAATGGCTCCACGAGG | GGTCTTCTCGTCTTGCTGTG | Suissa et al. 2009. PLoS Genetics 5(5):e1000474 |
| 16S (2) | GCTAAACCTAGCCCCAAACC | TTGGCTCTCCTTGCAAAGTT | Ishumm et al. 2010. NAR 38(16) |
| ND1 | TGGCCAACCTCCTACTCCTC | ATGGCGTCAGCGAAGGGTTG | Suissa et al. 2009. PLoS Genetics 5(5):e1000474 |
| ND2 | ACTGCGCTAAGCTCGCACTG | ATTATGATGCGGTTGCTTG | Suissa et al. 2009. PLoS Genetics 5(5):e1000474 |
| COI | ACCCTAGACCAAACCTACGC | TAGCCGAGAAAGTGTTGTTG | Suissa et al. 2009. PLoS Genetics 5(5):e1000474 |
| COII | ACAGATGCAATTCCCGGACG | GCTATGAAACTGTGGTTTGC | Suissa et al. 2009. PLoS Genetics 5(5):e1000474 |
| ATP8 | ATGCCCCAACTAAATACT | TTGTGGGGCAATGAATG | Uchiumi et al. 2010. NAR 38(16) |
| ATP6 | CCCACTTCTTACCACAAGCC | GTAGGTGCCTGCAGTAATG | Suissa et al. 2009. PLoS Genetics 5(5):e1000474 |
| COIII | ACTTCCACTCCATAAAGCTC | TGGCCTTGGTATGTGCTTTC | Suissa et al. 2009. PLoS Genetics 5(5):e1000474 |
| ND3 | CTACCATGAGCCCTACAAAC | ACTCATAGGCCAGAGTTAGG | Suissa et al. 2009. PLoS Genetics 5(5):e1000474 |
| ND4L | TATCGCTCACACCTCATATC | AGGCGGCAAAGACTAGTATG | Suissa et al. 2009. PLoS Genetics 5(5):e1000474 |
| ND4 | ACAAGCTCCATCTGCCTACG | TTATGAGAATGACTGCCGTG | Suissa et al. 2009. PLoS Genetics 5(5):e1000474 |
| ND5 | GGTTTCATCCTCGCCTTAGC | ACCTAATTGGGCTGATTTGC | Suissa et al. 2009. PLoS Genetics 5(5):e1000474 |
| CYTB | CTCCGTGAGGCCAAATATC | GAATCGTGTGAGGGTGGGAC | Suissa et al. 2009. PLoS Genetics 5(5):e1000474 |
| ND6 | ATTGGTGCTGTGGGTGAAAG | GGATCCTCCGAATCAACCC | Suissa et al. 2009. PLoS Genetics 5(5):e1000474 |
| NRF1 | GGATGATGCCGCACAGAA | CGCTGTTAAGCGCCATAGTG | Scarpulla et al. 2003. Biochem Biophys Res Com 110/3 |
| POLG | GAGAAGGCCCAGCAGATGTA | ATCCGACAGCCGATACCA | Setzer et al. 2008. Am J Pathol. 172(1) |
| TFAM | GACTTCTGCCAGCATAATAC | GAGTTCTGCTTGCTTTTATG | Freyssenet et al. 2006. Acta Biochim Pol. 53(3) |
| qPCR primers | | | |
| Probe | forward primer | reverse primer | reference |
| 18S | GAGAAACGGCTACCACATCC | GCTCGGAAGACTTCTGTAT | Suissa et al. 2009. PLoS Genetics 5(5):e1000474 |
| 12S | GCTCGCCAGAACACTACGAG | CAGGGTTGCTGAAGATGGC | Parone et al. 2008. PLoS One 3(9):e3257 |
| A | GTGGCTTTGGAGTTGCAGTT | | |
| B1 | | CAGCACCACCATGAATGTAC | Antes et al. 2011. NAR 38(19):6466-6476 |
| B2 | | GAAGCAGATTTGGTACCAC | Antes et al. 2011. NAR 38(19):6466-6476 |

*FIG. 23*

METHOD, PROBE AND KIT FOR DNA IN SITU HYBRIDIZATION AND USE THEREOF

The invention is directed to a method for analyzing events associated with replication in the genomic DNA in a eukaryotic cell, especially a mammalian cell, using in situ hybridization techniques. The method of the invention is especially directed to the detection of the occurrence of initiation of replication events in genomic DNA. In a particular embodiment, the invention also enables the co-detection of DNA and RNA molecules in a single cell. According to a further particular embodiment, the invention enables the co-detection and co-visualisation of DNA and optionally RNA and protein(s) in a single cell.

In the context of the invention, a genomic DNA molecule is a nucleic acid molecule that belongs to the genome of a cell, and replicates, especially in an autonomous or independent manner, in particular under the control of cellular regulatory elements, in metabolically active cell(s), and whose replication can therefore be observed in situ. The genome of a cell is considered to be the DNA of an organism, that carries all the information for all the proteins the organism will ever synthesize, and more generally the genome contains all the information necessary for the survival of a cell. Genomic DNA can be chromosomal DNA or plasmidic DNA, with the proviso that said plasmidic DNA belongs to the genome of a cell, as defined herein. More particularly in the context of the invention, genomic DNA (gDNA) molecule(s) is either mitochondrial gDNA or nuclear gDNA or both. A plasmid is a DNA molecule that is separate from, and can replicate independently of, the chromosomal DNA. Plasmids are double stranded and, in many cases, in particular in most cases, circular. Plasmids usually occur naturally in bacteria, but are sometimes found in eukaryotic organisms. By contrast, plasmidic DNA not belonging to a genome as functionally defined is not considered to be genomic DNA in the context of the present invention.

The invention also relates to specific probes, in particular nucleotide probes, which are particularly devised for the detection of the occurrence of initiation of replication events in genomic DNA in a eukaryotic cell. The invention encompasses means useful for detecting the occurrence of initiation of replication events in genomic DNA, in particular kits comprising such probes and processes for carrying out the invention.

According to particular embodiments, the methods, probes and kits of the invention are suitable for analyzing initiation of replication of genomic DNA at the single cell level, and therefore provide means for detecting impaired replication of gDNA, and in particular means useful for detecting diseases associated with such impairment, including mitochondrial disease(s), neoplasic diseases(s) or cancer(s).

In a particular embodiment, the invention especially relies on the results obtained in experiments designed to observe the occurrence of initiation of replication events in mitochondrial genomic DNA in human cells.

Indeed, mitochondrial DNA (mtDNA) replication and transcription are crucial for cell function, but these processes are poorly understood at the single-cell level. Tools currently offered to biologists do not permit the specific detection of mitochondria engaged in initiation of DNA replication. With respect to nuclear gDNA, tools currently offered to biologists do not permit the detection of nuclear gDNA engaged in initiation of its replication within a cell, i.e. at the single cell level, not isolated from its cellular context.

Mitochondria are ATP-producing organelles whose function is directed not only by the nuclear genome but also by their own genome. Each mitochondrion carries several copies of a genomic DNA, i.e. a circular double-stranded DNA that is replicated and transcribed autonomously in the organelle. Mitochondrial DNA (mtDNA) is arranged in nucleoprotein complexes, nucleoids, that include factors involved in replication and transcription as well as structural proteins required for mitochondrial maintenance (Chen and Butow 2005; Spelbrink 2010). These proteins include DNA polymerase γ (Polγ, the enzyme responsible for replication of mtDNA, and TFAM (also known as mtTFA), a protein implicated both in transcription of and in binding to the mtDNA, and whose levels are correlated with those of mtDNA (Poulton et al. 1994; Falkenberg et al. 2007; Shutt et al. 2010). Human mtDNA, a 16.5 kbp molecule, is organized in 13 protein-coding, 2 rRNA, and 22 tRNAs genes that are transcribed from the (heavy) H-strand (12 mRNA, 2 rRNA and 14 tRNAs) and from the (light) L-strand (1 mRNA for ND6 gene, and 8 tRNAs) with production of polycistronic precursor RNAs. These primary transcripts are processed to produce the individual mRNA, rRNA and tRNA molecules[1]. The prevalent view of mtDNA replication is that DNA synthesis starts from origin $O_H$ where the nascent H strand frequently terminates 700 bp downstream giving rise to the 7S DNA, which produces a characteristic triple stranded structure, the D-loop[2,3]. When leading strand synthesis has reached two thirds of the genome, it exposes another major origin, the origin of L-strand DNA replication ($O_L$), and lagging-strand DNA synthesis then initiates in the opposite direction. Conversely, coupled leading and lagging strand synthesis has been described in a reduced number of molecules[4], suggesting that this model is not fully elucidated. Mitochondria display a variety of shapes ranging from highly interconnected tubular structures to individual small spherical units. These structures are highly dynamic and can be regulated by mitochondrial fusion and fission, and they vary during cell growth (Chan 2006; Lee et al. 2007; Mitra et al. 2009). Whether these different structures are related to mtDNA processing needs clarification.

Nuclear DNA (nDNA) is generally compacted in chromosome(s), and its replication generally begins at specific location(s) in the genome, called "origin(s)" or "replication origin(s)", which is/are the positions at which the DNA helix is first opened, giving rise to a "replication bubble". Unwinding of DNA at the origin, and synthesis of new strands, forms a replication fork, which has an asymmetric structure. The DNA daughter strand that is synthesized continuously is known as the leading strand, whose synthesis slightly precedes the synthesis of the daughter strand that is synthesized discontinuously, known as the lagging strand. Eukaryotic chromosomes generally contain multiple origins of replication. The different replication origins in eukaryotic chromosomes can be activated in a sequence, determined in part by the structure of the chromatin, with the most condensed regions of chromatin beginning their replication last.

The processing of mitochondrial DNA has been intensively analysed with biochemical approaches (reviewed in[5,6]), which essentially examined global cellular and mitochondrial populations, but little is known about mitochondrial activity at the single cell level, or about DNA and RNA at the single cell level. Thus, several questions on the dynamics and the regulation of mtDNA transcription and replication inside the same cell remain unresolved, as well as their implication in cellular fonction. To date, studies on mtDNA replication are widely based on molecular biology (2D-Gel of replication intermediates and in vitro assays). Currently available fluorescence in situ hybridization (FISH) tools, including recent improvements[7], do not identify mitochondria engaged in DNA replication, and they do not discriminate the transcription profiles of organelles in single cells. If a technique allowing to detect one mitochondrial transcript at a time has been disclosed[30], it required a genetically engineered step and was shown for the transcript ND6 only.

Moreover, although sequential RNA and DNA labelling[8], as well as labelling of either RNA or DNA, and proteins[9,10] have been performed, the techniques used, namely immunofluorescence and Fluorescent In Situ Hybridization (FISH), did not permit to simultaneously detect proteins and mitochondrial DNA and RNA (triple detection). Consequently, available techniques do not render possible a powerful and directly exploitable observation of the course of events occurring during gDNA, especially mtDNA, transcription and replication, especially when different molecular subpopulations, such as DNA, RNA or even proteins, are involved.

Therefore, the present invention addresses the need to obtain an outstanding tool for studying DNA replication, allowing a deeper comprehension of the events associated with DNA replication, and including the comprehension of the coordination of these events with other events such as RNA transcription and even protein(s) distribution in cell(s) or tissue(s) by tracking and monitoring these distinct molecular subpopulations in a concomitant or even simultaneous manner. Consequently, the invention proposes a new way to further explore the complex cellular dynamics and to use such exploration in detection of pathological states.

According to a particular embodiment of the present invention novel information can be provided on the dynamics of gDNA, especially mitochondrial gDNA, processing during physiological and pathological processes. These findings have implications in diagnostic tools of diseases, especially mitochondrial diseases or diseases associated with mitochondrial dysfunction(s) or impairment, in particular those where mtDNA depletion and mtDNA loss can be observed.

Indeed, defects in the mitochondrial replication machinery can lead to loss of genetic information by deletion and/or depletion of the mitochondrial (mt) DNA, which subsequently may cause disturbed oxidative phosphorylation and neuromuscular symptoms in patients. mtDNA depletion can originate from genetic defects, or be acquired, i.e by clinical treatments, as for prolonged administration of anti-HIV nucleoside analogues. qPCR analysis on mtDNA is currently used to detect alterations of the mtDNA content in a given cell population. By permitting the monitoring of the occurrence of initiation of replication events in mitochondrial genomic DNA, and for example by measuring these events and following their evolution during the progression of disease, the present invention provides for the determination of such an impaired or abolished function. Consequently, detecting the initiation of DNA replication events and optionally combining this detection with the detection of other signals, therefore determining the state of mtDNA at the single cell level, enables the emergence of a more powerful research and diagnostic tool.

To this end, the invention relates to a method for the detection of the occurrence of initiation of replication events in genomic DNA in a eukaryotic cell, comprising the steps of:
contacting said eukaryotic cell comprising said genomic DNA with a first nucleotide probe under conditions enabling in situ hybridization of said first nucleotide probe with a target region in the DNA genome, wherein said target region comprises a nucleic acid sequence which has no identified corresponding annealing RNA in a metabolically active cell and therefore remains RNA-free during transcription and replication of said DNA genome and,
detecting said first nucleotide probe hybridized to said DNA.

According to a particular embodiment, the target region or the nucleic acid sequence of the target region that has an ability to remain RNA-free, is located in a naturally transiently open structure of two complementary single strands of gDNA in a metabolically active cell.

The methods and uses according to the invention are performed in vitro on samples of biological material.

According to a particular embodiment, the expression "the target region in the DNA genome that comprises a nucleic acid sequence which has no identified corresponding annealing RNA in a metabolically active cell remains RNA-free during transcription and replication of said DNA genome" encompasses the case wherein said nucleic acid sequence remains substantially RNA-free during transcription and replication of said DNA genome, meaning that the amounts of RNA transcripts that would be found annealed to said nucleic acid sequence remain below the detection level in experimental conditions of detection of hybridization according to the invention, in particular they do not influence the experiments conducted herein, i.e. their signals do not exceed background levels or noise.

Especially, it is indicated that the amounts of such transcripts would not be sufficient to allow their detection after treatment with DNAse, in particular DNAseI according to the invention. These amounts would represent minor amounts with respect to the whole amount of transcripts.

In the context of the invention, a "target region" in the DNA genome is a genomic DNA region comprising a nucleic acid sequence which has no identified corresponding annealing RNA in the metabolically active cell under assay and therefore remains RNA-free during transcription and replication of the DNA genome to which the nucleic acid sequence belongs.

In other words, a target region is a genomic DNA region comprising a sequence domain that has ability to remain RNA free, in particular RNA-transcript(s) free, during the transcription and replication of the DNA genome to which it belongs (mtDNA or nDNA) in the cell that is tested.

According to a specific embodiment, the target region of said first probe consists of a nucleic acid region in a genomic DNA which has no identified corresponding annealing RNA in a metabolically active cell.

In a particular embodiment, the target region of said first probe encompasses said RNA-free domain but is longer than said domain, including substantially longer, as illustrated hereafter.

According to a particular embodiment, such a naturally transiently open structure can be a replication bubble originating around the locus of a replication origin. According to a particular embodiment, such a naturally transiently open structure is the so-called DNA encompassed by the D-loop region of the mitochondrial genome, which is located between coordinates 16024 to 576 in the human mitochondrial genome (NCBI or Genbank or MITOMAP sequence reference NC_012920.1). According to a particular embodiment, the sequence of the target region that has an ability to remain RNA-free, is located proximal to, or includes, or overlaps known origin(s) of replication, in particular a mitochondrial origin of replication, or one of its ends is within a distance of less than 10 nucleotides, in particular 1, 2, 3, 4, 5, 6, 7, 8, 9, especially 6 nucleotides, from a known origin of replication, in particular a mitochondrial origin of replication. In particular in human mtDNA, such an origin of replication can be the $O_H$ origin of replication, located between coordinates 110 to 441 of the mitochondrial genome (NCBI or Genbank or MITOMAP sequence reference NC_012920.1).

According to a particular embodiment said target region or said nucleic acid sequence of the target region encompasses nucleotides within a distance of less than 10, in particular 1, 2, 3, 4, 5, 6, 7, 8 or 9 nucleotides upstream or downstream from a naturally transiently open structure of two complementary single strands of gDNA in a metabolically active cell.

In the context of the invention, "hybridization" relates to the fact of obtaining a close interaction of the nucleotide probe and the target region that is expected to be revealed by the detection of the nucleotide probe. Such an interaction can be achieved by the formation of hydrogen bonds between the nucleotide probe and the target sequence, which is typical of the interactions between complementary nucleotide molecules capable of base pairing. Hydrogen bonds can be found, for example, in the annealing of two complementary strands of DNA.

Within the context of the invention, hybridization conditions encompass contacting the nucleotide probe with the target region during about 15 hours at 37° C. in a conventional buffer such as illustrated in the examples, e.g. an hybridization buffer with 50% formamide, 10% dextran sulphate, in 2×SSC pH 7.0 or another similar buffer as appropriate. Hybridization conditions can further involve a step of washing the cell contacted with the nucleotide probe(s) with an appropriate, conventional, buffer prior to the detection step, such as illustrated in the examples.

For example, washing can be performed several times for 2-5 min in 2×SSC buffer at room temperature, then several times in 1×SSC buffer at room temperature, then several times in 0.1×SSC buffer at room temperature. Finally, an ultimate washing can be performed several times in PBS 1× buffer at room temperature.

The nucleic acid sequence of the probe should be at least partly complementary to the sequence of the target region of the genomic DNA, i.e. should be complementary over a region sufficient to enable stable base pairing.

Typically, a first nucleotide probe designed for hybridizing to a target region of genomic DNA is a labelled nucleic sequence fragment complementary to the target region of the genomic DNA and having substantially or in particular exactly, the same length as said target.

In a particular embodiment, the first nucleotide probe designed for hybridizing to a target region of genomic DNA is a labelled nucleic sequence fragment complementary to the targeted DNA fragment and having substantially, or in particular exactly, the same length as the nucleic acid sequence which has no identified corresponding annealing RNA in a metabolically active cell and therefore remains RNA-free during transcription and replication of said DNA genome.

In a particular embodiment, a first nucleotide probe designed for hybridizing to a target region of genomic DNA is a labelled nucleic sequence fragment comprising a nucleic acid sequence that is complementary to the targeted DNA fragment, said nucleic acid sequence having substantially, or in particular exactly, the same length than the nucleic acid sequence which has no identified corresponding annealing RNA in a metabolically active cell and therefore remains RNA-free during transcription and replication of said DNA genome.

However, according to other embodiments, the interaction of the nucleotide probe and the target region can also involve van der Waals interactions, ionic bonds or covalent linkages. Such interaction(s) might imply that the nucleotide probe contains modified nucleotides or bear specific moieties generally not present in nucleotidic molecules.

"In situ hybridization" refers to the fact that the hybridization is carried out on the assayed biological material. Said biological material can be single cell(s) or tissue(s), or a sample comprising the same. Preferably, the integrity of the structure and/or content of the biological material is maintained. Therefore, in order to achieve the invention, the biological material is preferably fixed.

Accordingly, in a preferred embodiment, the method of the invention is carried out on fixed cell(s) or tissue(s).

In a particular embodiment, the method of the invention further permits to maintain the integrity of the cell(s) volume and thus the analysis of fixed sample(s) in three-dimension.

According to a particular embodiment, the cell(s) or tissue(s) are eukaryotic cell(s) or tissue(s), in particular human cell(s) or tissue(s). For illustration cell(s) or tissue(s) derived from human cell lines such as HeLa, HCT116, HT29, AGS cell lines, and/or human primary cells, i.e. IMR-90, BJ human fibroblasts obtained from ATCC, are used.

In a particular embodiment, the genomic DNA is mitochondrial gDNA.

In another particular embodiment, the genomic DNA is nuclear gDNA.

In another particular embodiment, the genomic DNA is both nuclear gDNA and mitochondrial gDNA. In such an embodiment, the expression "genomic DNA" refers to a group of genomic DNA molecules, i.e. refers to more than one genomic DNA molecule, said group of genomic DNA molecules consisting of more than one copy of genomic DNA molecules (as found in a single mitochondrion) and/or more than one genomic DNA molecules that are different from each other (such as mitochondrial gDNA and nuclear gDNA).

According to the invention, a "probe" is aimed at revealing the target region of interest, and is therefore generally, but non-exclusively, labelled. Labelling of the probe aimed at revealing the target region in the DNA genome is preferably achieved with either radio- or antibody-discoverable- or fluorescent- or biotinylated-tags or quantum dots, especially fluorescent quantum dots. Said tags or quantum dots are directly or indirectly associated, including coupled, to the probe. Depending upon the type of labelling, the probe can be localized or visualized or measured on the biological material after hybridization with its target using appropriate techniques, such as autoradiography or fluorescence microscopy. An example of discoverable tag is digoxigenin, biotin, or hapten for example revealed by a labelled antibody or a labelled reagent, such as a fluorescent antibody raised against digoxigenin or a labelled biotin binding molecule such as avidin or streptavidin.

According to a specific embodiment, the probe is rendered discoverable, especially through fluorescence detection methods, by introducing an antigen in said probe or by coupling said probe with an antigen that will be further revealed by a secondary anti-antigen antibody, especially a fluorescent anti-antigen antibody. One advantage of using antibodies might be an increase of the intensity of the resulting fluorescent signal.

In a particular embodiment, probe(s) are directly labelled with fluorescent moieties (tags). One advantage of such an embodiment might be to bypass the use of an antibody for the detection of the probe in order, for example, to increase the specificity or the practicability of the labelling/detection method.

Probe(s) is/are preferably nucleotide probe(s), and are especially short sequences of single stranded DNA capable of base pairing with their complementary DNAs. The invention encompasses probe(s) containing nucleotide(s) coupled or linked to other molecule(s) or moiety(ies).

According to a particular embodiment probe(s) is/are DNA probe(s) such as PCR product(s) or DNA fragment(s), including plasmidic probe(s) or probe(s) comprising such elements.

According to a particular embodiment, they can be double-stranded DNA probes that require being denaturated as single stands prior to their use.

According to a particular embodiment, the nucleotide probe contains, among its nucleotides, one or more modified nucleotides or nucleotides bearing specific moieties generally not present in nucleotidic molecules. Locked Nucleic Acids (LNA) are modified nucleotides and a class of RNA analogs that have an exceptionally high affinity towards complementary DNA and RNA. They can substitute natural nucleotides in DNA probes.

In a particular embodiment of the invention, the term "probe" encompasses more than one molecular entities used together to reveal the target region.

In such a particular embodiment, the target region can be fragmented along the considered genomic DNA. For example, a target region of the DNA genome can be spread among more than one location on a single genomic DNA molecule or on more than one genomic molecule.

According to a particular embodiment, the method of the invention is characterised in that the first nucleotide probe consists of at least two subsets of probes, wherein at least one subset hybridizes with a target region in the DNA genome that comprises a nucleic acid sequence which has no identified corresponding annealing RNA in a metabolically active cell and therefore remains RNA-free during transcription and replication of said DNA genome.

In a specific embodiment, one of said subsets of probes contains nucleic acid molecules comprising, or consisting of, or being fragments of, or having at least 80% identity with, SEQ ID NO:17.

According to another embodiment the first probe of the invention is longer than the sequence complementary to the RNA-free domain and especially comprises a sequence hybridizing to mtDNA that is transcribed in a metabolically active cell.

By "occurrence" it is meant that the method of the invention enables to qualitatively detect initiation of the replication of genomic DNA and, according to a particular embodiment, to quantitatively detect such initiation event(s) of the replication process.

"Initiation of replication events" can be, for example, the formation of replication bubble(s) on the analyzed genomic DNA, or in a particular embodiment where the mitochondrial gDNA is assayed for initiation of replication, the formation of a D-loop structure, including the formation of three-stranded D-loop structure. Such events may precede the entire replication of the analyzed gDNA, meaning that such events may precede replication over the complete analyzed gDNA. Such events may alternatively be followed by interrupted synthesis of the nascent strand of DNA.

In a cell, DNA replication usually begins at specific location(s) in the genome, called "origin(s)" or "replication origin(s)". Once polymerases have opened the double stranded genomic DNA molecule, an area known as a "replication bubble" forms (usually initiated at a certain set of nucleotides, the origin of replication).

With respect to particular embodiments aimed at detecting the occurrence of initiation of replication events in mitochondrial genomic DNA, it is knowledgeable to consider that, in Mammalian, Avian, Fish, or Plant cells, the initiation of mitochondrial genome replication generally occurs in a particular region named "control region" or "D-Loop" or "displacement loop". When the mtDNA initiation of replication starts, the D-Loop region is opened, and the corresponding DNA locally results in single strands that serve as template for the synthesis of new mtDNA. This transitory opened D-Loop region may present a triplex-DNA structure, said structure being however located in a naturally transiently open structure of two complementary single strands of gDNA. The presence of D-loop region is typical of the human and other mt DNAs, such as Mammalian, Avian, Fish or Plant mtDNAs. The coordinates of said D-loop regions vary according to the considered organisms but can be found in the literature[31]. However D-Loop regions are not found in all mtDNA.

In particular in human cells, the D-loop region is roughly located between the coordinates 16024 and 576 of the L-strand on the mitochondrial genome (according to the data released to date on databases, in particular under accession number NC_012920.1 (NCBI, GenBank or MITOMAP sequence reference), see in particular MITOMAP: http://www.mitomap.org/MITOMAP/HumanMitoSeq).

In a particular embodiment, the target region or the RNA-free nucleic acid sequence comprised in said target region is located in a naturally transiently open structure of two complementary single strands of gDNA in a metabolically active cell, as disclosed above and in the following embodiments.

According to a particular embodiment, the target region or the RNA-free nucleic acid sequence comprised in said target region is located upstream from the major H-strand promoter on the mitochondrial genome (PH1), which coordinates are given in Table 2 (coordinates and direction are given herein with respect to the L-strand of the mtDNA). However, in the context of the invention, the target region or the RNA-free nucleic acid sequence comprised in said target region encompasses the sequences found on either the L-strand or the H strand at the specific location mentioned herein. Reference is made to the L-strand to indicate the position of the major H-strand promoter only.

According to a particular embodiment, especially when probe(s) are synthesized or obtained as a result of a PCR amplification, probe(s) is/are double-stranded DNA probe(s). They are denaturated as single stands prior to their use. When used simultaneously after denaturation, such a mix of complementary single-stranded probe(s) results in annealing both the L and H strands of the target region of a mtDNA.

In a particular embodiment, the target region or the RNA-free nucleic acid sequence comprised in said target region is located downstream from the L-strand promoter on the mitochondrial genome (LP or LSP), which coordinates are given in Table 2 (coordinates and direction are given herein with respect to the L-strand of the mtDNA). However, in the context of the invention, the target region or the RNA-free nucleic acid sequence comprised in said target region encompasses the sequences found on either the L-strand or the H strand at the specific location mentioned herein. Reference is made to the L-strand to indicate the position of the L-strand promoter only.

By "naturally transiently open structure of two complementary single strands of gDNA" it is meant a gDNA structure formed by the dissociation of the two DNA strands constituting the gDNA as a result of processing by replication machinery and mechanism(s) inherent to a metabolically active cell, during its life cycle.

More specifically, it will be understood that the target region is located near or in a region of the genomic DNA that is involved in the early events of the replication of said genomic DNA, such as a region found in a replication bubble or a region at least partly encompassed by a replication bubble. Such a region will generally be localized in the vicinity of a replication origin of a genomic DNA of an eukaryotic cell, in particular in the close vicinity or near, i.e. no farther than 10 nucleotides from a replication origin of a genomic DNA of an eukaryotic cell.

According to a particular embodiment, the target region is located in the vicinity of a replication bubble or at a locus encompassed by a replication bubble (where a replication bubble can be found), in particular no farther than 10 nucleotides from such a bubble or locus encompassed by such a bubble. Replication bubbles initiate at the locus of replication origins.

According to a specific embodiment, the target region is located at 5 nucleotides of the $O_H$ replication origin in the human mtDNA.

A nucleic acid sequence having "no identified corresponding annealing RNA in a metabolically active cell" is a sequence having no strictly corresponding, i.e. complementary or matching, RNA, especially no RNA transcript(s) resulting from the transcription process occurring naturally in the living eukaryotic cell under assay in the detection conditions disclosed herein. By "corresponding" it is understood a substantial, in particular a strict, complementarity of nucleic acid sequences which are aligned and whose similarity is calculated over the entire length of the aligned sequence by alignment algorithm such as the Needelman and Wunsch algorithm (a substantial similarity or perfect match is expected). Therefore such a nucleic acid sequence has an ability to remain RNA-free, in particular RNA-transcript(s) free, within the analyzed cell, meaning that such a nucleic acid sequence will not give rise to any identified RNA molecule, especially a RNA molecule that would have been transcribed from genomic DNA in the analyzed cell, nor hybridize with RNA primers involved in replication process in a metabolically active cell containing said nucleic acid sequence. Such a nucleic acid sequence cannot be detected by a probe aimed at detecting the result of transcription events occurring in a cell.

However, the fact that the RNA-free nucleic acid sequence is a sequence has no strictly corresponding, i.e. complementary or matching, RNA, especially no RNA transcript(s) resulting from the transcription process occurring naturally in the living eukaryotic cell under assay, does not prevent the target sequence of the first probe from having a particular portion which is complementary to RNA transcript(s) or a portion thereof. According to a particular embodiment, a nucleic acid sequence having "no identified corresponding annealing RNA in a metabolically active cell" is therefore a sequence having no identified corresponding annealing RNA within a specific portion of its sequence, in particular a small portion of its sequence, e.g. in a portion representing less than 70% or less than 50% or less than 20% or less than about 10% of the target.

According to a particular embodiment, a nucleic acid sequence having "no identified corresponding annealing RNA in a metabolically active cell" is a sequence having substantially no strictly corresponding, i.e. complementary or matching, RNA, especially no RNA transcript(s) resulting from the transcription process occurring naturally in the living eukaryotic cell under assay in the detection conditions of the transcripts disclosed herein. Such a nucleic acid sequence remains substantially RNA-free during transcription and replication of said DNA genome, meaning that the amounts of RNA transcripts that would be found annealed to said nucleic acid sequence remain below the detection level in experimental conditions of standard detection of hybridization, in particular they do not influence the experiments conducted herein, i.e. their signals do not exceed background levels or noise.

Especially, it is indicated that the amounts of such transcripts would not be sufficient to allow their detection after treatment with DNAse, in particular DNAseI according to the invention. These amounts would represent minor amounts with respect to the whole amount of transcripts.

It is pointed out that such a sequence may be identified starting from the literature describing transcription and replication processes of gDNA or in databases, having regard to annotation(s) available in said databases, or as a result of deductions arising from said annotations.

According to a particular embodiment, such a nucleic acid sequence having "no identified corresponding annealing RNA in a metabolically active cell" or "substantially no identified corresponding annealing RNA in a metabolically active cell" is a sequence located near or encompassing an origin of replication of a genome. The particular localization of said sequence, i.e. located proximal to, or including, or overlapping known origin(s) of replication(s), is as described above.

Consequently, in a particular embodiment, a first nucleotide probe whose sequence would strictly match the sequence of a nucleic acid sequence as discussed above, would not hybridize with any RNA molecule naturally expressed within a metabolically active cell.

Such a nucleic acid sequence is thus characterized in that it does not bear any coding information that would be reflected at the transcription level of the DNA processing in a cell.

According to a particular embodiment, a first nucleotide probe whose sequence would substantially match the sequence of a RNA free nucleic acid sequence as discussed above, or at least match said sequence over a substantial portion of its whole length, would substantially not hybridize with any RNA molecule naturally expressed within a metabolically active cell, or would not hybridize on the whole length with such RNA molecule.

According to a particular embodiment, the target region referred to herein is located proximal to the $O_H$ replication origin in the human mtDNA, and in particular comprises, encompasses or consists of the DNA segment of mitochondrial gDNA localized between nucleotide position 446 and nucleotide position 162024 on the H strand of the mt genome, which corresponds to sequence SEQ ID NO: 19, of the mitochondrial genome of a human eukaryotic cell, said segment extending over a length of about 80 to about 1200 nucleotides. According to a particular embodiment, the target region referred to comprises, encompasses or consists of the DNA segment of mitochondrial gDNA localized between nucleotide position 446 and nucleotide position 16366. According to a particular embodiment, the target region referred to herein is located proximal to the $O_H$ replication origin in the human mtDNA, and in particular comprises, encompasses or consists of the DNA segment of mitochondrial gDNA localized between nucleotide position 544 and nucleotide position 162024 on the H strand of the mt genome, which corresponds to sequence SEQ ID NO: 1 concatenated with SEQ ID NO: 19, of the mitochondrial genome of a human eukaryotic cell, said segment extending over a length of about 80 to about 1200 nucleotides. By definition, nucleotide positions are indicated with respect to the H strand.

SEQ ID NO: 19 is defined as nucleotide sequence: ttctttc atggggaagc agatttgggt accacccaag tattgactca cccatcaaca accgctatgt atttcgtaca ttactgccag ccaccatgaa tattgtacgg taccataaat acttgaccac ctgtagtaca taaaaaccca atccacatca aaacccctc cccatgctta caagcaagta cagcaatcaa ccctcaacta tcacacatca actgcaactc caaagccacc cctcacccac taggatacca acaaacctac ccaccttaa cagtacatag tacataaagc catttaccgt acatagcaca tta- cagtcaa atccttctc gtccccatgg atgacccccc tcagataggg gtcccttgac caccatcctc cgtgaaatca atatcccgca caagagtgct actctcctcg ctccgggccc ataacacttg ggggtagcta aagtgaactg tatccgacat ctggttccta cttcagggtc ataaagccta aatagcccac acgttcccct taaataagac atcacgatg gatcacaggt ctatcaccct attaccact cacgggagct ctccatgcat ttggtatttt cgtctggggg gtatgcacgc gatagcattg cgagacgctg gagccggagc accctatgtc gcagtatctg tctttgattc ctgcctcatc ctattattta tcgcacctac gttcaatatt acaggcgaac atacttacta aagtgtgtta attaattaat gcttgtagga cat- aataata acaattgaat gtctgcacag ccactttcca cacagacatc ataacaaaaa atttccacca aaccccccct ccccgcttc tggccacagc act- taaacac atctctgcca aacccaaaa acaaagaacc ctaacaccag cctaaccaga tttcaaattt tatctttgg cggtatgcac ttttaacagt caccccc- caa ctaac.

SEQ ID NO:19 corresponds to the human mt DNA fragment between coordinates 16024 and 445 of the circular human mt gDNA, resulting from the concatenation of the fragment between positions 16024 and 16568 and the fragment between positions 1 and 445 (numerotation is made on the H-strand), from Genbank sequence reference NC_012920.1.

By "conditions enabling in situ hybridization" it is meant that the target region is rendered physically accessible to the probe in order to enable the hybridization of said probe to the target region.

According to a particular embodiment, the hybridization of the probe to the target region may be only partial along the entire length of the probe or the target region, but sufficient to be specific and stable during washing step(s) following the hybridization.

According to another embodiment, the hybridization of the first nucleotide probe to the target region occurs over the length of the probe and/or over the length of the target region. Conditions for said hybridization are defined above.

According to a particular embodiment, to render the target region accessible to the probe in order to enable the hybridization of said probe to the target region, said target region has to be available under the form of an accessible single stranded of gDNA even transiently during the replication process. According to a particular embodiment, it is the nucleic acid sequence which has no identified corresponding annealing RNA that has to be available under the form of an accessible single stranded of gDNA even transiently during the replication process.

According to a particular embodiment, the first nucleotide probe strictly anneals to the above-mentioned nucleic acid sequence comprised in the target region that has no identified corresponding annealing RNA in a metabolically active cell. In other words, in said embodiment, when hybridizing to the nucleic acid sequence comprised in the target region which has no identified corresponding annealing RNA, the first probe does not overflow the boundaries of said nucleic acid sequence.

Considering the mitochondrial genomic DNA, the D-loop region of said DNA can be found as a specific structure involving a three-stranded DNA structure that is formed when a newly synthesized single DNA strand remains bound to one of the parental DNA strand of the gDNA and displaces one of the duplex parental strand.

When present, such a three-stranded DNA structure might help rendering a target region located in the D-loop structure or in the vicinity of this structure accessible to the probe. The target region is, in this configuration, either located in a naturally transiently open segment of two complementary single strands of gDNA when the mitochondrial genomic DNA is entering replication, or in a region which is impacted by the presence of the third DNA strand that might help to push aside proteins or other elements that might render the target region crowded and/or hinder the target region with the result of rendering said region inaccessible to the probe for subsequent hybridization of said probe to the target region.

In the context of the invention however, initation of replication is considered an event to be detected in mitochondrial gDNA even when the presence of a third DNA strand in a D-loop does not further give rise to the replication of the whole mitochondrial DNA strand. In other words, the initiation of the replication of the mitochondrial gDNA is considered to happen with the formation of a replication bubble, including the formation of a D-loop around the locus of a replication origin.

In a specific embodiment, when the method of the invention is applied to the detection of the occurrence of initiation of replication events in mitochondrial genomic DNA, the method of the invention can permit the specific detection of the D-loop region opening by labeling the mitochondrial genomic DNA with a probe according to the invention hybridizing at least partly the target region located in the vicinity of said D-loop or at a locus included in said D-loop.

According to a particular embodiment, the first nucleotide probe strictly anneals to the above-mentioned nucleic acid sequence comprised in the target region that has no identified corresponding annealing RNA in a metabolically active cell.

According to a particular embodiment, the accessibility of the target region to the first probe of the invention can be improved by performing a step aimed at partially denaturing the genomic DNA molecule comprising the target region, for example by heating the eukaryotic cell comprising said genomic DNA at a temperature in the range of 72 to 78° C., preferably 75° C., for 2 to 8 minutes, preferably 4 to 5 minutes, in particular 5 minutes, prior to the hybridization step.

According to a particular embodiment, said partial denaturation is performed without using any chemical agent resulting in a complete denaturation of nucleic acids. Consequently, treatments with HCl or Pepsin, alkaline agents or ethanol are prohibited. Conversely, the use of chemical agents and/or temperature conditions enabling or assisting a partial denaturation of nucleic acids is possible. An example of chemical agent that can be used is formamide. Combinations between the proposed treatments disclosed herein are encompassed by the present invention. By "partial denaturation" it is meant that the two strands constituting a double stranded nucleic acid are not found completely separated i.e. under the form of single strands, after such a denaturation. According to a specific embodiment, said partial denaturation results in increasing the size of opening(s) or bubble(s) that could be found on the double-stranded nucleic acid of gDNA prior to eliciting its partial denaturation.

According to a particular embodiment wherein temperature and/or chemical agent(s) is(are) used to assist the partial denaturation of the double-stranded target nucleic acid, said agent(s) enable(s) the partial denaturation by performing or assisting the increase in size of opening(s) or bubble(s) on the double-stranded target nucleic acid, to the exclusion of the result consisting in the dissociation of the strands of the double-stranded target nucleic acid, on their whole length. Accordingly, partial denaturation is a denaturation step which leads to relaxed single-stranded DNA in a double-stranded DNA molecule.

In the context of the invention, it might be advantageous to track both the initiation of genomic DNA replication in a cell or tissue and produced RNA molecules, being for example RNA molecules corresponding to transcription products of genomic DNA fragments concomitantly transcribed in said cell or tissue.

Thus, in a particular embodiment, the method of the invention is used for the further detection of at least one RNA molecule corresponding to a transcribed region of a DNA molecule in an eukaryotic cell, which comprises the step of contacting said eukaryotic cell expressing said RNA molecule with at least a second nucleotide probe, and detecting said second nucleotide probe after hybridization with said RNA molecule.

According to a particular embodiment, the DNA molecule giving rise to the RNA transcript molecule detected by the second nucleotide probe is a genomic DNA inside said cell (the analyzed cell).

In a particular embodiment, the labelling of the nucleic acid sequence of the target region on the DNA genome and the RNA molecule is achieved in one step, in particular simultaneously.

In a particular embodiment, the detection of the nucleic acid sequence of the target region on the DNA genome and the RNA molecule is achieved in one step, in particular simultaneously.

In the context of the invention, the hybridization of the second nucleotide probe to a RNA molecule corresponding to a transcribed region of a DNA molecule is achieved by obtaining a close interaction of the nucleotide probe and the RNA molecule that is expected to be revealed by the detection of the nucleotide probe. Such an interaction can be achieved by the formation of hydrogen bonds between the nucleotide probe and RNA molecule, which is a typical example of the interactions between complementary nucleotide molecules. Hydrogen bonds can be found, for example, in the annealing of two complementary strands of DNA.

Typically, a nucleotide probe designed for hybridizing to a RNA fragment (RNA molecule) is a labelled nucleic sequence fragment complementary to the RNA fragment to detect. The nucleic acid sequence of the probe should be at least partly complementary to at least a part of the RNA molecule to detect, i.e. should be complementary over a region sufficient to enable stable base pairing.

However, according to other embodiments, the interaction of the nucleotide probe and the RNA molecule can also involve van der Waals interactions, ionic bonds or covalent linkages. Such interaction(s) might imply that the nucleotide probe contains modified nucleotides or bear specific moieties generally not present in nucleotidic molecules.

In a particular embodiment, probe(s) are directly labelled with fluorescent moieties (tags).

Probe(s) is/are preferably nucleotide probe(s), and are especially short sequences of DNA or RNA (cRNA probes or riboprobes) that binds to their complementary RNAs. The invention encompasses probe(s) containing nucleotide(s) coupled or linked to other molecule(s) or moiety(ies).

According to a particular embodiment, the nucleotide probe contains modified nucleotides or bears specific moieties generally not present in nucleotidic molecules. Locked Nucleic Acids (LNA) are modified nucleotides and a class of RNA analogs that have an exceptionally high affinity towards complementary DNA and RNA. They can substitute natural nucleotides in DNA or RNA probes.

The invention encompasses the use of probes suitable for revealing several distinct RNA molecules or fragments thereof, or the use of a single probe targeting distinct RNA molecules or fragments thereof (specific of a pool of RNA molecules or fragments thereof), or the use of a single probe specific of the sequence of a unique RNA molecule or fragment thereof within a cell or tissue. In this context the term "probe" encompasses a plurality of molecular entities used together to reveal one or many RNA molecules, said RNA molecules being distinct or different.

According to a particular embodiment, DNA or RNA molecules targeted by either a first nucleotide probe or a second nucleotide probe may be involved in a RNA/DNA structure.

According to the invention, a probe suitable for revealing RNA molecule(s) is generally, but non-exclusively, labelled. Labelling of the probe can be achieved with either radio- or antibody-discoverable- or fluorescent- or biotinylated-tags or quantum dots, especially fluorescent quantum dots. Said tags or quantum dots are directly or indirectly associated, including coupled, to the probe. According to the type of labelling, the probe can be localized in the biological material using appropriate techniques, such as autoradiography or fluorescence microscopy, respectively. The developments made above with respect to the labelling of the probe aimed at revealing the target region in the DNA genome are also applicable to the labelling of the probe(s) aimed at detecting RNA molecule(s).

Detected RNA molecule(s) can be polycistronic RNA, RNA corresponding to transcribed fragments of genomic DNA (nuclear and/or mitochondrial genomic DNA), processed or unprocessed RNA(s) in said cell.

In a particular embodiment of the invention, the first probe aimed at revealing a gDNA target region is a single stranded DNA fragment ranging in size from 80 bp to 1000, 2000 or 3000 bp. Such a probe can range in size from 90 to 150, 200, 300 or 500 bp, in particular from 95 to 110, 120 or 130 bp, preferably sizing 99 bp. According to a particular embodiment, the first probe ranges in size from 200, 400 or 600 bp to 900, 1000, 1100 or 1300 bp. In a specific embodiment, the first nucleotide probe is a single stranded DNA fragment ranging in size from 80 to 3000 bp, or from 80 to 2000 bp or from 80 to 1200 or to 1500 bp.

FIG. 22 discloses experiments demonstrating that the efficiency of the 3D-FISH/mTRIP method of the invention is not affected by the size of the probe.

Therefore, the invention also relates to nucleic acid molecules for use as probes, in particular as first probes according to the present invention, which are specific for the segment of mitochondrial gDNA localized between nucleotide position 446 and nucleotide position 162024 on the H strand of the mt genome (SEQ ID NO:19) or are specific for a segment having 80% identity with such a segment (SEQ ID NO:19), or are specific for fragments thereof. According to a particular embodiment, said nucleic acid molecules are specific for the segment of mitochondrial gDNA between nucleotide position 446 and nucleotide position 16366 (numbered with respect to the H strand of the mt genome) of the mitochondrial genome of a human eukaryotic cell. According to another embodiment, nucleic acid molecules are complementary to a nucleic acid sequence that has at least 80% identity with a target DNA region localized between nucleotide position 446 and nucleotide position 162024 on the H strand of the mt genome, in particular nucleotide position 446 and nucleotide position 16366, of the mitochondrial genome of a human eukaryotic cell.

Nucleic acid molecule of the invention may therefore be selected among the groups of:
   i. a nucleic acid molecule comprising SEQ ID NO: 17 and SEQ ID NO:
   18, in particular a nucleic acid molecule complementary to or at least complementary to or which hybridizes with the sequence of mt DNA or from nucleotide position 425 to nucleotide position 16366 on the H strand of the mt genome, or
   ii. a nucleic acid molecule whose sequence is framed by SEQ ID NO: 1 and SEQ ID NO: 17, in particular as disclosed in SEQ ID NO:19, and which is complementary to or at least partly complementary to or hybridizes with the sequence of mt gDNA from nucleotide position 446 to nucleotide position 225 on the H strand of the mt genome, said nucleic acid molecule having from 80 to about 400 nucleotides; or
   iii. a nucleic acid molecule whose sequence is framed by SEQ ID NO: 1 and SEQ ID NO: 18, in particular as disclosed in SEQ ID NO:19, and which is complementary to or at least partly complementary to or hybridizes with the sequence of mt gDNA from nucleotide position 446 to nucleotide position 16366 on the H strand of the mt genome, said nucleic acid molecule having from 80 to about 800 nucleotides; or
   iv. a nucleic acid molecule whose sequence comprises, in this order, SEQ ID NO: 1, SEQ ID NO:17 and SEQ ID NO: 18, in particular as disclosed in SEQ ID NO:19, and which is complementary to or at least partly complementary to or hybridizes with the sequence of mt gDNA from nucleotide position 446 to nucleotide position 16024 on the H strand of the mt genome, said nucleic acid molecule having from 80 to about 1200 nucleotides.

According to a particular embodiment, a probe according to the present invention is specific for the segment of mitochondrial gDNA localized between nucleotide position 544 and nucleotide position 162024 on the H strand of the mt genome (SEQ ID NO:1 concatenated with SEQ ID NO:19) or is specific for a segment having 80% identity with such a segment (SEQ ID NO:1 concatenated with SEQ ID NO:19), or is specific for fragments thereof.

According to another embodiment, a nucleic acid molecule probe of the invention is complementary to a nucleic acid sequence that has at least 80% identity with a target DNA region localized between nucleotide position 544 and nucleotide position 162024 on the H strand of the mt genome, in particular nucleotide position 544 and nucleotide position 16366, of the mitochondrial genome of a human eukaryotic cell.

Considering the second probe aimed at revealing RNA molecule(s), according to a particular embodiment of the invention, said second probe is a single stranded nucleotidic DNA fragment ranging in size from 100 bp to 3000 bp, and preferably sizing between 100, 200, 300 bp and 1000, 1200, 1500, 2000 bp when aimed at detecting mitochondrial transcripts.

According to a particular embodiment, the size and/or sequence of second probe(s) aimed at revealing RNA molecule(s) is particularly adapted to enable the detection of transcription products resulting from the transcription of coding segments of genomic DNA, especially segments corresponding to genes.

As stated above, in a particular embodiment, the nucleic acid molecule suitable for use as first nucleotide probe is specific for a segment of a non transcribed mitochondrial gDNA, especially an entirely non-transcribed mitochondrial gDNA segment, according to the definition provided herein.

Accordingly, the first nucleotide probe or molecule is complementary of a genomic DNA region that has no corresponding RNA transcript at a cellular level, and therefore remains RNA-free at the cellular level.

In a particular embodiment, the first nucleotide probe or molecule targets the genomic DNA sequence localized between the two promoters PH1 (or HSP—Heavy Strand Promoter) and LSP (Light Strand Promoter) of the mitochondrial genome of a eukaryotic cell. Both the HSP and LSP promoters are found in all eukaryotic mtDNA although their name might differ depending on the species to which the considered eukaryotic mtDNA belongs. The corresponding names can be identified through the literature.

The respective position (coordinates) of these two promoters on the human mitochondrial genome (NCBI, GenBank or MITOMAP sequence reference NC_012920.1) is indicated in Table 2.

In the human mitochondrial genome, such a first probe or nucleic acid molecule sequence has been designated mREP by the inventors. Coordinates of this sequence are given in Table 1 (NCBI, GenBank or MITOMAP sequence NC_012920.1, used as reference). mREP (SEQ ID No 1) is also disclosed in FIG. 13a.

In another embodiment, said first probe comprises the mREP sequence (SEQ ID No 1).

In a specific embodiment, the first nucleotide probe or molecule is complementary to a nucleic acid sequence that has at least 80% identity with the target DNA region that is localized between the two promoters PH1 (or HSP) and LSP of the mitochondrial genome of a eukaryotic cell, or has at least 80% identity with mREP.

By "at least 80% identity" it is meant that their sequence of nucleotides differ from less than 20%, calculated over the entire length of the considered sequence (global alignment calculated for example by the Needleman and Wunsch algorithm). The complementarity is similarly determined by such a global alignment. In a particular embodiment, for example when compared sequences substantially differ in their length, identity and complementary can be determined using the same cutoff values by using a local alignment calculated for example by the Smith and Waterman algorithm. The modifications of nucleotides are especially substitutions.

A sequence which is said to be partly complementary to a sequence of reference may be a sequence with "at least 80% identity" with said sequence of reference.

The genomic DNA sequence localized between the two promoters PH1 (or HSP) and LSP of the mitochondrial genome of a eukaryotic cell is part of a highly variable region in the mitochondrial genome. FIG. 13b discloses polymorphism variations known to date with respect to the human mREP sequence (SEQ ID No 1) of the invention. However, very few of these variations can be found simultaneously in an individual, i.e. only 1, 2, 3 or 4 of these variations can be found simultaneously. Said variations are generally linked to a subpopulation type (e.g. Caucasian, African . . . ). These polymorphism variations are a basis for the design of variants of mREP.

Table 3 discloses the percentages of identity between the sequences corresponding to the mREP probe (SEQ ID No 1) in several organisms and species, with respect to human mREP probe, along with coordinates of said sequences on the corresponding mitochondrial genomes (SEQ ID No 2 to 16).

TABLE 3

Percentages of identity between the sequences (SEQ ID No 2 to 16) corresponding to the mREP (SEQ ID No 1) probe in several organisms and species. Refseq are NCBI or GenBank reference numbers.

| Organism | Accession number Refseq | mtDNA Genome size (bp) | mREP alignment coordinates |
|---|---|---|---|
| Primates | | | |
| Homo sapiens | NC_012920.1 | 16 569 | 446-544 |
| Pan troglodytes | NC_001643.1 | 16 554 | 16424-16521 |
| Pan paniscus | NC_001644.1 | 16 563 | 16433-16530 |
| Gorilla gorilla | NC_001645.1 | 16 364 | 16233-16332 |
| Pongo pygmaeus | NC_001646.1 | 16 389 | 16247-16357 |
| Hybolates lar | NC_002082.1 | 16 472 | 16148-16246 |
| Cebus albifrons | NC_002763.1 | 16 554 | 15946-16044 |
| Other mammalians | | | |
| Capra hircus | NC_005044.2 | 16 643 | 15519-15630 |
| Mus musculus | NC_005089.1 | 16 299 | 15654-15757 |
| Oryctolagus cuniculus | NC_001913.1 | 17 245 | 15767-15867 |
| Canis lupus | NC_008092.1 | 16 729 | 16456-16555 |
| Rattus sordidus | NC_014871.1 | 16 309 | 15643-15744 |
| Felis catus | NC_001700.1 | 17 009 | 759-864 |
| Castor canadensis | NC_015108.1 | 16 701 | 15766-15866 |
| Avian | | | |
| Gallus gallus | NC_001323.1 | 16 775 | 473-571 |
| Fish | | | |
| Danio rerio | NC_002333.2 | 16 596 | 682-782 |

In a specific embodiment, the first nucleotide probe comprises a nucleic acid molecule having the sequence of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, or the sequence that is complementary of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, or is a fragment of said sequences.

In a specific embodiment, the first nucleotide probe comprises a nucleic acid molecule encompassing fragments of the nucleic acid sequence of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, or the nucleic acid sequence that is complementary of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16.

In a specific embodiment, the first nucleotide probe consists of a nucleic acid molecule that has the nucleic acid sequence of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, or the nucleic acid sequence that is complementary of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16.

According to a particular embodiment, the first nucleotide probe is a nucleic acid that has at least 80% identity with the nucleic acid sequence of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, or the nucleic acid sequence that is complementary of any one of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16.

In a particular embodiment, the first nucleotide probe encompasses a mix of more than one, but distinct probes, especially probes comprising nucleic acid molecules having distinct sequences from each other, chosen among the sequences disclosed above. In a specific embodiment, the first nucleotide probe encompasses a mix of two nucleic acid molecules having sequences that are complementary to each other. Such a mix might have to be denaturated prior to its use.

FIG. 13b discloses polymorphism variations known to date with respect to the mREP sequence. These polymorphism variations may be used to design probes alternative to mREP corresponding to SEQ ID No 1.

FIG. 13c discloses alignments between the human mREP sequence and the corresponding sequences in different organisms, which are also disclosed herein under SED ID No 2 to 16.

According to a particular embodiment of the invention, when both mitochondrial gDNA and RNA molecules are detected, the at least second nucleotide probe detecting RNA molecule(s) targets RNA/DNA hybrid molecule(s) or targets RNA hybridizing to the mitochondrial gDNA in the D-loop region of the mitochondrial gDNA.

In a specific embodiment, the second nucleotide probe is specific for a RNA molecule involved the formation of a RNA/DNA hybrid structure or a fragment thereof, or is specific for a RNA hybridizing the gDNA in the D-loop region or a fragment thereof, and may comprises or consists of the sequence disclosed under SEQ ID NO 17 or SEQ ID NO 18, or be a fragment thereof. In a particular embodiment the second nucleotide probe has at least 80% identity with SEQ ID NO 17 or SEQ ID NO 18. In a particular embodiment the second nucleotide probe has the sequence disclosed under SEQ ID NO 17 or SEQ ID NO 18.

SEQ ID NO:17 is the sequence of the PL-OH probe (position 225-425) according to the reference human mitochondrial sequence NC_012920.1, GenBank:

```
225 gtagga cataataata acaattgaat gtctgcacag
    ccactttcca cacagacatc ataacaaaaa atttccacca
    aacccccct cccccgcttc tggccacagc acttaaacac
```

-continued
```
atctctgcca aacccaaaa acaaagaacc ctaacaccag cctaaccaga tttcaaattt tatcttttgg cggtatgcac ttttta 425
```

SEQ ID NO:18 is the sequence of the 7S probe (position 16366-16566) according to the reference human mitochondrial sequence NC_012920.1, GenBank:

```
16366 catgg atgacccccc tcagatagg gtcccttgac caccatcctc cgtgaaatca atatcccgca caagagtgct actctcctcg ctccgggcc ataacacttg ggggtagcta aagtgaactg tatccgacat ctggttccta cttcagggtc ataaagccta aatagcccac acgttcccct taaataagac atcacga 16566
```

In a particular embodiment, the first nucleotide or the second nucleotide probe is directly labelled, in particular with a fluorescent group.

Labelling can be achieved with groups or labels such as Biotin, digoxin and digoxigenin (DIG), alkaline phosphatase and fluorescent groups or labels such as fluorescein (FITC), Texas Red and rhodamine or derivatives thereof, or dyes including coumarins, rhodamines, carbopyronins, oxazines or derivatives thereof or quantum dots, especially fluorescent quantum dots, or derivatives thereof.

By "directly labelled", it is meant that the detection of the label does not require the intervention of another, i.e. secondary, chemical agent or compound, including an antibody, to be achieved. Such a direct labelling might improve the specificity of the labelling.

Labelling can be achieved through a commercial kit, for example according to a nick translation procedure. An example of such a commercial kit is the Nick Translation Atto NT Labeling kit from JenaBioscience; comprising the following dyes: Atto425=blue, Atto488=green, Atto550=red.

In a particular embodiment, the first nucleotide probe comprises modified nucleotides, as disclosed herein.

The invention also relates to a method for the in situ hybridization and detection of nucleotidic material within at least one eukaryotic cell, which comprises the steps of:
 a. Fixation of said cell in 1 to 4% paraformaldehyde (PFA), preferably 2% PFA for about 20 to 30 minutes, especially 30 minutes,
 b. Permeabilization of said fixed cell with 0.5% to 1% Triton X100 in PBS (Phosphate Buffered Saline Buffer) 1×, for about 5 to 10 minutes at 4° C., especially 5 minutes,
 c. Denaturation of the nucleic acid contents of said permeabilized fixed cell by heating at a temperature in a range of 72 to 78° C., preferably 75° C., for 2 to 8 minutes, preferably 4 to 5 minutes, especially 5 minutes,
 d. Contacting the nucleic acid(s) in the cell treated according to step (c) with nucleotide probe(s) defined herein as first probe(s) and optionally second probe(s) to enable hybridization of said nucleic acid(s) with said probe(s), wherein the probe(s) has(have) a size ranging from 80 to 3000 nucleotides, or from 90 to 1000 nucleotides, in particular from 95 to 110 nucleotides, said nucleotide probe(s) being contained in an hybridization solution comprising from 100 ng/µl to 10 µg/µl of salmon sperm DNA,
 e. Detecting the nucleic acid(s) hybridized to the probe(s) added in step (d).

The denaturation step of said method can further be carried out in an appropriate buffer and/or with a chemical agent aimed at partially denaturing nucleic acids, as disclosed herein.

According to a specific embodiment of the invention, the denaturation step of the nucleic acid contents of a fixed cell is carried out by heating at a temperature in a range of 72 to 78° C., preferably 75° C., for 2 to 8 minutes, preferably 4 to 5 minutes, especially 5 minutes, in the presence of a chemical agent such as formamide, especially a solution of 70% formamide or 70% formamide/2×SSC.

Said method can further comprise a step of washing the cell(s) contacted with the nucleotide probe(s) with an appropriate buffer prior to the detection step.

According to a particular embodiment, the hybridization step is carried out during about 15 hours at 37° C.

According to a particular embodiment, the method of the invention further comprises steps enabling labelling and detection of at least one protein of interest within the eukaryotic cell, in particular by immunofluorescence.

The detection can especially be carried out by single-cell imaging.

To this end, the cell(s) or tissue(s) under assay can be contacted with antibodies specific for the protein(s) of which detection is sought.

According to a particular embodiment, the detection of nucleotidic material and of the protein of interest is achieved in one step, in particular simultaneously.

A step of analysis of the result(s) of the detection(s) might be subsequently performed.

Fixation of cells can alternatively be performed with agents such as paraffin, acetone, methanol, ethanol, a combination of methanol and acetone a combination of methanol and ethanol, formalin, a combination of paraformaldehyde and methanol, or any combination(s) of the agents disclosed herein.

Said steps that can be involved in a method according to the invention are detailed hereafter.

1. Cell(s) or Tissue(s) Fixation

According to a particular embodiment, the fixation of cell(s) or tissue(s) is performed on glass slide(s) with a solution of 1 to 4% paraformaldehyde (PFA), preferably 2% PFA for about 20 to 30 minutes, especially 30 minutes. According to a specific embodiment, the fixation is carried out with a solution of 2% PFA for about 30 minutes. Said fixation can be carried out at room temperature, RT.

After the fixation, storage of the fixed material can be performed in a buffer such as PBS 1× (during maximum one year at 4° C.).

Alternatively, fixation can be carried out according to any one of the following protocols:
 Acetone Fixation (Fix cells in −20° C. acetone for 5-10 minutes);
 Methanol Fixation (Fix cells in −20° C. methanol for 5-10 minutes);
 Ethanol Fixation (Fix cells in cooled 95% ethanol, 5% glacial acetic acid for 5-10 minutes);
 Methanol-Acetone Fixation (Fix in cooled methanol, 10 minutes at −20° C.; Remove excess methanol);
 Methanol-Acetone Mix Fixation (1:1 methanol and acetone mixture.; Make the mixture fresh and fix cells at −20 C for 5-10 minutes);

Methanol-Ethanol Mix Fixation (1:1 methanol and ethanol mixture, Make the mixture fresh and fix cells at −20 C for 5-10 minutes);

Formalin Fixation (Fix cells in 10% neutral buffered formalin for 5-10 minutes);

Paraformaldehyde-Methanol Fixation (Fix in 4% paraformaldehyde for 10-20 minutes, Rinse briefly with PBS, Permeabilize with cooled methanol for 5-10 minutes at −20° C.

While cell(s) or tissue(s) fixation is generally not performed at this stage in standard DNA FISH procedures, standard RNA FISH procedures require the fixation of cell(s) or tissue(s) with 4% PFA for 10 minutes minimum.

2. Cell(s) or Tissue(s) Permeabilization

In particular embodiments, the permeabilization step might be required to allow a good infiltration of the probes, especially through cell membranes, in order for the probes to reach their target sequence. Known chemical reagents used for permeabilizing cells in the prior art are HCl, detergents such as Triton or SDS or Proteinase K.

According to a particular embodiment of the invention, fixed cell(s) or tissue(s) are permeabilized using a 0.5% to 1% Triton X100 solution in an appropriate buffer, such as PBS 1×, for example during 5 min. Said permeabilization can be carried out at 4° C.

According to a particular embodiment, fixed cell(s) or tissue(s) can be washed up to 3 times in PBS 1× prior to the permeabilization, and up to 4 times in PBS 1× after the permeabilization.

According to a particular embodiment, the permeabilization can be followed by incubation of the cell(s) or tissue(s) in 50% Formamide/2×SSC (saline-sodium citrate buffer) in PBS 1× at RT during 30 min, and further switching to 70% Formamide/2×SSC just before the denaturation.

Optionally, a control assay for the probe specificity can be performed by incubating the samples during 1 hour at 37° C. in RNase or DNase solution (100 ug/ml), with an additional washing up to 3 times in PBS 1× prior to the incubation of the cell(s) or tissue(s) in Formamide.

Standard DNA FISH procedures generally involve a heat treatment of the glass slides (for example during 90° C. 1 h30 or at 37° C. overnight) to remove all enzymes that could interfere with the experiment, and the permeabilization is achieved by incubation with 0.005% Pepsin/0.001M HCl at 37° C. for 15 min, washing in (4%) paraformaldehyde/PBS, then incubating in ethanol series: 70%, 90%, 100%, further followed by RNase treatment that is performed to remove primary transcripts and subsequent washing and dehydratation in ethanol series. The samples are finally air dried.

Standard RNA FISH procedures generally require permeabilization with Triton X100 0.5% in buffer (the composition of which might contain PIPES, MgCl2, sucrose or NaCl . . . ), washing in 4% PFA/PBS for 10 min on ice and further washings (twice) in 70% ethanol and subsequent dehydratation in ethanol series: 80%, 95%, 100% ethanol and air drying of the samples on a heating plate at 42° C.

To the contrary, the method of the invention in conducted in absence of enzymatic (i.e. pepsin), acidic (i.e. HCl) or alkaline treatment, alcoholic treatment (i.e. ethanol) or drying agent or treatment (i.e. air dry).

3. Denaturation

The denaturation step is performed by heating the samples comprising the assayed cell(s) or tissue(s) at a temperature in a range of 72 to 78° C., preferably 75° C., for 2 to 8 minutes, preferably during 4 to 5 minutes, especially 5 minutes. According to a specific embodiment, the samples are heated at 75° C. during 5 minutes. The samples can then be kept on ice until the probe(s) are ready.

While the denaturation step is generally not performed in standard RNA FISH procedures, because such a step would be unnecessary since RNAs are single stranded molecules, standard DNA FISH procedures generally involve heating the samples at temperatures close to 80° C., and the assistance of other treatments such as chemical or physical treatments usually used to denaturate nucleic acids (e.g. washing with 70% ethanol on ice or dehydratation with ethanol series) in order to obtain single stranded DNA molecules.

However, the denaturation step according to the invention may be carried out in the presence of chemical agent(s) aimed at partially denaturing nucleic acids, or in an appropriate buffer, such as formamide.

4. Probe Design and Preparation

According to the invention, probe(s) are preferably small in size (3 kb or shorter, preferably 1 kb or shorter) and the direct use of fluorescence probe(s) for labelling DNA(s) and RNA(s) is preferred.

When a step of nick translation (direct fluorescence) and Biotin/Digoxigenin (undirect fluorescence) is necessary for probe labelling, thus further requiring primary and secondary fluorescent antibodies to reveal Biotin/Digoxigenin-DNA or RNA probe hybridization, a kit such as the Jena Nick Translation kit can be used to label the probe(s) (Atto fluorescence) and the quantity of DNA recovered after purification should be estimated (about 10% loss compared to input).

5. Pre-Hybridisation

According to a particular embodiment, a pre-hybridization step can be performed, comprising the following steps:

For 1 slide, mix in 25 µL final volume:
40 ng fluorescent probe (final concentration: 1.6 ng/µl)
400 ng salmon sperm DNA (from 100 ng/µl solution)
Buffer: 10% dextran sulfate/50% Formamide/2×SSC in PBS 1×
Incubate the mix 10 min at 80° C. in the dark Optionally, pre-hybridized slides can be put to pre cool 30 min at 37° C. in the dark before incubating slides.

Standard DNA and RNA FISH procedures generally require a higher concentration of fluorescent or tagged probe (final concentration of about 10 ng/µl) and the addition of Cot-1 DNA and Salmon Sperm DNA at a final concentration of more than 0.5 µg/µL. The mix is then incubated (5 to 10 min) at 74-85° C. in the dark.

According to a particular embodiment, the pre-hybridisation and/or hybridisation step is carried out in absence of Cot-1 DNA.

6. Hybridization

According to a particular embodiment of the invention, the hybridization step is be carried out during about 15 hours at 37° C. in a standard buffer such as illustrated in the examples, e.g. an hybridization buffer with 50% formamide, 10% dextran sulphate, in 2×SSC pH 7.0 or another similar buffer as appropriate.

More specifically, the hybridization step can be done by incubating the samples about 15 hours at 37° C. on a heating metal block in the dark. Standard DNA and RNA FISH procedures generally require overnight hybridization.

7. Washes and Mounting

According to a particular embodiment, the method of the invention further comprises a step of washing the cell contacted with the nucleotide probe(s) with an appropriate buffer prior to the detection step.

For example, washing can be performed up to 2 times for 2 min in 3 mL 2×SSC at RT (cover with black top to protect from light), then up to 2 times in 1×SSC at RT, then up to 2 times in 0.1×SSC at RT. Finally, an ultimate washing can be performed up to 2 times in PBS 1× at RT (all in the dark).

At this point a simple 2D imaging can be performed. In order to obtain a greater resolution, 3D analysis can be preferred.

8. 3D-FISH to Achieve mTRIP (Mitochondrial Transcription and Replication Imaging Protocol)

When 3D-FISH is performed, the following steps may be carried out.

Incubate 1 h in Hoechst 33342 10 ug/mL final
Wash 5 times in PBS 1×
Mount on 20 uL PBS 1× on 70% Ethanol cleaned and dried slides.
Keep the slides in Dark clean box at RT until confocal analysis.

As described until this point, the procedure allows the labelling of genomic DNA, especially mtDNA and RNAs. Further steps are required for additional labelling of mitochondrial or cellular proteins.

According to an advantageous embodiment, the method of the invention further comprises steps enabling labelling and detection of at least one protein of interest within the eukaryotic cell treated for in situ hybridization and detection of nucleotidic material. For this purpose, immunofluorescence can be used and the cell can be contacted with antibodies specific for the protein(s) of which detection is sought. Antibodies raised against a particular protein or epitope can be obtained according to usual techniques commonly used in the immunological field.

In a particular embodiment, the mTRIP/3D-FISH method of the invention enables to achieve the detection of the nucleotidic material and the protein of interest in one step, in particular simultaneously.

9. 3D-FISH/mTRIP Coupled Immunofluorescence:

The following steps might be performed:
Incubate the slide with BSA 5% in PBS 1× 1 h RT in the dark.
Wash 2 times in PBS 1×
Incubate with Primary antibody in BSA 1%, PBS 1×, 1 h RT dark
Wash 3 times in PBS 1×
Incubate with Secondary antibody in Hoechst 33342 10 µg/ml final,
BSA 1%, PBS 1×, 1 h RT dark
Wash 5 times in PBS 1×
Mount on 20 µL PBS 1× on 70% EtOH cleaned and dried slides.
Keep the slides in dark clean box at RT until confocal analysis.

Example of a Protocol According to the Invention Detailing Particular Steps Performed in a Particular Embodiment of the Method of the Invention The following procedure is suitable for the detection of the occurrence of initiation of replication events in the mitochondrial genomic DNA of human cell lines and human primary fibroblasts as well as in cells of other eukaryote organisms.

The design of mtDNA probe(s) used for tracking the occurrence of initiation of replication events has to be adapted to the sequence of the corresponding mitochondrial genomes (see Table 3 that gives correspondence of the mREP probe in other organisms).

1. Cell Fixation
Cells Fixation on glass slides: 2% paraformaldhehyde or PFA for 30 min at room temperature, RT.
Storage in PBS 1× (maximum one year at 4° C.)

2. Cell Permeabilization
Wash 3 times in PBS 1×
Permeabilize 5 min at 4° C. in 0.5% Triton X100 in PBS 1×
Wash 4 times in PBS 1×
Optional (control assay for the probe specificity)
Incubate 1 h at 37° C. in RNase or DNase solution (100 ug/ml)
Wash 3× in PBS 1×
Incubate the cells in 50% Formamide/2×SSC in PBS 1× at RT 30 min
Switch to 70% Formamide/2×SSC just before the denaturation 3. Denaturation
denaturate for 4 to 5 min, in particular 5 minutes, at 75° C.
Keep on ice until probe is ready 4. Probe Design and Preparation
size of probes~1 kb or shorter
direct use of fluorescence probes is preferred 5. Pre-Hybridisation
For 1 slide, mix in 25 µL final volume:
40 ng fluorescent probe (final concentration: 1.6 ng/µl)
400 ng salmon sperm DNA (from 100 ng/µl solution)
Buffer: 10% dextran sulfate/50% Formamide/2×SSC in PBS 1×
Incubate the mix 10 min at 80° C. in the dark
Pre cool 30 min at 37° C. in the dark before incubating slides 6. Hybridization
Drop 25 uL of pre-hybridization mix on square parafilm
Invert slides on drops
Incubate 15 hours at 37° C. on a heating metal block in the dark (cover with plastic top to set the dark position)

7. Washes and Mounting
wash 2 times for 2 min in 3 mL 2×SSC at RT
cover with black top to protect from light.
wash 2 times in 1×SSC at RT, then 2 times in 0.1×SSC at RT,
wash 2 times in PBS 1× at RT (all in the dark).

8. 3D-FISH/mTRIP
The following protocol is optimized for 3D Z-scanning of mammalian cells using a confocal spinning disk microscope. Z-stacks of 200 nm. 3D reconstruction using the IMARIS (Bitplane software).
Incubate 1 h in Hoechst 33342 10 ug/mL final
Wash 5 times in PBS 1×
Mount on 20 uL PBS 1× on 70% EtOH cleaned and dried slides.
Keep the slides in Dark clean box at RT until confocal analysis.
Until this point the procedure allows the labelling of mt DNA and RNAs. With the next steps it allows the additional labelling of mitochondrial or cellular proteins.

9. 3D-FISH/mTRIP Coupled Immunofluorescence
The following protocol is optimized for 3D Z-scanning of mammalian cells using a confocal spinning disk microscope. Z-stacks of 200 nm. 3D reconstruction using the IMARIS (Bitplane software).
Incubate the slide with BSA 5% in PBS 1× 1 h RT in the dark.

Wash 2 times in PBS 1×

Incubate with Primary antibody in BSA 1%, PBS 1×, 1 h RT dark

Wash 3 times in PBS 1×

Incubate with Secondary antibody in Hoechst 33342 10 ug/ml final,

BSA 1%, PBS 1×, 1 h RT dark

Wash 5 times in PBS 1×

Mount on 20 uL PBS 1× on 70% EtOH cleaned and dried slides.

Keep the slides in dark clean box at RT until confocal analysis.

The invention also relates to nucleic acid molecule(s) suitable for use as probe(s) as defined herein and especially designated as the "first probe" for use in the process of the invention.

The invention is in particular directed to a nucleic acid molecule suitable for use as a probe suitable for in situ hybridization targeting the genomic DNA.

Therefore, the invention also relates to a nucleic acid molecule suitable for use as a probe, hybridizing with a target region in a eukaryotic genomic DNA, wherein said target region comprises a nucleic acid sequence which has no identified corresponding annealing RNA in the metabolically active cell containing said eukaryotic genomic DNA and therefore remains RNA-free during transcription and replication of said DNA genome. According to a particular embodiment, such a nucleic acid molecule hybridizes with said RNA-free nucleic acid sequence, and has the same length as said RNA-free nucleic acid sequence or is longer.

Nucleic acid molecule(s) or probe(s) disclosed above and herein with respect to a method according to the invention are themselves part of the object of the invention. They are prepared and/or used as either a single stand molecule or a double strand molecule of complementary sequences.

In particular, such nucleic acid molecules are specific for a segment of non transcribed mitochondrial gDNA and comprises or consists of:
  i. the nucleic acid having the sequence of any one of SEQ ID No 1 to SEQ ID No 16 or,
  ii. the nucleic acid that has a sequence that is complementary of any one of SEQ ID No 1 to SEQ ID No 16 or,
  iii. a fragment of (i) or (ii) or,
  iv. a nucleic acid that has at least 80% identity with the nucleic acid sequence of any one of SEQ ID No 1 to SEQ ID No 16 or the nucleic acid sequence that is complementary of any one of SEQ ID No 1 to SEQ ID No 16 or fragments thereof, said nucleic acid molecule being either a single stand molecule or a double strand molecule of complementary sequences.

The invention also relates to a nucleic acid molecule, binding to a RNA molecule or to a RNA/DNA molecule, said RNA or RNA/DNA molecules being molecules hybridizing with a segment of mitochondrial gDNA localized in the mitochondrial gDNA D-loop region, wherein said nucleic acid molecule comprises or has the sequence or is a fragment or has at least 80% identity with sequence of SEQ ID No 17, or comprises or has the sequence or is a fragment or has at least 80% identity with the sequence that is complementary of SEQ ID No 18.

The invention also relates to a kit for carrying out in situ hybridization on fixed cells, comprising a so-called first probe, consisting of a nucleic acid molecule, of the invention, and comprising optionally a so-called second probe, consisting of a nucleic acid molecule, of the invention, hybridizing with a RNA molecule or RNA/DNA hybrid molecule, as disclosed herein.

The invention also relates to a kit comprising a probe, consisting of a nucleic acid molecule, suitable for in situ hybridization targeting the genomic DNA as disclosed herein, and comprising optionally a so-called second probe, consisting of a nucleic acid molecule, of the invention, hybridizing with a RNA molecule or RNA/DNA hybrid molecule, as disclosed herein.

According to a particular embodiment, said kits further comprise probes, consisting of nucleic acid molecule(s), and/or antibody(ies) for additionally detecting protein(s).

Kits to label and detect in a same cell or tissue DNA and optionally RNA and/or proteins are useful for the detection of the occurrence of initiation events in the genomic DNA replication in eukaryote cell(s) or tissue(s).

Said kits can further comprise instructions for use in a process for detecting the occurrence of initiation of replication events in genomic DNA in a eukaryotic cell, according to a method of the invention as disclosed herein.

Said kits can further comprise reagents necessary for carrying out such a process, as disclosed herein.

Said kits can further comprise material, e.g measurement material, data carrier(s), recording support(s), to collect or analyze the data measured by a process according to the invention.

The present invention is of particular interest for analyzing the processing of DNA, RNA or metabolites in cell(s) or tissue(s), and/or analyzing the dynamics of said cell(s) or tissue(s), and/or detecting specific diseases.

The invention is of particular interest for providing means useful for in vitro analysis, in vitro detection and optionally subsequent diagnosis of mitochondrial disease(s) or neoplasic diseases(s) or cancer(s) or in vitro detection or monitoring of myopathies. The invention is also of particular interest for in vitro analyzing, in vitro detecting and optionally subsequently diagnosing mitochondrial disease(s) or neoplasic diseases(s) or cancer(s)

With respect to the interest of analyzing or detecting the occurrence of initiation of replication events in a context of mitochondrial dysfunction, it is knowledgeable to notice that the physiology and metabolism of mitochondria impact not only in the production of cellular energy (ATP) but also in cell growth, cell differentiation, cell signaling and death (apoptosis). Thus, mitochondrial misfunction is associated with a variety of diseases (cancers, myopathies, neuropathologies, infections), and with the ageing process.

Mitochondrial diseases encompass cardiomyopathy, neuropathy, Retinitis pigmentosa, encephalomyopathy, hepatopathy, hypotonia, Renal tubulopathy, Leigh syndrome, Barth syndrome, optic atrophy and Ataxia, Leukodystrophy, Diabetes, Kearns-Sayre syndrome.

Mitochondrial dysfunctions can lead to or are involved in type 2 diabetes, Parkinson, Alzheimer, Atherosclerotic heart disease, stroke or cancers.

The method of the invention, the probes described herein and kits encompassing said probes or permitting to carry out the method of the invention are useful in clinical diagnosis protocols by contributing to means necessary to identify and/or to class diseases associated with mitochondrial dysfunctions according to the default in mitochondrial mtDNA processing, e.g. transcription and replication, or in mtDNA content. This includes genetic diseases (mtDNA depletion diseases) and cancers. The same can be also used to identify mtDNA depletion induced by clinical treatment (i.e., long term treatment with anti-HIV nucleoside analogues deplete mtDNA) or impaired or abolished initiation of mtDNA replication.

The method of the invention, the probes or nucleic acid molecules described herein and kits encompassing said probes or nucleic acid molecules or permitting to carry out the method of the invention can be used in the analysis and detection of mitochondrial disease(s) or disease(s) resulting from mitochondrial dysfunction(s) or impairment, or disease(s) resulting in mitochondrial dysfunction(s) or impairment.

The method of the invention is applicable to all eukaryotic cells, including human, mouse, insect, yeast, fish or plant cell as a diagnosis tool or a biotechnological tool for exploring the functions of said cells.

The method of the invention, the probes or nucleic acid molecules described herein and kits encompassing said probes or nucleic acid molecules or permitting to carry out the method of the invention can also be used in the analysis and detection of neoplasic diseases(s) or cancer(s).

The invention provides means useful for the detection and diagnosis of neoplasic or tumoral cell(s) or tissue(s), and especially to distinguish said cell(s) or tissue(s) among healthy cell(s) or tissue(s).

The present invention is also of particular interest for testing the cytotoxicity of organic and chemical compounds, especially drugs.

The invention also relates to a method for in vitro detecting altered mitochondrial activity in cells, comprising the step of detecting the level of mitochondrial initation of DNA replication with a first probe as disclosed herein and detecting the level of mitochondrial transcripts with a second probe as disclosed herein.

Other examples and features of the invention will be apparent when reading the examples and the figures, which illustrate the experiments conducted by the inventors, in complement to the features and definitions given in the present description.

BRIEF DESCRIPTION OF THE DRAWINGS

FIGS. 3A to 3E. Detection of regions containing mitochondrial replication origins. (A) Schematic localization of DNA and RNA labeling by mt probes used in 3D-FISH assay. DNA labeling is observed on three regions (not at scale), two of which correspond to the major origins of replication of the mt genome ($O_H$ and $O_L$, probes 13 and 8, respectively), and the third (probe 8) to a additional $O_L$ origin of replication, that was previously identified[13]. The distances between mt origins are indicated. (B) Characterization of the $O_H$ region analysed by 3D-FISH with progressively shorter probes. The region covered by each probe is shown on the left panel that also indicates the main genetic elements present in the region (LSP=light-strand promoter; $P_{H1}$ and $P_{H2}$ stand for heavy-strand promoter 1 and 2, respectively; $O_H$=origin of H strand DNA replication; F=tRNA$^{Phe}$; 12S=12S rRNA, P=tRNA$^{Pro}$). Only the probe mREP covers a DNA region that is substantially not transcribed (indicated as RNA-free), while probes 13 and 13-1 cover also transcribed regions. Panels on the right show by 3D-FISH/mTRIP the localization of mitochondrial entities labeled with each of the probes (red); nuclei in blue (Hoechst 33342). Scale bar=10 um. (C) 3D FISH-reconstructed HeLa cells labeled with mREP (red) and mTRANS (green) probes, with or without nuclease treatments. Scale bar=10 um (upper panels), and fluorescence intensity quantification (lower panels). Values of mREP in the presence of DNaseI and of mTRANS in the presence of RNaseA correspond to background. n=30 from three independent experiments: t-test for nuclease-treated versus untreated cells; (*) p<0.001. (D) 3D-FISH/mTRIP coupled IF with mREP (red) probe and anti-Poly (green). On the right, fluorescence intensity quantification of mREP-positive and mREP-negative Poly labeled areas. Examples of the respective areas are shown on the bottom, circled, lower panels: Polyγ; upper panels: merge. n=300 from three independent experiments; T-test (*) p<0.001. (E) 3D-FISH/mTRIP coupled IF with mREP (red) probe and anti-TFAM (green). On the right, fluorescence intensity quantification of mREP-positive and mREP-negative TFAM-labeled areas. Examples of the respective areas are shown on the bottom, circled, lower panels: TFAM; upper panels: merge. n=300 from three independent experiments; T-test (***) p<0.001.

FIGS. 12A to 12D. mREP labels initiation of mtDNA replication. (A) Labeling with the mREP probe anticipates oxydative stress-dependent increase of the mtDNA content. Kinetics of 3D-FISH coupled immunofluorescence (IF) labeling of H2O2-treated HeLa cells; anti-TOM22 (green, upper panels) and either mREP (red, middle panels) or mTRANS (red, lower panels) probes. Scale bar=10 um. (b) Fluorescence intensity quantifications. TOM22; mREP and mTRANS. n=30 from three independent experiments. mtDNA content estimation by qPCR (12S region); expression of the CytC transcript, coded by a nuclear gene, by qPCR. n=3. T-test (*) p<0.05; () p<0.01; (*) p<0.001. Ctrl, untreated. (C) mREP probe colocalizes to various extents with BrdU-positive mitochondria. 3D-reconstructed cells labelled with mREP (red), anti-BrdU (green), and merge; nuclei are labelled by Hoechst (blue). Scale bar=10 μm. Below, 2.5× magnification of two regions, proximal and distal to the nuclear surface are shown on right panels. Circles indicate representative mREP-positive and mREP-negative areas, where BrdU labelling was also measured. (D) Fluorescence intensity measurement of BrdU labelling shows higher values in mREP-negative than in mREP-positive areas. n=300 areas, three independent experiments. (***) p≤0.001.

FIGS. 13A to 13C. mREP sequences and alignments. (a) Human mREP sequence (SEQ ID No 1), having coordinates 446-544 on the human mtDNA sequence disclosed under accession number NC_012920.1 (NCBI or GenBank or MITOMAP accession number) (b) mREP (SEQ ID No 1)—Human polymorphism—variations. Positions where polymorphisms, e.g. nucleotide(s) variation(s), might be found are put on a black background. One skilled in the art can identify variable positions in the mREP sequence from the above-mentioned indications (c) Human mREP alignments with the corresponding sequences (SEQ ID No 2 to 16) in different organisms (Accession numbers disclosed in said figure are NCBI accession numbers http://www.ncbi.nlm.nih.gov/).

FIGS. 15A to 15F. Analysis of mtDNA regulatory regions by mTRIP (A) Fluorescence intensity quantification of probes PL-OH (left) and 7S (right) in presence or absence of indicated nucleases; n=30, three independent experiments: t-test for nuclease-treated versus untreated cells; (***) 0.001. (B) Schematic representation (not to scale) of D-loop region of mtDNA analysed by mTRIP, key elements and coordinates in mtDNA are indicated; vertical grey bars in $O_H$ region represent the three CSB sites; 16S and 12S genes, and 7S region are shown. FISH probes (horizontal black bars) are named and their position on mtDNA is indicated. Below are summarized detected nucleic acids in the corresponding region on scheme, including data of probe mREP from FIG. 3D and of probe PH1-2 from panel E (++: exclusive detection; +: detection, −: no detection; nd=not done). (C) 3D-reconstruction of cells labelled with PL-OH, 7S, and merge. Cells were treated with the nucleases indicated above or untreated. In merge panels arrowheads and arrows indicate foci with the prevalent (1) and alternative (2-6) labelling patterns, respectively, according to the sensitivity to the various nucleases. (D) Nucleic acids detected at large PL-OH and 7S foci, with the pattern number indicated as in panel C (a/o=and/or). (E) Upper panels:

3D-reconstruction of cells labelled with probes PH1-2 in the presence and in the absence of the indicated nuclease. On the right, fluorescence intensity quantification; n=30, three independent experiments: t-test for nuclease-treated versus untreated cells; (***) p≤0.001. Lower panels: 3D-reconstruction of cells colabelled with PH1-2, probe 1, and merge. Percentage of colocalization between probes is shown on the right. (F) Graphic summarizes intensity of fluorescence labelling with different probes in presence or absence of nucleases, normalized to values of mREP (in absence of nucleases).

Figure 16A:
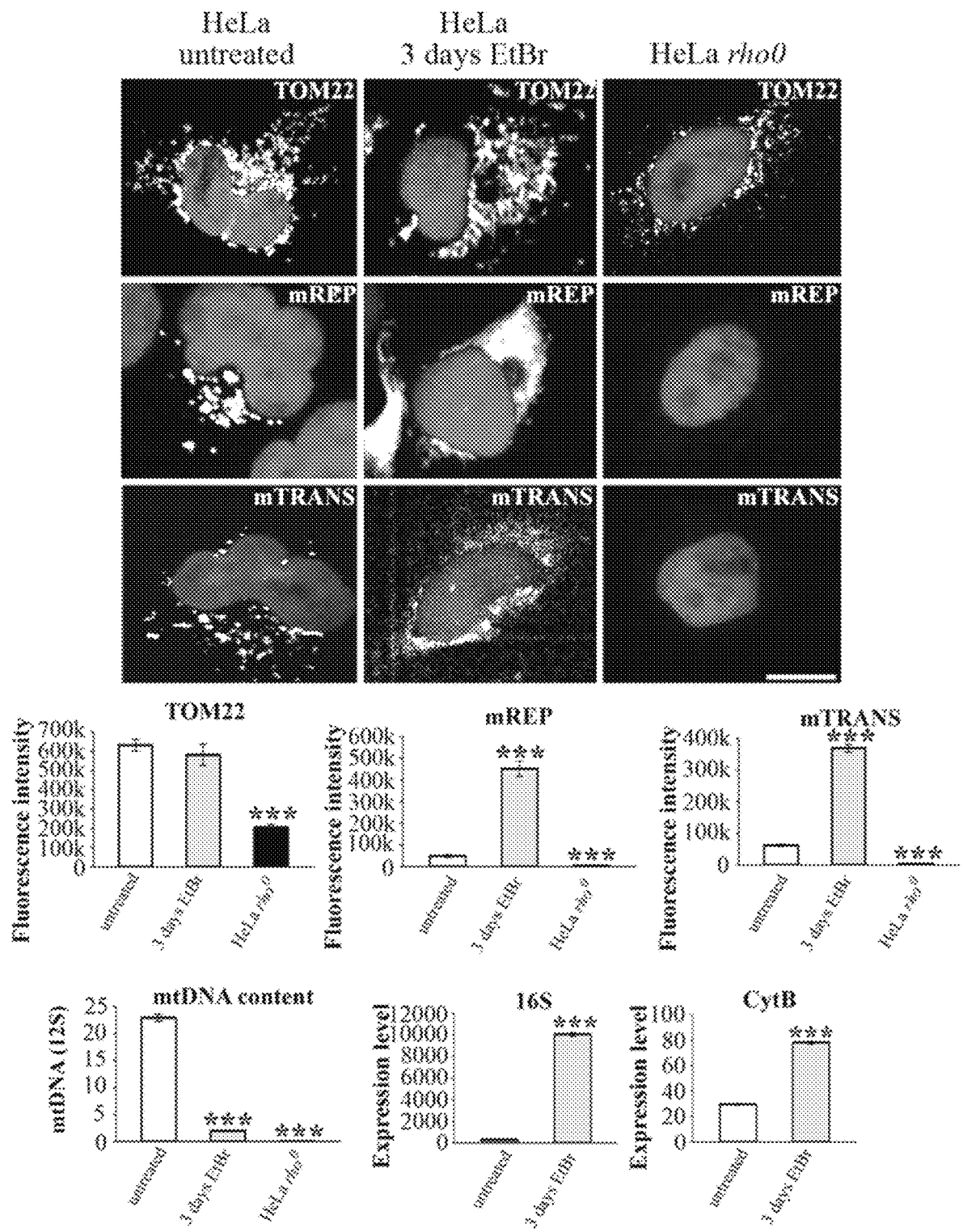
Figure 16B:
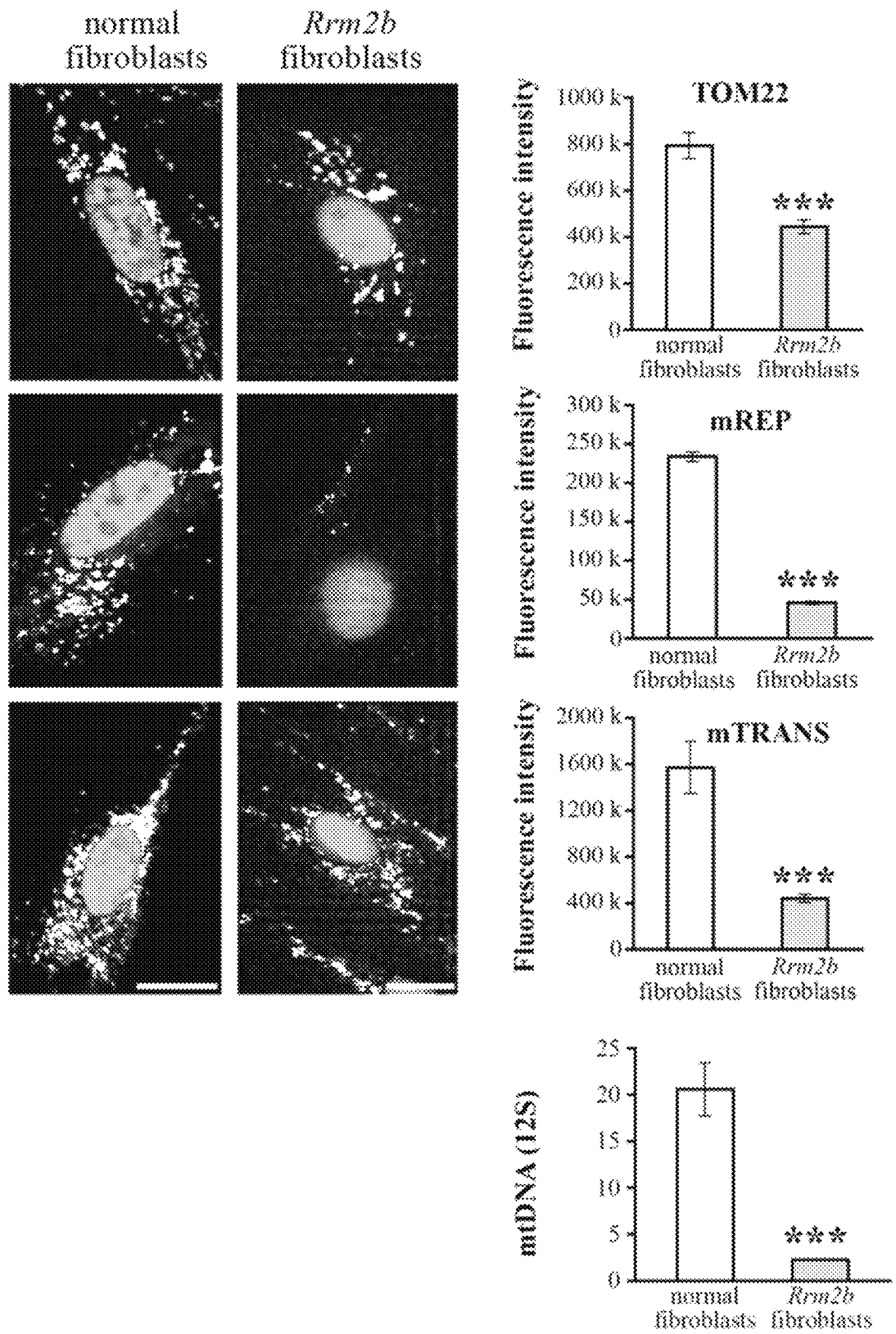

FIGS. 16A and 16B. mTRIP detects mtDNA processing alterations in cells with perturbed mtDNA content. (A) Upper panels: 3D-reconstructed HeLa cells analysed by 3D-FISH/mTRIP with probes mREP and mTRANS and by immunofluorescence with TOM22 (colour indicated on each panel). Cells were either untreated or treated with EtBr for 3 days to decrease their mtDNA content. Note significant variation in distribution and aspect of mREP and mTRANS labelling in these cells compared to untreated cells. HeLa rho⁰ cells were also analysed. Scale bar=10 μm. Fluorescence intensity quantification is shown in lower panels; n=30, three independent experiments. mtDNA content of cells analysed by qPCR in the 12S region, and expression levels of 16S and CytB RNAs analysed by RT-qPCR are shown. T-test for treated or mutated cells versus untreated cells, (***) p≤0.001. (B) 3D-reconstructed normal human primary fibroblasts (IMR-90) and fibroblasts from a patient with mutated Rrm2b analysed by mTRIP with probes mREP and mTRANS, and by immunofluorescence with TOM22. Results similar to IMR-90 were obtained with two other types of human primary fibroblasts (not shown). Scale bar=00 μm. Fluorescence intensity quantifications are shown on right; n=30, three independent experiments. Quantification of the mtDNA content (12S region) by qPCR is shown below.

Figure 17A:
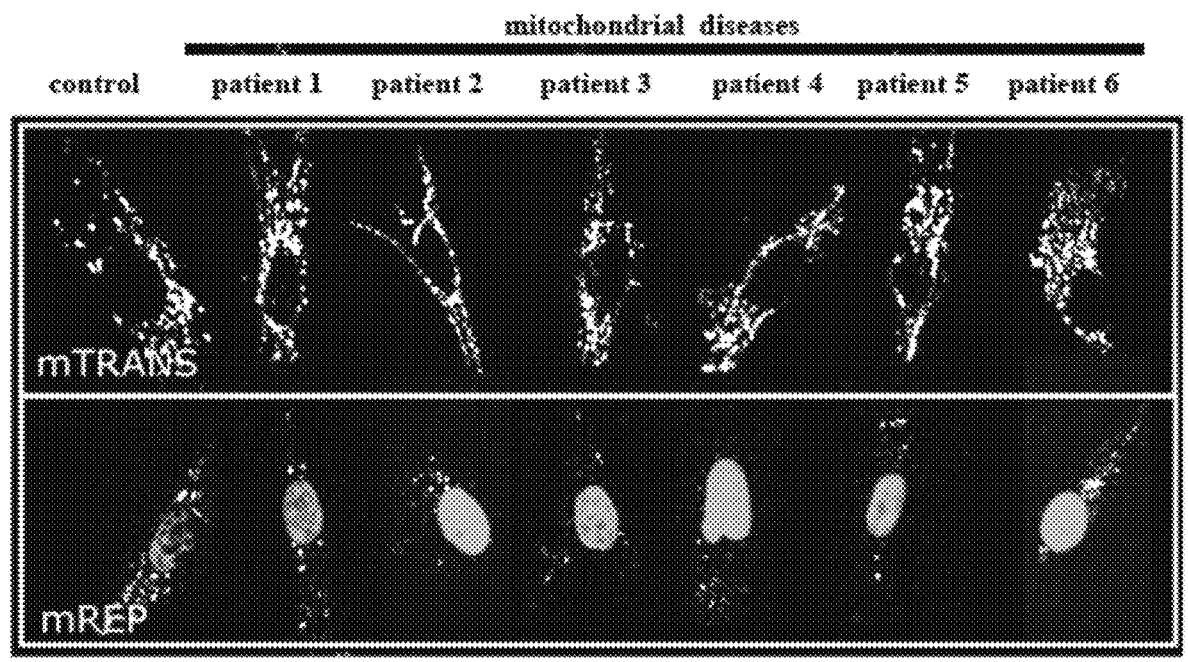
Figure 17B:
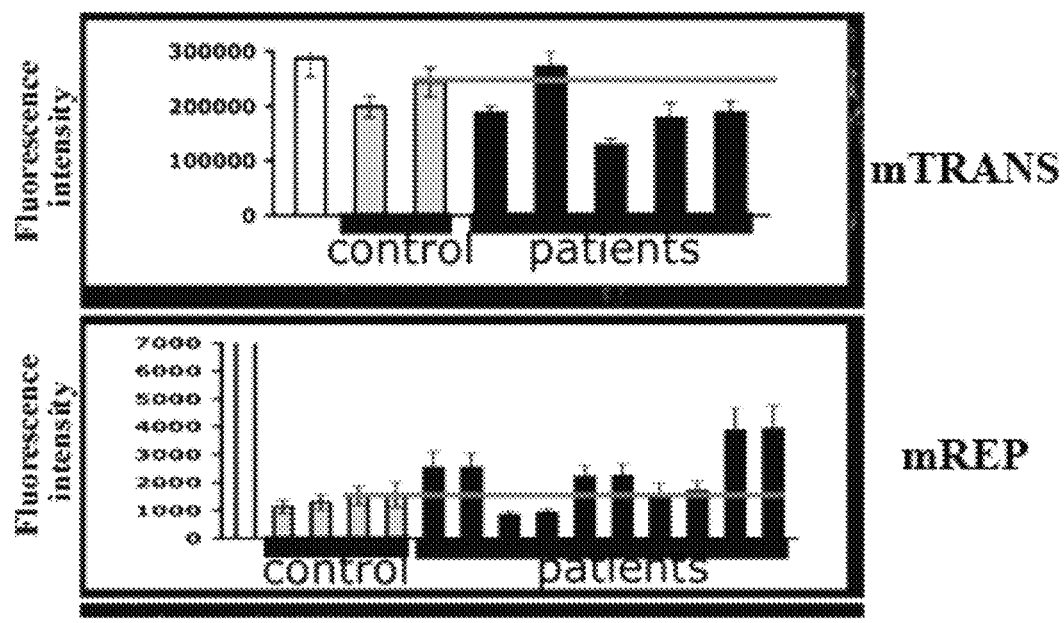

FIGS. 17A and 17B. Assays on patients with mitochondrial diseases. (A) mTRANS and mREP labelling on primary fibroblasts from patients with mitochondrial diseases (mtDNA depletion syndromes). Nuclei (blue) are labelled by Hoechst (only with probe mREP) (B) Fluorescence intensity quantification of mTRANS ans mREP labelling in fibroblasts from a few normal individual (control) and from patients with mitochondrial diseases (mtDNA depletion). The red line indicates the value of corresponding to the average controls. Note that in spite all these patients display severe mtDNA depletion, various levels of mTRANS and mREP are detected, indicating that mitochondria in some patients have regular mtDNA transcription and initation of replication activities, whereas in other patients one or both of these activities are reduced or increased. Thus reduced levels of mtDNA do not necessarily imply reduced mtDNA processing activity in disease, a notion that might be linked to the extent and/or the progression of the disease.

18A and 18B. Assays on patients diagnosed with progeria-related syndromes, and not diagnosed as mitochondrial diseases. (A) mREP labelling (red) on primary fibroblasts from patients with progeria-related syndromes, but that were of diagnosed as mitochondrial disease or mitochondrial-related diseases. Fibroblasts form healthy individuals (control) and from a syndrome of sensitivity to UV that is not associated with progeria are also shown. Nuclei (blue) are labelled by Hoechst Scale bar=10 μm. (B) Fluorescence intensity quantification of mREP labelling. The red line indicates the value corresponding to average controls. T-test compared to controls, (*) p≤0.01; (***) p≤0.001. Note that mREP labelling is reduced or increase in the moderate and severe progeria, respectively. Thus, diseases that are not not identified for mitochondrial impairment reveal affected mitochondrial function by mREP labelling.

FIGS. 19A to 19D. Assays on human cells on long-term treatment with AZT. HeLa cells were treated with AZT from 1 to 15 days. Several parameters were analysed at the indicated time points: (A) mitochondrial mass by TOM22 immunolabeling; (B) mtDNA content by qPCR; (C) mREP, and (D) mTRANS. T-test compared to untreated controls. A star indicate p<0.01-0.001. Note that after treatment with AZT, in spite of low or no variation in the mitochondrial mass and in mtDNA content, mREP and mTRANS values are dramatically reduced from the first day of treatment. Thus, mREP/mTRANS labelling indicates affected mitochondrial function, even when classical mitochondrial parameters have similar or slightly affected values compared to controls.

Figure 20A:
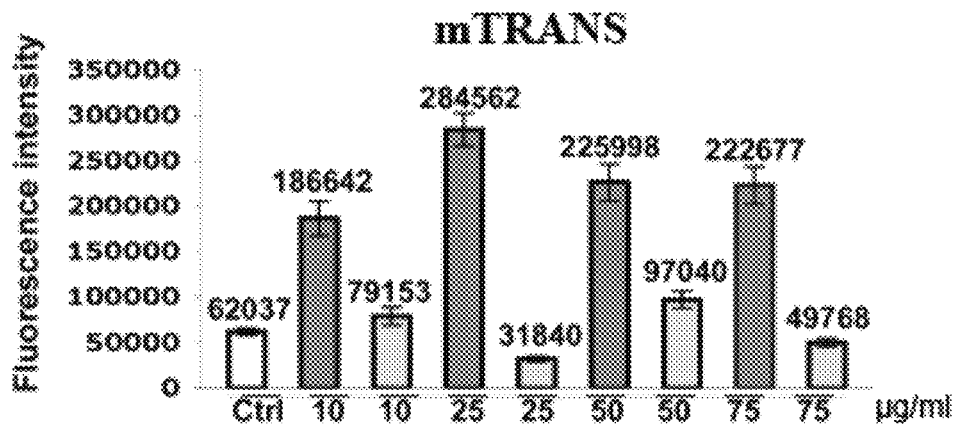
Figure 20B:
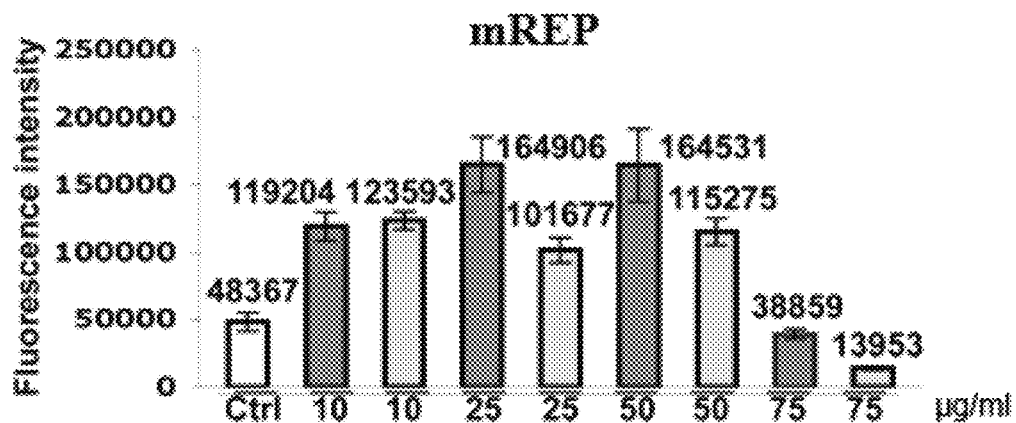

FIGS. 20A and 20B. Assays on cells treated with rifampicin. HeLa cells were treated for 24 h with rifampicin at the indicated concentrations. Rifampicin was dissolved in DMSO. Pink columns indicate experiments performed in the presence of rifampicin, and green column in the presence of equivalent amounts of DMSO-containing buffer. White columns indicate untreated controls. (A) mTRANS and (B) mREP labelling. Note variations in the levels of mTRANS and mREP at different concentrations of rifampicin, associated or not with variations in the presence of buffer alone. This experiment indicates that treatments with potential cytotoxic effect (increasing cell mortality was observed with increasing concentration of rifampicin, not shown) affect mtDNA processing. Alterations of mTRANS and/or mREP values are detected at low doses of rifampicin.

Figure 21A:
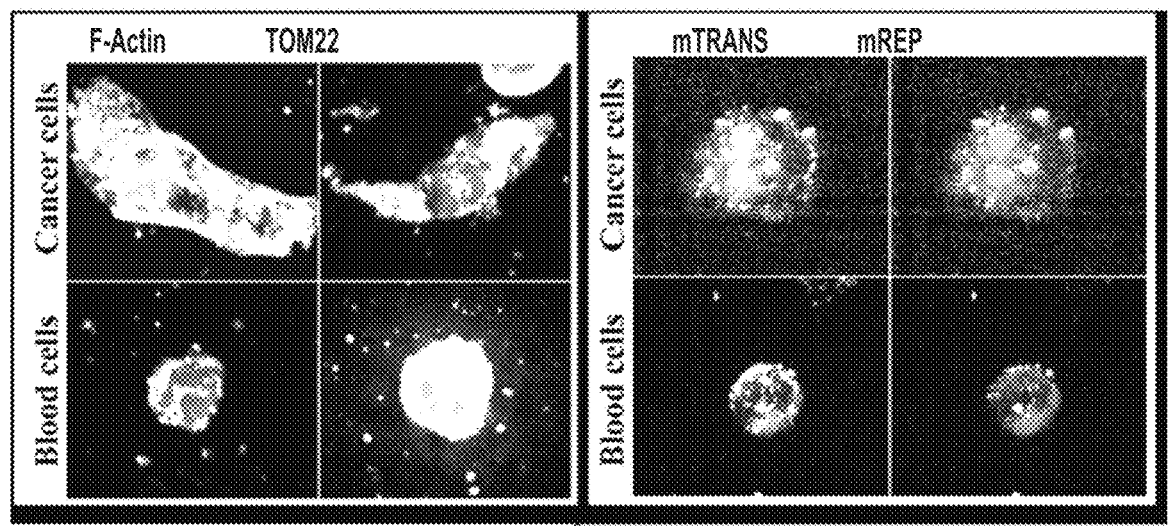
Figure 21B:
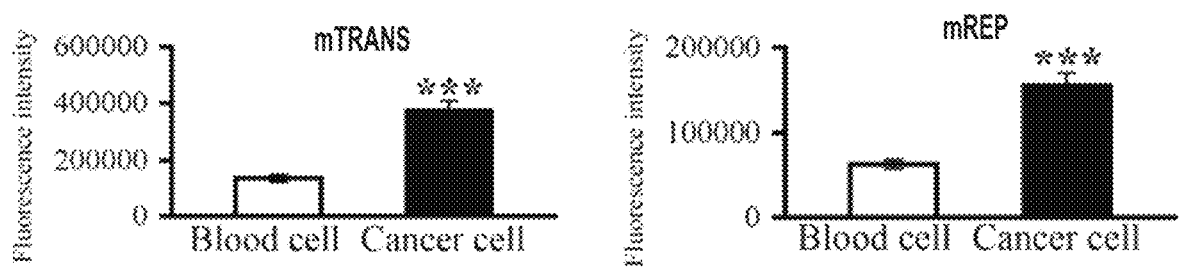

FIGS. 21A and 21B. Assays on patients diagnosed with cancers. (A) Labelling of isolated cancer cells and normal blood cells. Left panels: labelling of the cytoskeleton (F-Actin, red, by rhodamine-phalloidine) and of the mitochondrial mass (TOM22 immunostaining). Right panels: mTRANS and mREP labelling. (B) Fluorescence intensity quantification of mTRANS and mREP. Note the higher levels of mTRANS and mREP labelling in cancer versus normal cells. However normal cells (from blood) were smaller in size, and had a especially reduced cytoplamsic mass, compared to that cancer cells tested here. When different cell types are compared, values of mTRANS/mREP should therefore be analysed taking into account also the cell size and the mitochondrial mass.

Figure 22:
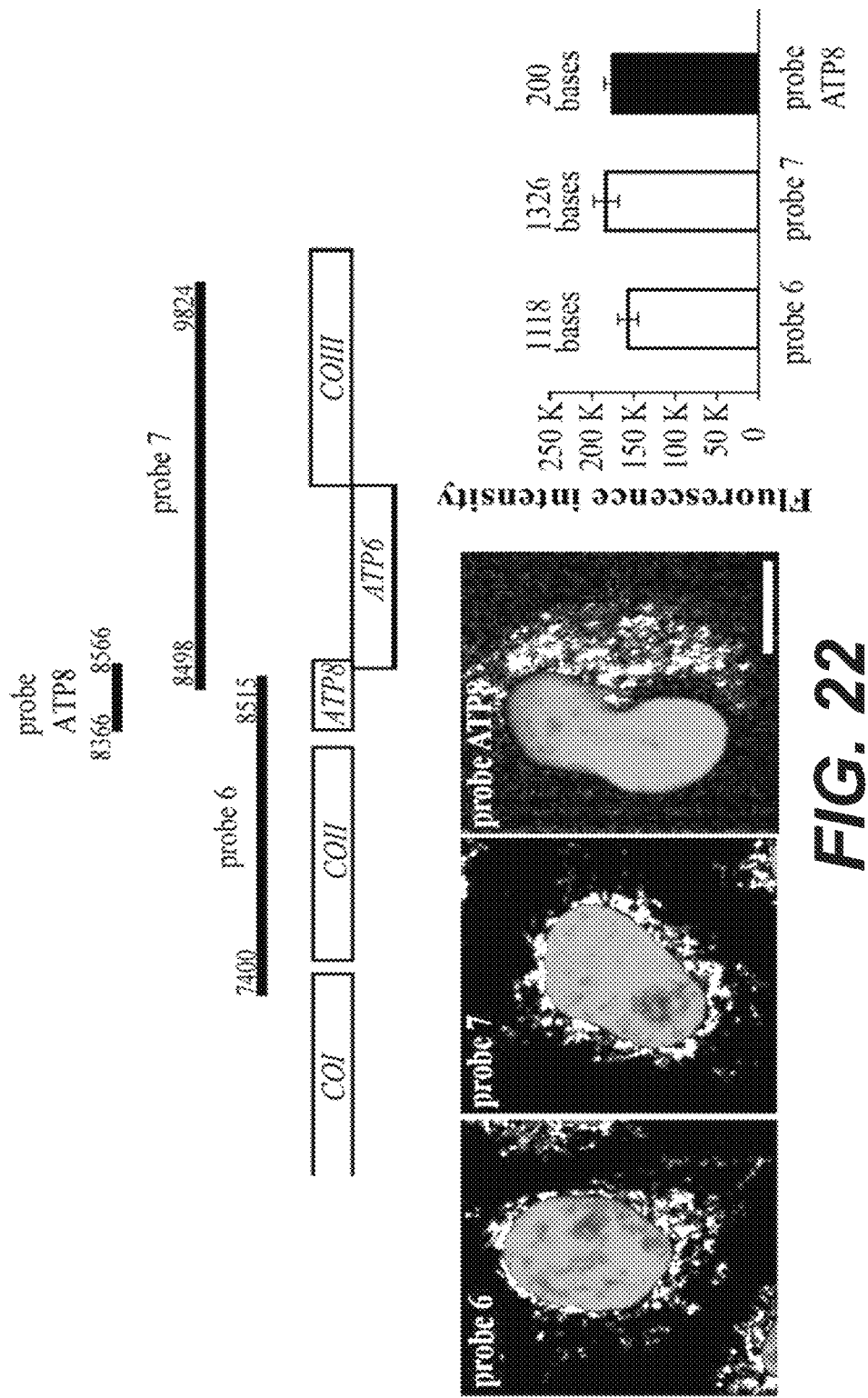

FIG. 22. Efficiency of the 3D-FISH/mTRIP method of the invention is not affected by the size of the probe: Upper panel: schematic representation of the position of the probes (with the mitochondrial coordinates) and of the genes present in the region tested; tRNAs are not represented. Mitochondrial coordinates according to MITOMAP (http://www.mitomap.org/MITIMAP). Lower panels: mTRIP FISH labelling of HeLa cells with the indicated probes (red). Nuclei (blue) are labelled with Hoechst. Scale bar=10 μm. On the right, fluorescence intensity quantification of 3D-reconstructed cells. n=30; three independent experiments. T-test, did not show significant differences between the samples.

FIG. 23. RT-qPCR and qPCR primers. The sequence of forward and reverse primers for RT-qPCR (upper panel) and qPCR (lower panel) is indicated after the name of the probe that also indicates the gene analysed. Number in parenthesis indicate different sets used to test the same gene. The pair A-B1 amplifies a mtDNA region included in 7S, while the pair A-B2 amplifies a region beyond 7S in the direction of the H-strand. Reference is indicated in the last column.

EXAMPLES

A. Materials and Methods

Cells and Culture Conditions.

Human HeLa cells and IMR90 primary fibroblasts (purchased from ATCC) were grown in MEM medium with 10% foetal bovine serum (FBS), HeLa rho° cells in DMEM medium with 10% FBS 1 mM sodium pyruvate and 0.2 mM uridine, at 37° C. and in the presence of 5% CO2. Cells cultures were split at regular intervals for different experiments as required. IMR-90 cells were at passage 15. Culture under low oxidative stress were treated with 50 μM H2O2 for the time indicated.

Reagents and Antibodies.

BrdU, anti-TOM22 Atto488, and Hoechst 33342 were purchased from Sigma; anti-BrdU antibody from BD Biosciences; MitoTracker® Green FM, and secondary antibodies (Goat anti-mouse antibodies and Goat anti-rabbit antibodies Alexa® Fluor 555 or Alexa® Fluor 488 conjugated) were purchased from Invitrogen.

Immunofluorescence (IF).

Cells plated on slides were fixed with 2% PFA and permeabilized with 0.5% Triton X-100. The slides were incubated in blocking buffer (BSA 5%; PBS 1×) for 1 hr then with the primary antibody for 1 hr. A secondary anti-mouse or anti-rabbit antibody Alexa® Fluor 555 or Alexa® Fluor 488 conjugated was applied. The DNA was stained with 10 μg/ml Hoechst 33342 and the image analysis was carried out using Perkin-Elmer Ultraview RS Nipkow—spinning disk confocal microscope. For MitoTracker analysis, 200 nM MitoTracker® Green FM were added to fixed/permeabilized cells and incubated for 1 hr.

Probe Labeling and Denaturation.

The DNA probes for FISH were labeled by nick translation of PCR products, incorporating Atto425-dUTP, or Atto488-dUTP, or Atto550-dUTP, using commercial kit (Atto425/Atto488/Atto550 NT Labeling kit, Jena Bioscience). 40 ng of labeled probes were mixed with 400 ng of sonicated salmon sperm DNA (Sigma) and hybridization buffer (50% formamide, 10% dextran sulfate, in 2×SSC pH 7.0). The hybridization mix was denatured at 80° C. for 10 min then kept at 37° C. for 30 min.

Modified 3D-FISH and 3D-FISH Coupled IF.

Cells plated on slides were fixed with 2% PFA and permeabilized with 0.5% Triton X100. Cells were then incubated in 50% formamide (pH=7.0)/2×SSC for 30 min at RT, and denaturated in 70% formamide/2×SSC for 5 min at 75° C. Hybridization was done with 40 ng of probe (single probe or mix) for 16 hrs at 37° C. After washing the slides in 2×SSC, 1×SSC then 0.1×SSC, the DNA was stained with 10 μg/ml Hoechst 33342, and 40 ng of probe (single probe or mix) and the image analysis was carried out using spinning-disk Perkin Elmer confocal microscope. Experiments at saturation were performed with 200 ng of probe. When required, fixed/permeabilized cells on slides were treated with RNAseA (100 μg/ml, Roche), or RNAseH (100 U/ml, NEB) or DNAseI (100 U/ml, Invitrogen) for 1 hr at 37° C. When more than one nuclease were used, the enzymes were either added simultaneously or the second nuclease was added after incubation with the first nuclease, followed by three washes with PBS, and further incubation for 1 hr at 37° C. For 3D-FISH coupled IF, after hybridizaton and 0.1×SSC wash, the immunofluorescence procedure was applied.

BrdU Incorporation.

Cells plated on slides were incubated for 10 min in the presence of 100 μM BrdU, then immediately fixed in 2% PFA (10 min), treated for 10 min with 4N HCl and 0.5% Triton X-100, and neutralized for 30 min by 100 mM sodium borate. Cells were blocked in 5% BSA in PBS and permeabilized with 0.5% Triton X100[26]. BrdU was detected by immunostaining with anti-BrdU antibody. The DNA was stained with 10 μg/ml Hoechst 33342, and the image analysis was carried out using spinning-disk Perkin Elmer confocal microscope.

FISH Coupled BrdU.

Cells plated on slides were fixed with 2% PFA and permeabilized with 0.5% Triton X100. Denaturation was performed using buffer containing 10 mM Tris HCl pH 8.0, 50 mM KCl, 5% glycerol at 95° C. for 8 min. The slides were washed in 0.1×SSC and series dehydrated in 70%, 90%, and 100% ethanol and finally air-dried[27]. Hybridization was done overnight at 37° C. After washing the slides in 2×SSC then 0.1×SSC, the slides were incubated in blocking buffer (BSA 5%; PBS 1×) for 1 hr, then incubated with mouse anti BrdU antibody for 1 hr. A secondary anti-mouse antibody Alexa® Fluor 555 or Alexa® Fluor 488 conjugated was applied. The DNA was stained with 10 μg/ml Hoechst 33342 and the image analysis was carried out using spinning-disk Perkin Elmer confocal microscope.

Confocal Acquisition, 3D-Reconstruction and Quantification.

Confocal acquisitions were performed using a spinning-disk Perkin-Elmer Ultraview RS Nipkow Disk, an inverted laser-scanning confocal microscope Zeiss Axiovert 200M with an Apochromat 63×/1.4 oil objective and a Hamamatsu ORCA II ER camera (Imagopole, PFID, Institut Pasteur). Optical slices were taken every 200-nm interval along the z-axis covering the whole depth of the cell, at resolution of 1.024/1.024 pixels. Three-dimensional reconstruction was achieved using the IMARIS software (Bitplane). Fluorescence quantification was done using a single-imaging frame collection and ImageJ 1.34-s software (post-acquisition analysis). The perinuclear location of FISH-labelled organelles corresponds to mitochondria located within 2 |im from the nuclear surface. The percentage of perinuclear 3D-FISH mitochondria was calculated on the total 3D-FISH labelling. Quantification of mREP-positive and mREP-negative mitochondria was performed on either Polγ or TFAM immuno-labeled areas. For each condition, 300 samples of identical surface were analysed. Co-localization studies were done with ImageJ JACoP plug-in[28].

Statistical Analysis.

The significance of differences between data was determined using Student's t test for unpaired observations.

RT-qPCR.

Total RNA was isolated from HeLa cells and IMR90 primary fibroblasts using a RNAeasy Mini kit (Qiagen) and a RNAeasy Micro kit (Qiagen), respectively. The total RNA was treated with DNaseI (Qiagen), then reverse-transcribed using Superscript® III Reverse transcriptase (Invitrogen). Real-time quantitative PCR was performed using Power Sybr Green PCR Master Mix (Applied Biosystems) and the rate of dye incorporation was monitored using the StepOne™ Plus RealTime PCR system (Applied Biosystems). Three biological replicates were used for each condition. Data were analyzed by StepOne Plus RT PCR software v2.1 and Microsoft excel. TBP transcript levels were used for normalisation of each target (=ΔCT). Real-time PCR CT values were analyzed using the $2^{-\Delta\Delta C_t}$ method to calculate the fold expression ($\Delta$ ($\Delta^2$CT)method)[29]. Custom primers were designed using the Primer3Plus online software (http:// www.bioinformatics.nl/cgi-bin/primer3plus.cgi). Primers used for amplification are available upon request.

B. Results

Identification of Mitochondrial Subpopulations by Improved FISH (mTRIP)

To gain insight into the dynamics of mitochondrial DNA and RNA inside the organelle, the inventors have developed a novel approach called mTRIP (Mitochondrial Transcription and Replication Imaging Protocol) that labels simultaneously DNA and RNA, especially mtDNA and mtRNA in human cells, by improving fluorescence in situ hybridization (FISH), and performed 3D confocal acquisitions (3D-FISH). mTRIP is a combination of DNA FISH and RNA FISH techniques, and it limits the use of potentially damaging agents for macromolecules. Since proteins are not destroyed during this treatment, and in contrast to existing protocols, 3D-FISH have been coupled to immunofluorescence (FIG. 1. D-G). Hence, it was possible for the first time to monitor, in particular quantatively monitor, mitochondrial DNA, RNA and proteins simultaneously. Moreover, the intensity of fluorescence could be quantified, thereby permitting a relative assessment of these nucleic acids with single-cell resolution.

TOM22, a subunit of the mitochondrial outer membrane translocase (Yano et al. 2000) which is uniformly distributed in mitochondria, is used here as an indicator of mitochondrial mass. In this context, mitochondria are visualised as individual units or structured in the interconnected mitochondrial network (FIG. 1 H). Colabelling of mTRIP probes with TOM22 immunofluorescence (IF) was performed to assess the distribution of FISH labelling in mitochondria. We observed that mTOT, a mixture of 14 probes that cover the entire mitochondrial genome (Table 1) labelled only a fraction of the mitochondrial network in human cells (FIG. 1 I). This labelling with mTOT marked small structures within the mitochondrial mass suggesting that they might represent nucleoids (see below).

Figure 1A:
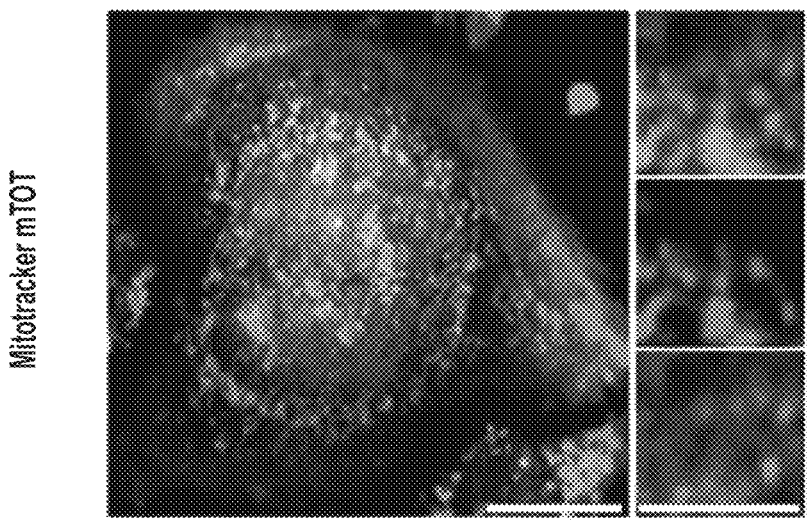
FIGS. 1A to 1K. A modified 3D-FISH/mTRIP method reveals a perinuclear mitochondrial subpopulation. Efficiency and characteristics of mTRIP labeling is also disclosed (A) 3D reconstruction of a dividing HeLa cell shows perinuclear distribution of the mitochondrial subpopulation labeled with the mt DNA probe mix mTOT (red). The entire mitochondrial network is labeled with MitoTracker (green) and the nucleus with Hoechst 33342 (blue). On the right, magnification shows MitoTracker labeling (bottom), mTOT (middle) and merge (top). Scale bar=10 um. Zoom scale bar=3 um. (B) 3D FISH-reconstructed HeLa cells labeled with the mTOT probe (red), with or without nuclease treatment (specified on the top of each panel; the arrow indicates that the second nuclease was added after 1 h incubation with the first nuclease). Scale bar=10 um. (C) Fluorescence intensity quantification of mTOT, with or without nuclease treatment, indicated on the X-axis ("then" indicates that tof he second nuclease was added after 1 h incubation with the first nuclease) n=30. T-test, compared to untreated cells, (*) p<0.05; () p<0.01; (*) p<0.001. (D-G) Epitope conservation during mTRIP treatment for relevant antibodies used in this study. (D) Anti-TOM22 immunostaining and (E) fluorescence intensity quantification of HeLa cells treated as indicated, or untreated, before immunolabelling. IF: immunofluorescence; steps 1+2: permeabilization+incubation with formamide 50%; step 3: denaturation in 70% formamide; mTRIP: complete procedure. A mild treatment with proteinase K (5 min at 37° C.) was used as control of protein degradation; this reatment does not completely degrade proteins (not shown) and is thus compatible with fluorescence labelling. Fluorescence intensity quantification of (F) Polγ and (G) TFAM immunostaining of HeLa cells pre-treated with the complete mTRIP protocol, or untreated. (H) Scheme for 3D analysis of immunolabelled cells. Confocal acquisition, 3D-reconstruction and quantification (see Methods). TOM22 immunolabelling was used to define the mitochondrial mass. The same procedure was also used for the labelling of mtDNA probes by mTRIP. (I) mTRIP labels mitochondrial RNAs and DNA: 3D-reconstruction of a HeLa cell shows the mitochondrial fraction labelled with the mtDNA probe mix mTOT (red). The mitochondrial network is labelled with TOM22 by immunofluorescence (green) and the nucleus with Hoechst (blue). Below, 2.5× magnification of mTOT (left), and merge (right). Scale bar=10 μm. (J) 3D-reconstructed cells labelled with mTOT in presence or absence of proteinase K treatment. The other key FISH probes used in this work, mTRANS and mREP (which labels only transcripts and DNA, respectively, as described below in the text) were also tested. (K) Fluorescence intensity quantification of mTOT, mTRANS, and mREP, with or without proteinase K treatment; for each condition n=30, three independent experiments. T-test, compared to untreated cells (***) p≤0.001.
Figure 1B:
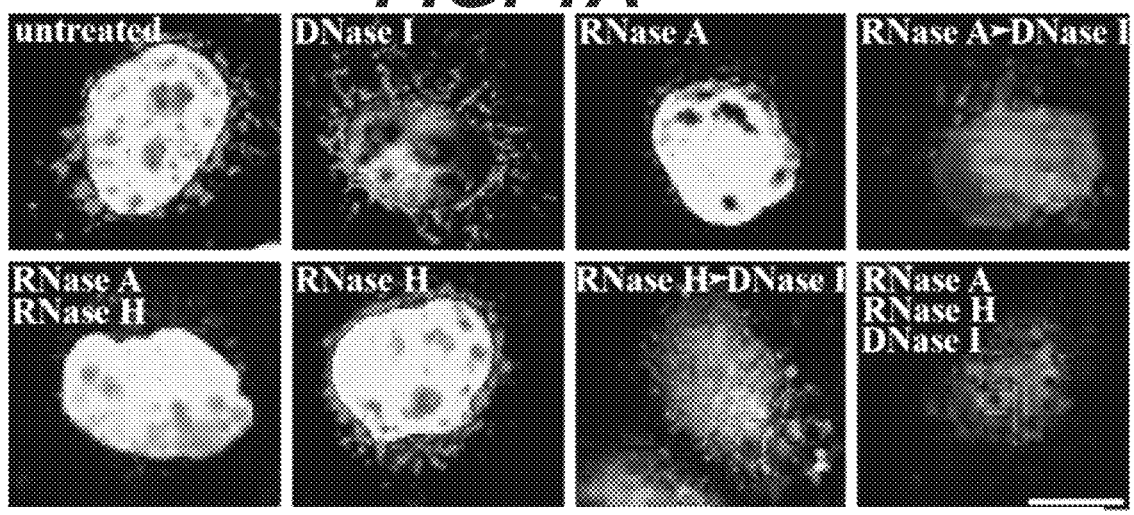
Figure 1C:
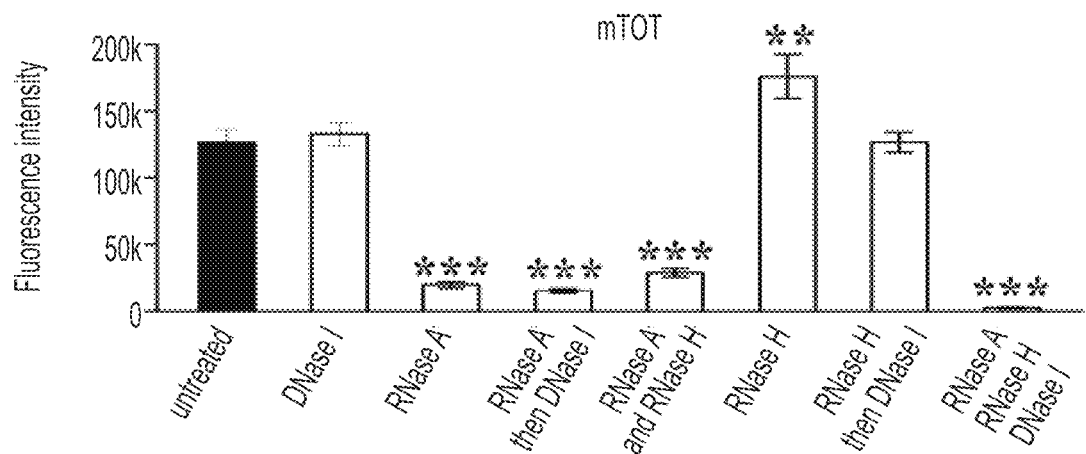
Figure 1D:
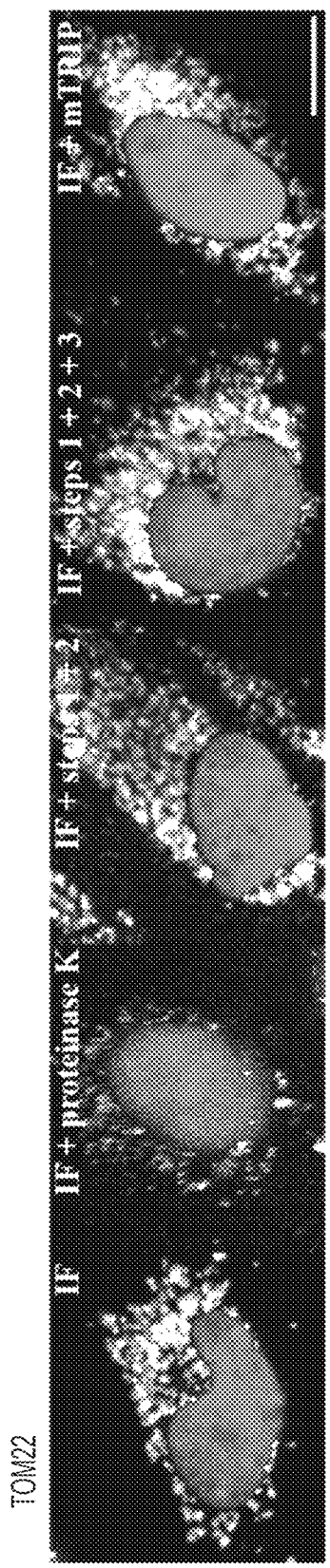
Figure 1E:
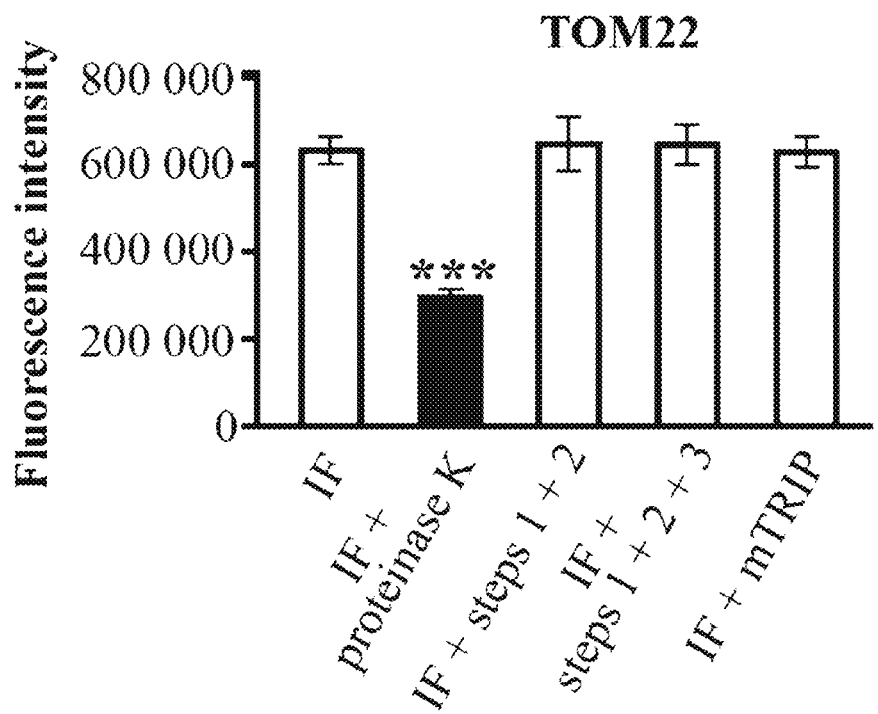
Figure 1F:
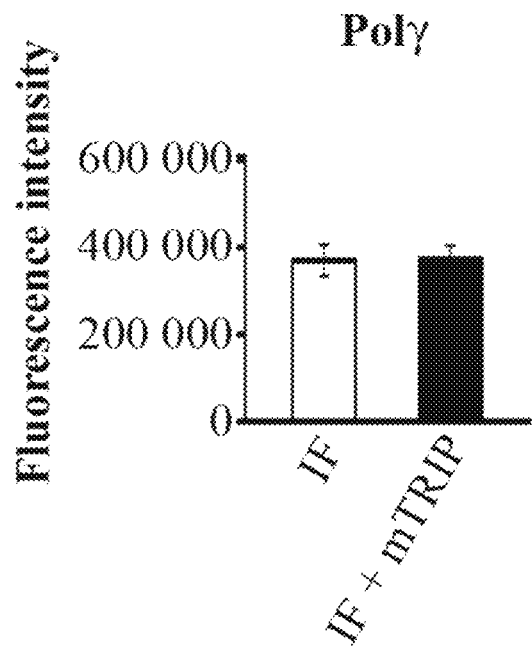
Figure 1G:
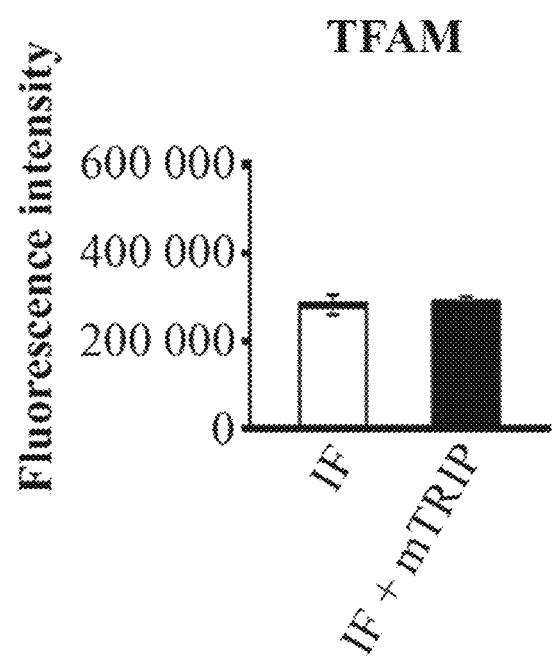
Figure 1H:
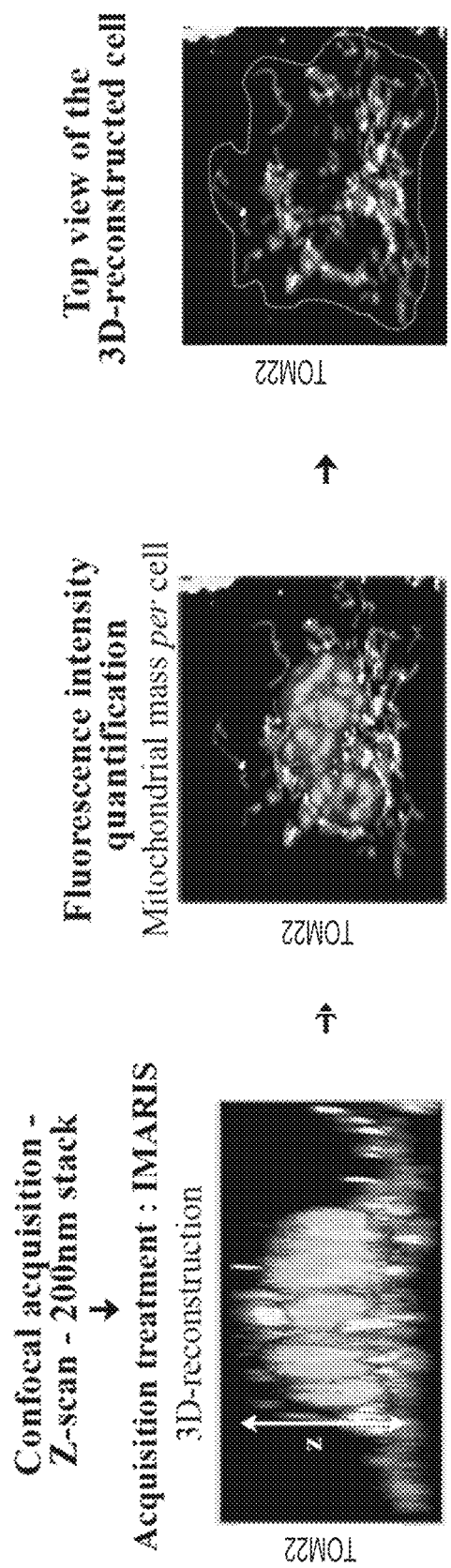
Figure 1I:
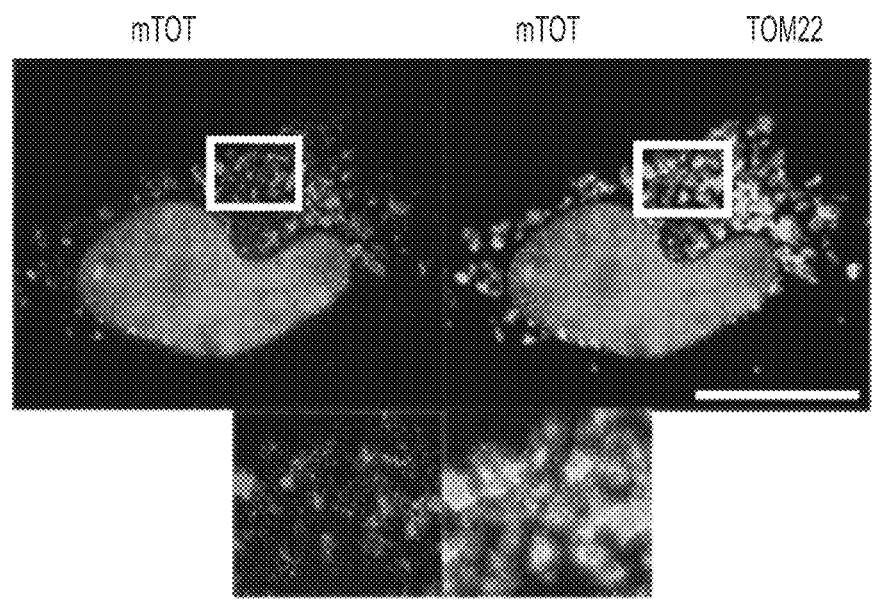
Figure 1J:
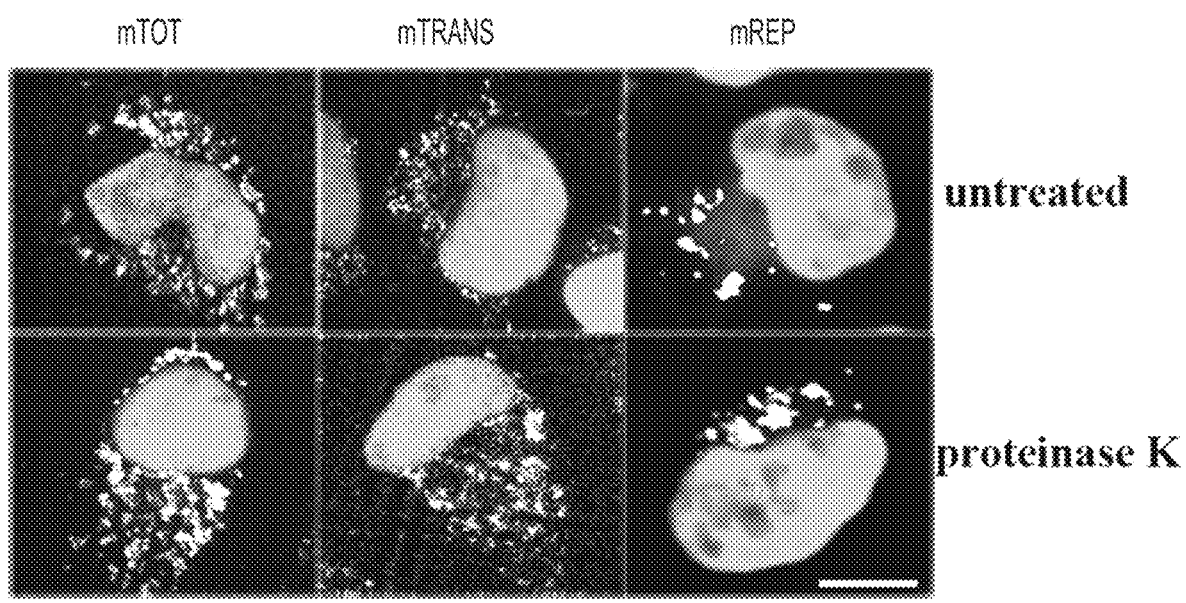
Figure 1K:
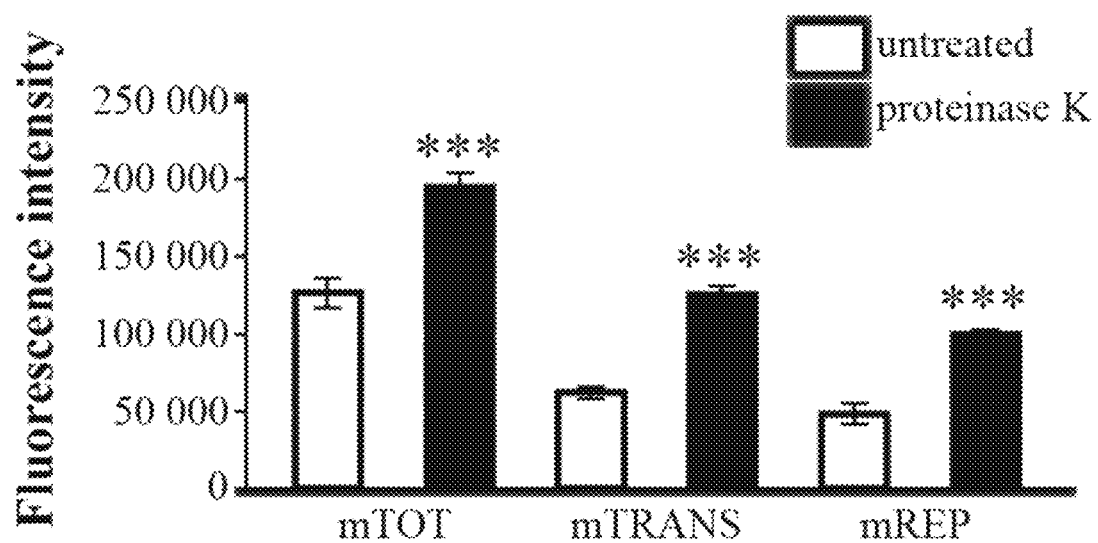

Strikingly, 3D-FISH revealed that the labelling occurred in a distinct fraction of mitochondria, located predominantly in the perinuclear region in single human HeLa cells (FIG. 1a; 77.78%±1.72% of labelled mitochondria are located within 2 μm from the nuclear border). This result was intriguing since the inventors used probes that cover the entire 16.5 kbp of the mitochondrial genome (mixture of equimolar amounts of 14 probes, called mTOT, Tables 1-2) and expected all mitochondria to be labelled. Treatment of cells with either DNaseI, RNaseA or RNaseH (specific for DNA-RNA hybrids), and combinations of these specific nucleases before hybridization with the mTOT probes showed that 84% of labelling targets RNA, corresponding to the missing signal in the presence of RNaseA (FIG. 1 b, c). Moreover, about 23% of labelling corresponded to DNA and/or structured RNA since it was resistant to combined RNaseA and RNaseH treatment. These values cumulated exceed 100% since treatment with some nucleases increases the intensity of labelling, see below. Interestingly, the higher intensity of fluorescence observed in the presence of RNaseH (1.4-fold compared to untreated cells) revealed that removal of the RNA moiety from RNA-DNA hybrids made DNA available for pairing with the fluorescent probe. These hybrids probably correspond to transcripts bound to their DNA template. Treatment of samples with RNaseH and subsequently with DNaseI restored the fluorescence levels of untreated cells (FIG. 1c), confirming that the DNA portion of RNA-DNA hybrids paired with the fluorescent probe after disruption of the RNA moiety. The latter observation, and the apparent absence of effect of the DNaseI treatment, indicated that mtDNA is available in limited amounts for binding with fluorescent probes, unless it is engaged in a local open structure.

Treatment with proteinase K prior to mTRIP resulted in a large increase in the signal (154% for mTOT, 206% for mTRANS and 202% for mREP, FIGS. 1, J and K; the last two probes recognize RNA and DNA, respectively, see below) compared to untreated cells, indicating that some mtRNA and mtDNA were inaccessible to the probes because they could be bound to, or masked by proteins (FIG. 1, J-K). In spite of this increase in signal intensity, proteinase K treatment was avoided here because mTRIP was frequently coupled to immunofluorescence for the detection of proteins.

TABLE 1

Coordinates of the probes. The start and end points of probes used for FISH experiments are given on the mitochondrial DNA (NC_012920.1, NCBI or GenBank or MITOMAP accession number, was used as reference). Individual probes are indicated in the upper panel. Mix of more than one probe and their composition are indicated in individual panels below. All probes are oriented in the direction of transcription of the H strand, with the exception of probe ND6 that is in the inverse orientation (transcription on the L strand).

Figure 5A:
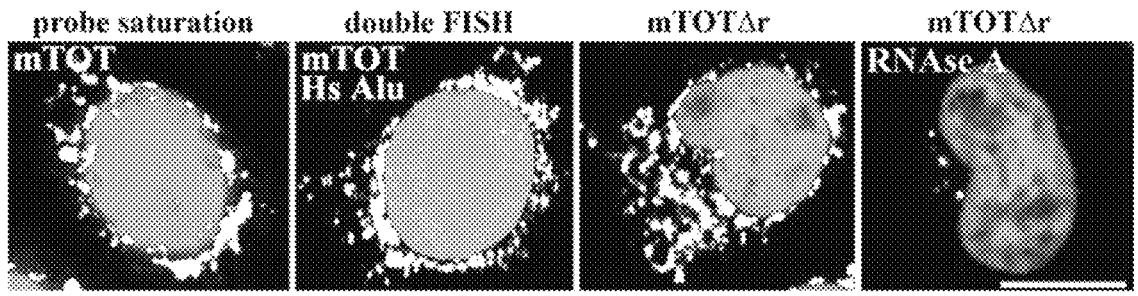
FIGS. 5A to 5B. Characterization of the 3D-FISH labeling (A) 3D-FISH/mTRIP reconstructed HeLa cells labeled with: the mTOT probe (red) at saturating concentrations (200 ng; left panel); co-FISH of mTOT probe (red) and of the Hs Alu probe, for the human nuclear Alu sequence, (green) (middle left panel); mTOTΔr, that consists in mTOT without probes 1, 2, and 14 that cover the mt ribosomal genes, untreated (middle right panel), and treated with RNAse A (right panel). Scale bar=10 um. (B) Fluorescence intensity quantification of mTOT and mTOTΔr with and without nuclease treatment. n=30 from three independent experiments; T-test, compared to untreated cells, (*) p<0.05; () p<0.01; (*) p<0.001.
Figure 5B:
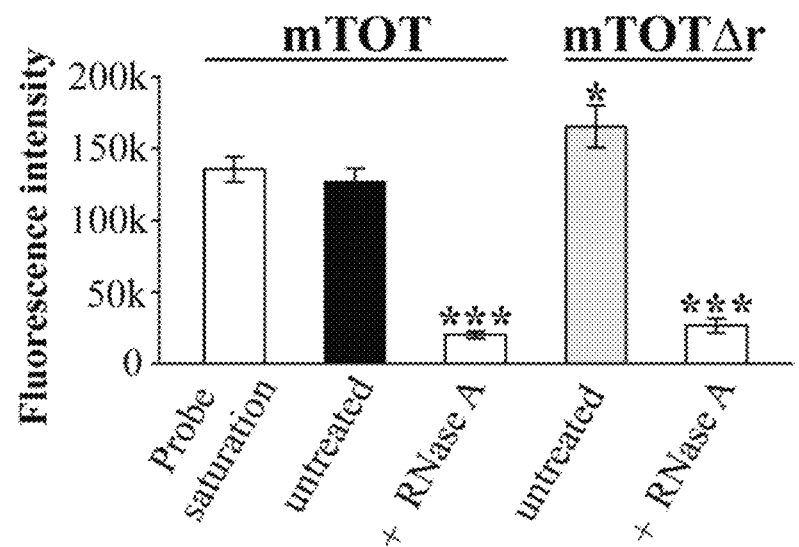

| Probe | start | end | size |
|---|---|---|---|
| 1 | 1905 | 2866 | 961 |
| 2 | 2842 | 3554 | 712 |
| 3 | 3451 | 4825 | 1374 |
| 4 | 4805 | 6129 | 1324 |
| 5 | 6032 | 7420 | 1388 |
| 6 | 7400 | 8518 | 1118 |
| 7 | 8498 | 9824 | 1326 |
| 8 | 9804 | 11190 | 1386 |
| 9 | 11107 | 12618 | 1511 |
| 10 | 12513 | 13517 | 1004 |
| 11 | 13416 | 14836 | 1420 |
| 12 | 14805 | 16055 | 1250 |
| 13 | 15778 | 600 | 1376 |
| 14 | 501 | 2024 | 1523 |
| 13-1 | 16034 | 521 | 1041 |
| 14-1 | 650 | 1598 | 949 |
| ND1 | 3515 | 3715 | 200 |
| ATP8 | 8366 | 8566 | 200 |
| ND6 | 14658 | 14180 | 479 |
| mREP | 446 | 544 | 98 |
| PH-1-2 | 546 | 746 | 200 |
| PL-OH | 225 | 425 | 200 |
| 7S | 16366 | 16566 | 200 | mTRANS probes 2, 6, 11
mTOT probes 1 to 14
mTOTΔr probes 3 to 13 (rRNA probes excluded)
human mt genome size: 16568 bp 3D-FISH/mTRIP Labels Transcript Profiles of Mitochondria To investigate the nature of the mitochondrial subpopulations revealed by this approach, the inventors have performed FISH with each of the single 14 probes that were combined in mTOT, in the presence and in the absence of DNAseI or RNAseA. The inventors have observed that each probe recognized a specific subset of mitochondria and not the entire mitochondrial network (FIG. 2a), indicating that not only the intensity but also the distribution of the subset of the labeling varied as a function of the mtDNA region tested. It further indicated that only a subpopulation of mitochondria carries detectable amounts of the target nucleic acid, and that mitochondria may not be functionally alike. Saturation experiments indicated that labelling of a subset of mitochondria was not due to limited concentrations of probe (FIG. 5). Treatment with nucleases (DNAseI or RNAseA) showed that all of the probes recognized essentially RNA targets, with the exception of probes 4, 8 and 13, which also recognized DNA (decrease in fluorescence following treatment with DNAseI of 65%, 97% and 47%, respectively).

Figure 2A:
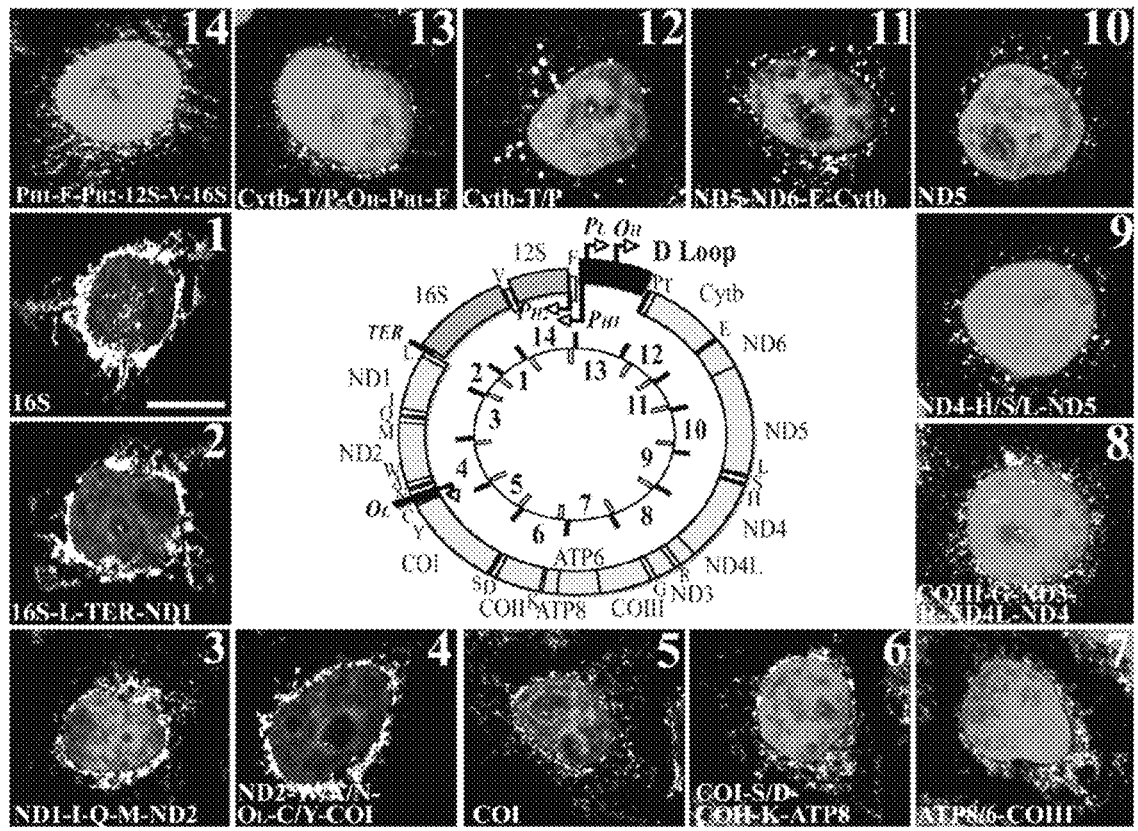
FIGS. 2A to 2D. Spatio-temporal distribution of DNA processing mitochondrial subpopulations (A) 3D-FISH/mTRIP of HeLa cells with 14 individual mtDNA probes (red), each covering a portion of the entire mitochondrial genome. Nuclei (blue) are labeled with Hoechst 33342. Scale bar=10 um. The probe number/name, and the mitochondrial gene(s) covered by the probe are indicated on the top and on the bottom of each panel, respectively. The central panel is a schematic representation of the mt genome (external circle) and of single genes within, at scale. tRNA genes are indicated with the corresponding letter. All genes are located on the H-strand, with the exception of ND6, located on the L-strand. The ribosomal RNAs (16S and 12S) are in dark grey and are slightly shifted out of the circle. The D-loop region that contains the origin of replication of the H-strand ($O_H$) and the promoters of both the H and the L strands ($PH_1$-$PH_2$, and PL, respectively) is shown in black and shifted out of the circle. The inner circle represents the position of each individual probe (see coordinates in Tables 1 and 2); some probes overlap by a few dozen of bases with the neighbor probes. The 14 individual probes cumulatively cover the complete mt genome (B) Fluorescence intensity quantification of 3D-reconstructed HeLa cells labeled with each of the individual 14 mtDNA probes, indicated on the X-axis, untreated or treated with either DNase I and RNase A. Key genes and regulatory regions are indicated on top. n=30, from three independent experiments. For each probe, the t-test was performed for nuclease-treated versus untreated cells; (*) p<0.05; () p<0.01; (*) p<0.001. A further probe, called ND6, which covers the gene with the same name located on the L-strand, was also tested. For most probes, the labeling decreases dramatically or almost disappears after RNase treatment, indicating that the labeling essentially target RNA molecules. A partial or total reduction of the labeling results from DNase treatment of probes 4, 8 and 13, indicating that these probes target also mtDNA. Probes 4 and 13 cover regions of the mt genome that contains replication origins ($O_L$ and OH, respectively), indicated on the bottom. (C) 3D FISH/mTRIP-reconstructed IMR90 primary fibroblasts labeled with the 14 individual mtDNA probes (red); legend elements as in (a). (D) Fluorescence intensity quantification of the 14 individual mtDNA probes; legend elements as in (B). n=30 from three independent experiments.
Figure 2B:
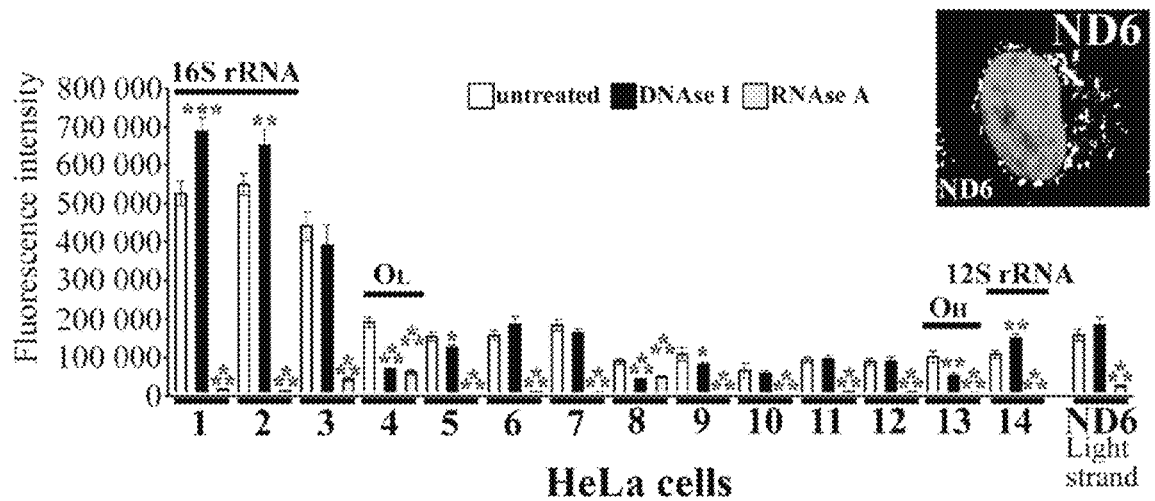
Figures 10A, 10B:
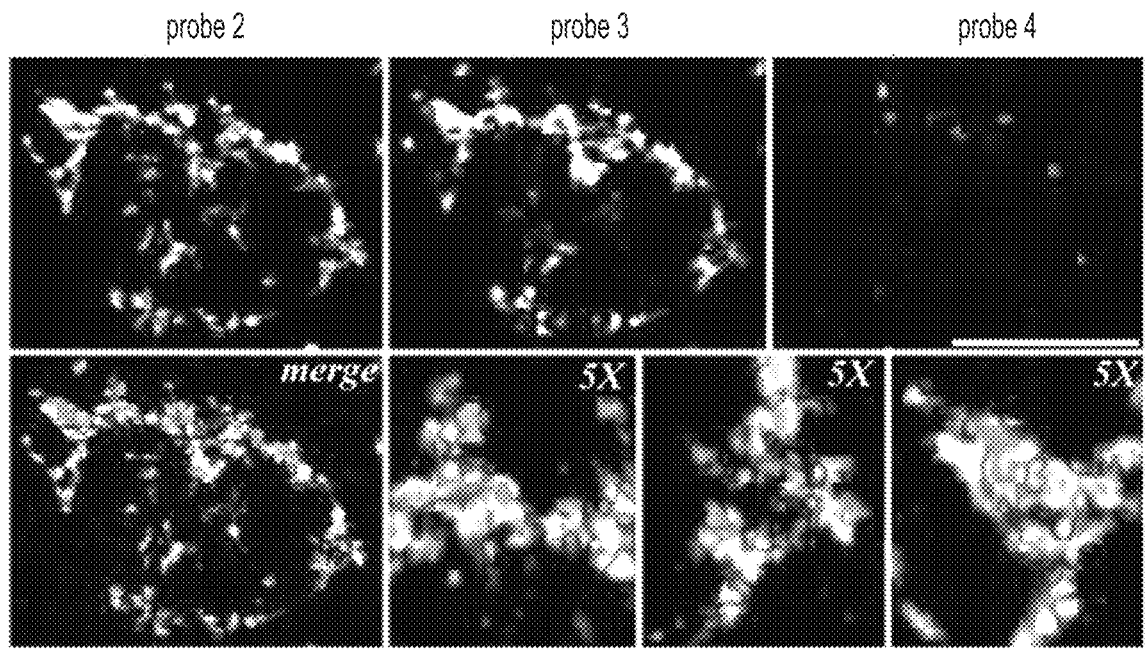
FIGS. 10A to 10F. Co-labeling with several mtDNA probes. (A) 3D FISH/mTRIP-reconstructed HeLa cells co-labeled with probes 2 (green) 3 (red) and 4 (blue), upper panels; and merge with 5× magnification of three distinct regions (lower panels). The probe used is indicated with on top. Scale bar=10 μm. (B) percentage of co-localization of the various probes; n=30 cells from three independent experiments. Co-labeling shows that most mitochondrial entities labeled with probe 2 (16S RNA) are also labeled with probe 3 (ND1), the following gene on the H-strand, but not with probe 4 that covers ND2, the further gene on the H-strand. Percentages of co-labeling are measured taking into account the total intensity of fluorescence specific to each probe. Therefore, percentages of co-labeling between probe pairs (as probes 2 vs 3 compared to probes 3 vs 2) may be different. (C) Scheme of the position of probes on the mitochondrial genome, as from FIG. 2a. (D) 3D FISH/mTRIP-reconstructed HeLa cells co-labeled with probes 7 (red) and 9 (green), upper panels; with probes 10 (red) and 9 (green) middle panels; with probes 12 (blue) and 14 (green) (lower panels). The probes used are indicated on each panel. Merge are on the right panels. Scale bar=10 um. (E) Percentage of co-localization of the various probes; for each pair of primers, n=30 cells, from three independent experiments. Note the high intensity of labeling with probe 7 at some mitochondrial entities, which may explain the reduced percentage of co-labeling with probe 9. Note also the strong and distinct labelling with probe 10 compared to the more diffuse labeling with probe 9, as well as the different spatial distribution of the two types of labelling. These differences may explain the limited co-localization between probes 9 and 10. (F) Summary of co-localization results. On the X-axis is indicated the tested probe. On the Y-axis is reported the intensity of co-labelling with the probe indicated on the segment of the column. These Y-values represent the percent of colabeling multiplied by the fluorescence intensity signal of the tested probe.
Figure 10C:
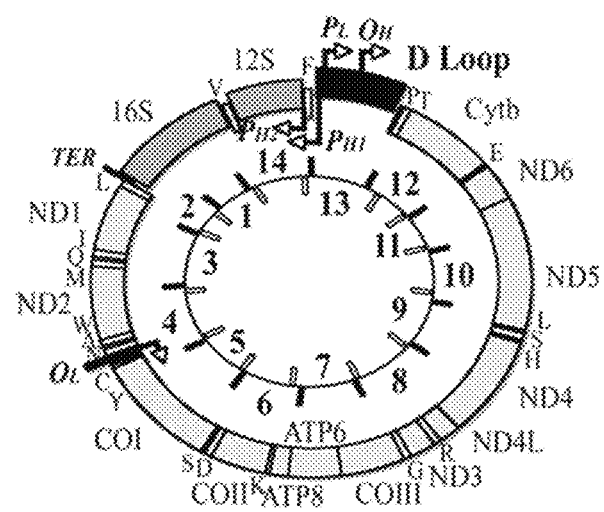
Figure 10D:
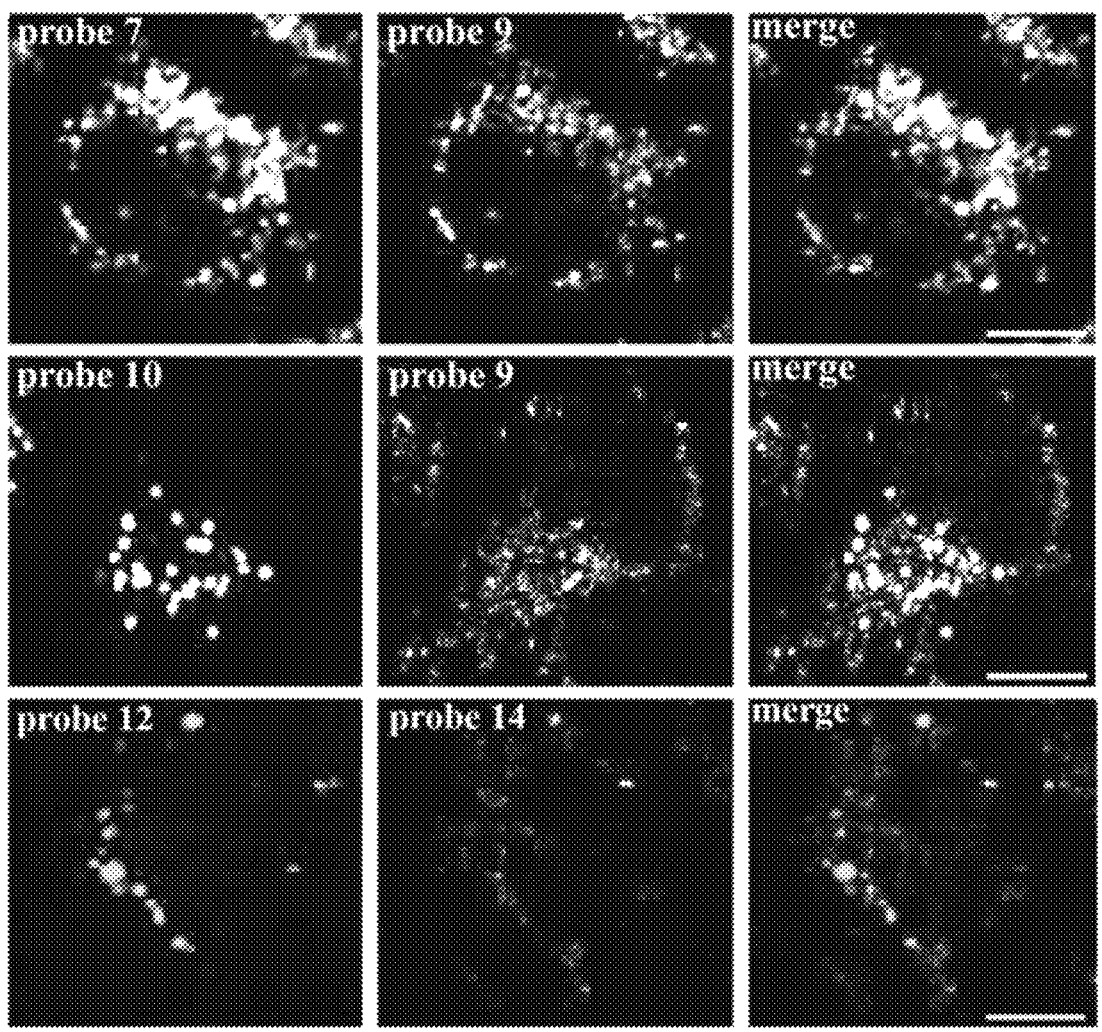
Figures 10E, 10F:
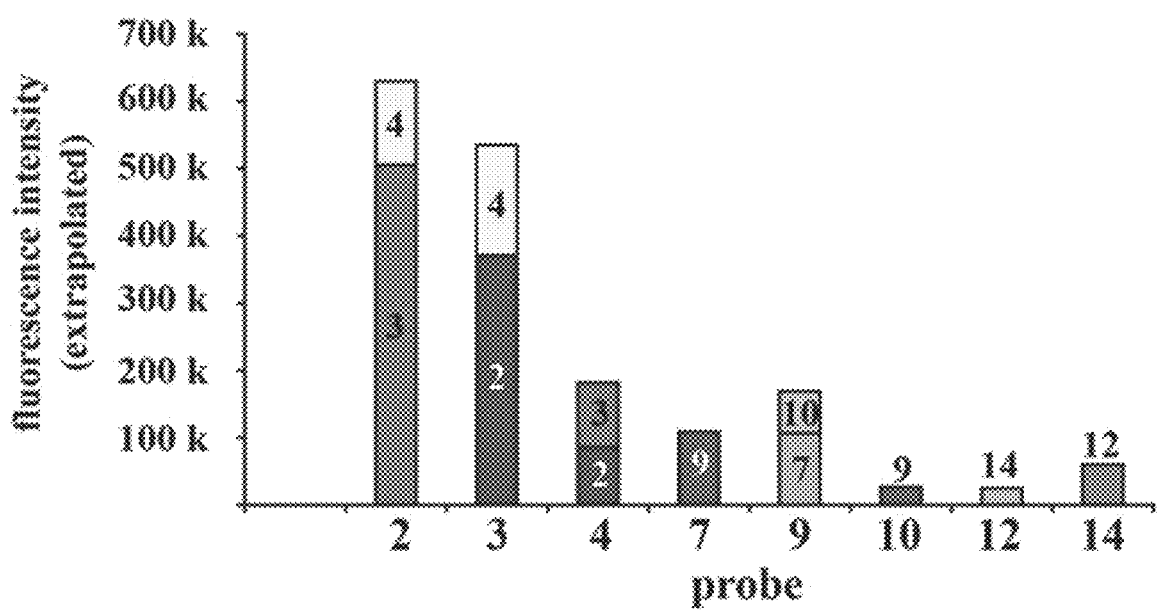

The fluorescence measurement of each probe, and its decrease after treatment with nucleases, revealed that 16S rRNA represents the major target of the labelling (probes 1 and 2, FIG. 2b). An intense signal was also observed for ND1 transcript, whose gene is located more downstream on the H-strand (probe 3, see also FIG. 10c). However, the transcript levels of ND1 were compatible with those of the other mitochondrial mRNAs using a probe specific for this gene (see below, probe ND1, FIG. 6C). Fluorescence labelling distinctly and progressively decreased with probes that cover the middle and the end of the H-strand, indicating a reduced amount of signal for late versus early H-strand transcripts.

Quantitative RT-PCR analysis of single transcripts confirmed that 16S is present in a large excess compared to most of the other transcripts (FIG. 6a), as expected[11], consistent with RNA levels identified by mTRIP thus validating the FISH data. Furthermore, by coupling 3D-FISH/mTRIP for each of the 14 mtDNA probes to immunofluorescence with anti-TOM22, a mitochondrial outer membrane marker that identifies the entire mitochondrial population, the inventors have found that not only 16S rRNA (probes 1 and 2) is present in a larger proportion of mitochondria than are the other transcripts, but also that mitochondria carry larger amounts of this transcript compared to other transcripts (FIG. 7).

Figure 2C:
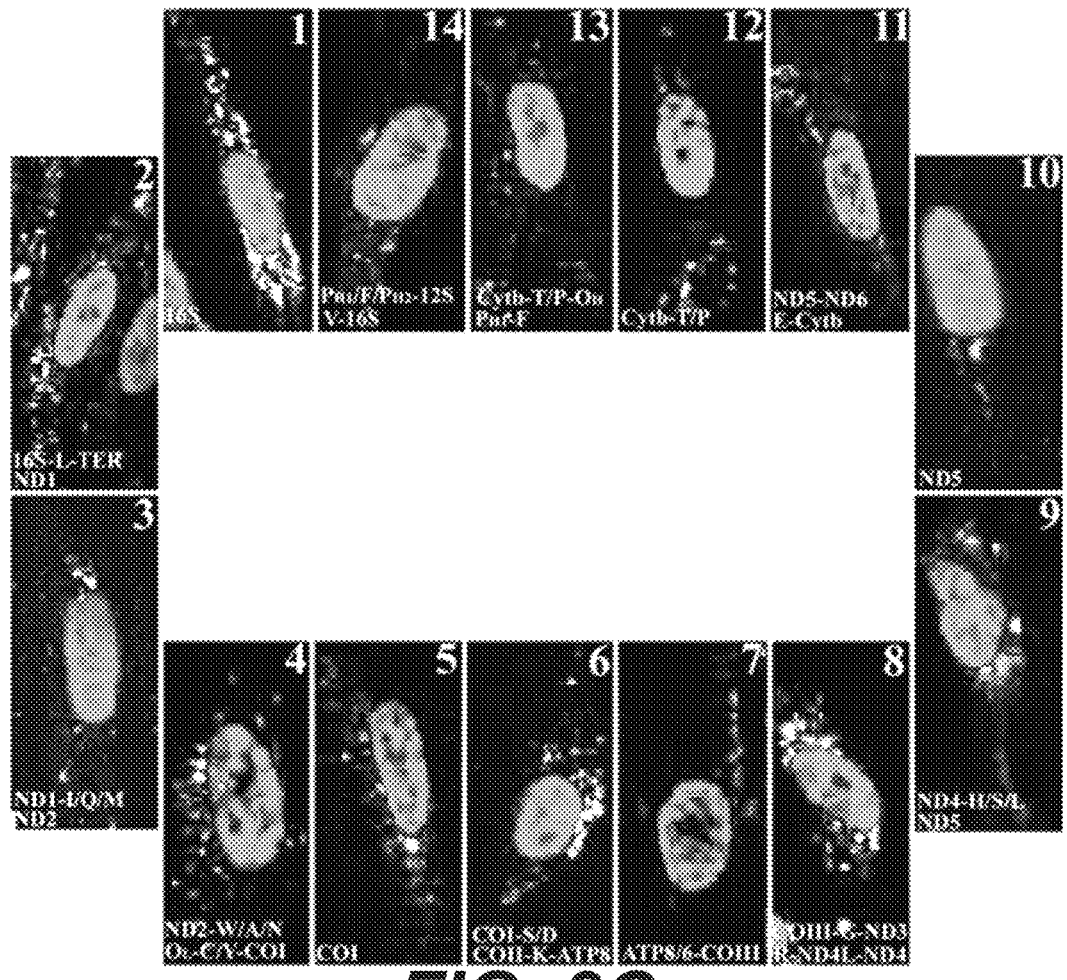
Figure 2D:
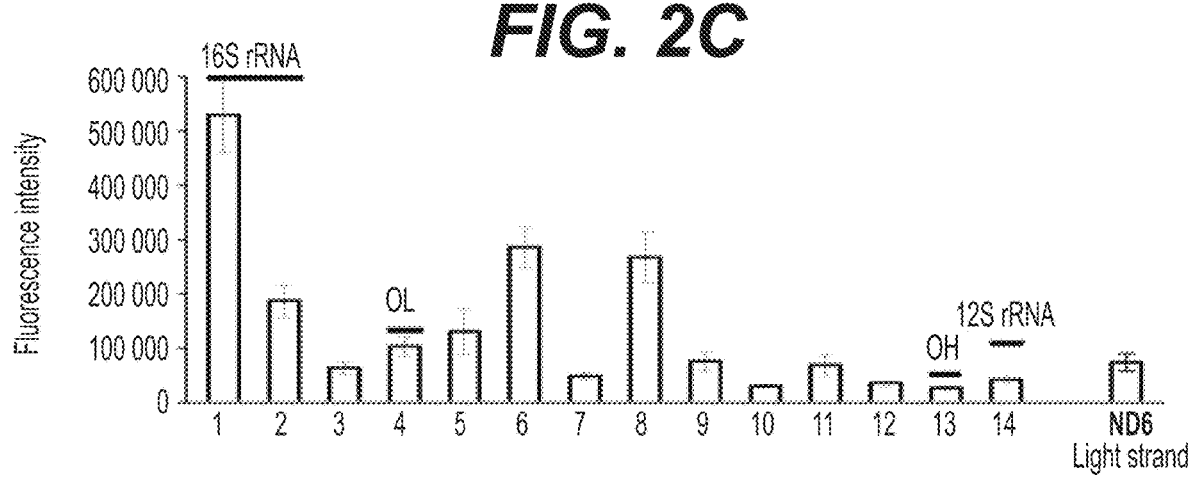
Figure 6A:
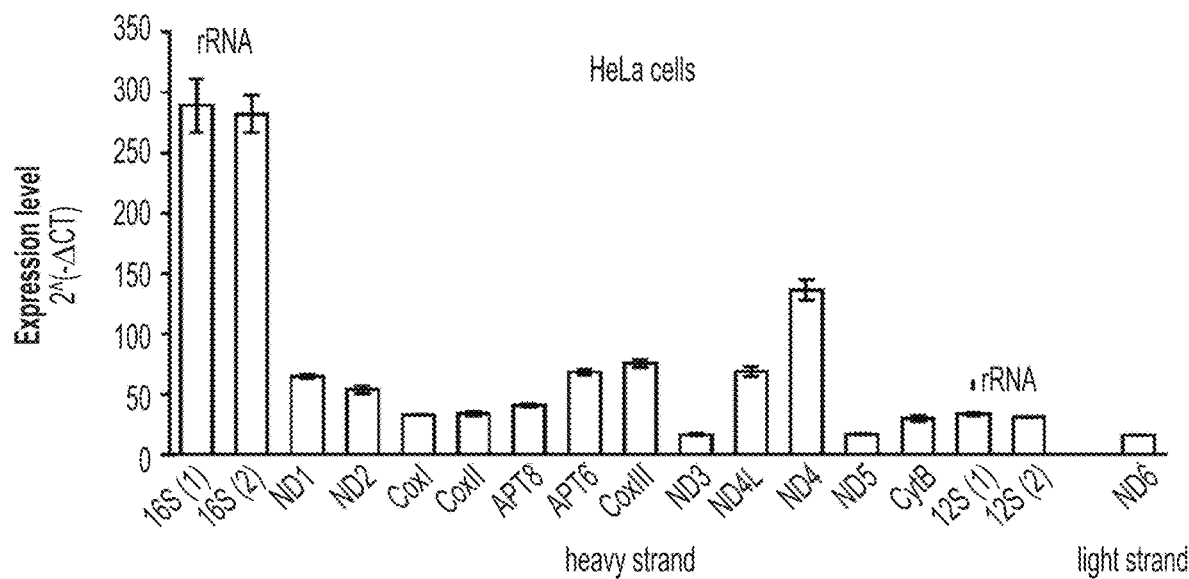
FIGS. 6A to 6C. Real-time quantitative PCR of individual mitochondrial genes and comparison with FISH data. (A) Expression levels of the individual mitochondrial genes in Hela cells. 16S and 12S were analyzed with two independent sets of primers. Mean of 3 experiments±standard deviation. (B) Relative gene expression of 16S and ND1 compared to 12S (12S was arbitrarily indicated as 1) in HeLa cells and in IMR-90 human primary fibroblasts. (C) Fluorescence intensity quantification of probe ND1 (and of probe 3, data from FIG. 2 B, used as comparison) in presence and absence of nucleases. For each probe the coordinates in the mitochondrial genome are indicated below. n=30, three independent experiments. T-test, compared to untreated cells (***) p≤0.001. On the right, 3D-reconstructed HeLa cell labelled with probe ND1 which recognizes a portion of the ND1 gene; scale bar=10 μm.
Figure 6B:
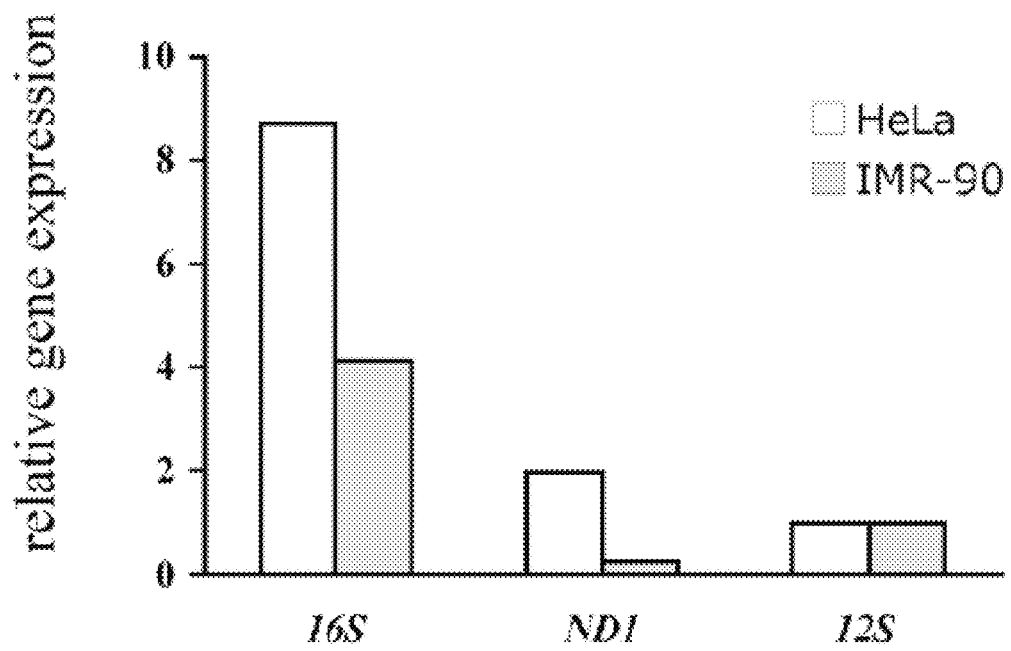
Figure 6C:
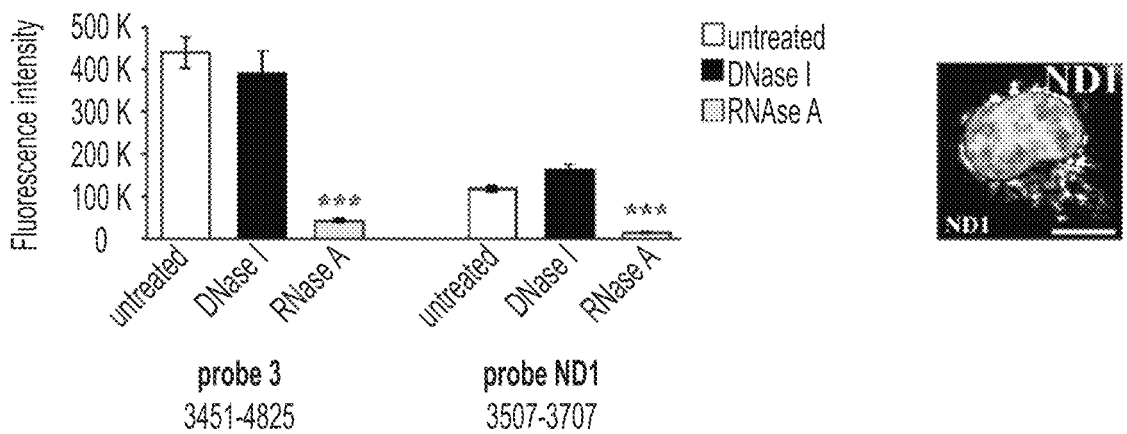
Figure 7A:
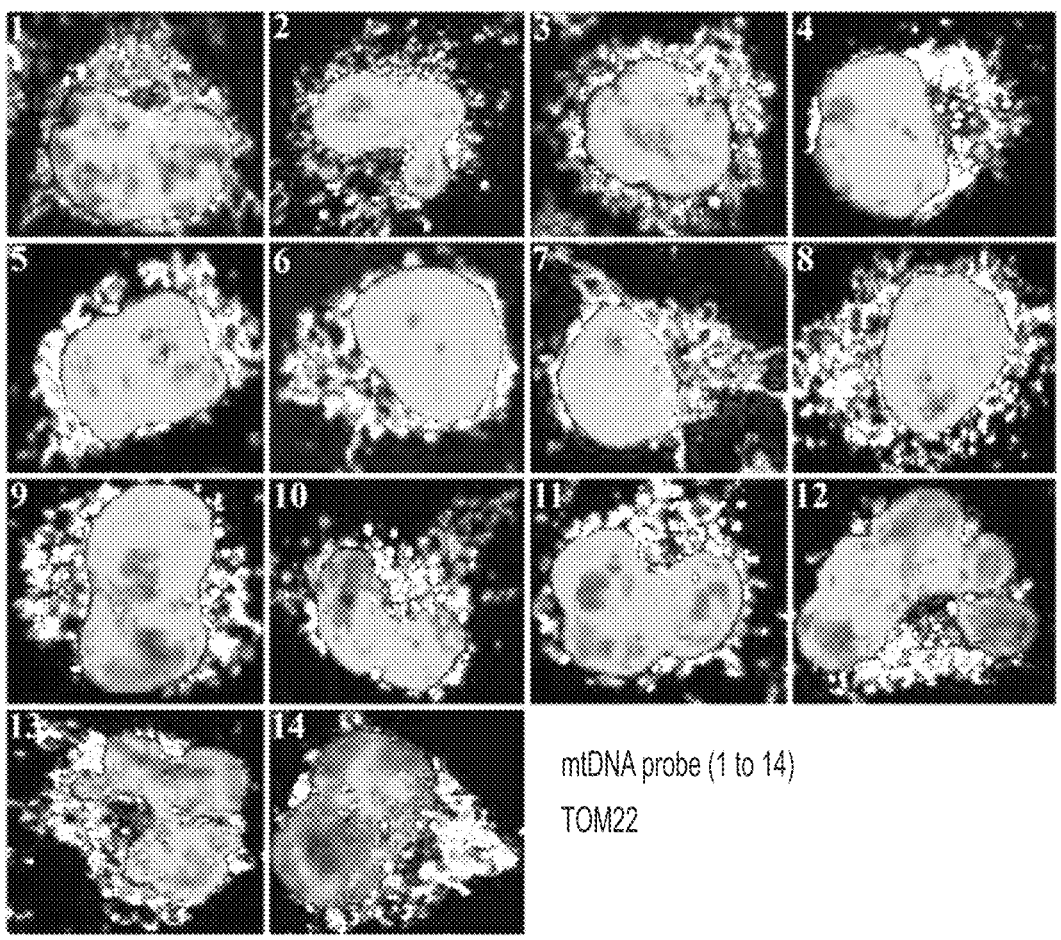
FIGS. 7A to 7C. Semi-quantitative analysis of the proportion of mitochondria labeled with each of the 14 mt DNA probes. (A) 3D-FISH/mTRIP coupled to immunofluorescence. Reconstructed HeLa cells labeled with the mtDNA probe indicated (red) and anti-TOM22 (green). The number in each panel indicates the probe used. (B) Percentage of 3D-FISH/mTRIP labelled mitochondria in the total mitochondrial population (for each probe, co-labelling of 3D-FISH/mTRIP and anti-TOM22). For each probe, n=30 cells; three independent experiments. (C) Intensity of fluorescence in TOM22-labelled mitochondria, calculated for each probe by multiplying the intensity of fluorescence (fi) by the percentage (p) of FISH labeled mitochondria (=fixp). Each value indicates the relative amount of transcripts carried by the TOM22-labelled mitochondrial population.
Figure 7B:
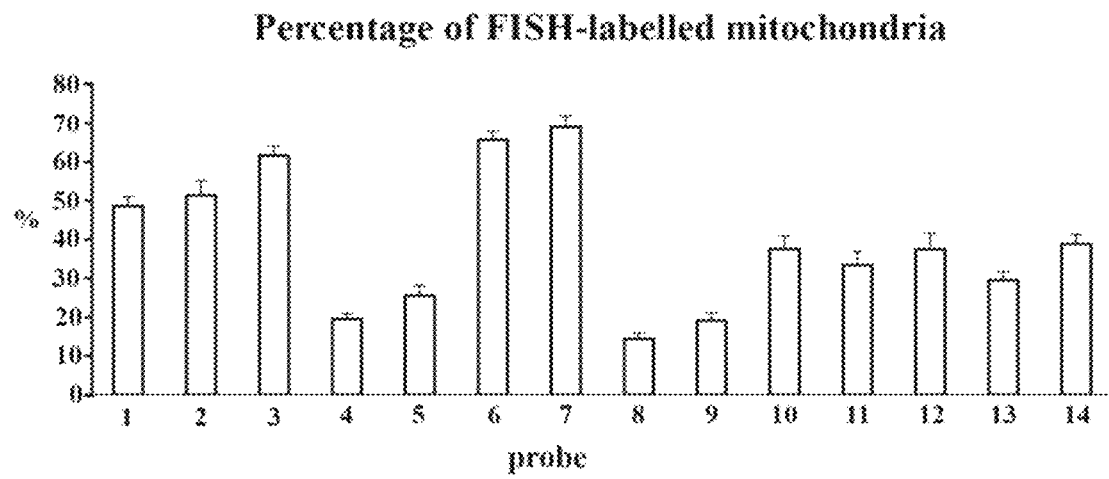

RT-qPCR confirmed the 3D-FISH/mTRIP result that 12S rRNA is present at significantly lower levels than 16S rRNA (FIG. 6a). This was unexpected given that both rRNAs are transcribed from the same promoters, PH1 and to a lower extent PH2[12] (see scheme in FIG. 2a), and that they were reported previously to be produced at similar levels in vitro[11]. Although the possibility that the lower signal for 12S rRNA is due to inaccessibility of primers/probes cannot be excluded, this possibility seems unlikely since 12S rRNA levels were confirmed by two different tests, and using three different target regions (see also FIG. 8. Low levels of 12S RNA were also found in primary fibroblasts (FIG. 2d, FIG. 6b). FIG. 2a also shows that in HeLa cells the distribution of labelled mitochondria varies as a function of the mtDNA region tested.

Indeed, 16S rRNA is present mainly in mitochondria located in the perinuclear region and in tubular, filamentous mitochondria, whereas transcripts of the last third of the H-strand appear in fragmented mitochondrial entities, distributed more randomly in the cytoplasm.

Figure 9:
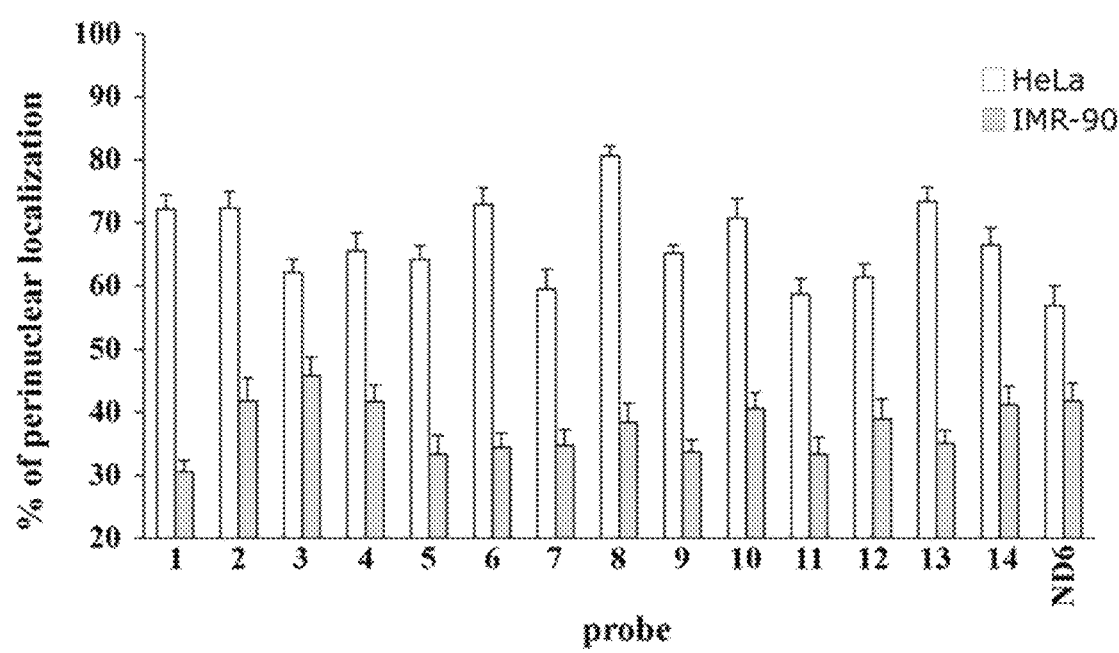
FIG. 9. Perinuclear distribution of mitochondria labeled with the individual mtDNA probes. The histogram shows the perinuclear localization, defined as the region within 2 μm from the nuclear border, of mitochondria labeled with the probes indicated on the X-axis, in HeLa ells and in IMR-90 primary fibroblasts (n=30; from three independent experiments). Mean±SEM.

Thus, mitochondria cluster around the nucleus during processing of the 16SRNA, and they spread to the cellular periphery as RNA processing on the H-strand terminates. This finding was confirmed by quantitative analysis of the perinuclear localization of 3D-FISH labelled mitochondrial populations (72.18±2.28% and 72.35±2.66% of labelled mitochondria were located in the perinuclear region with probes 1 and 2 respectively; FIG. 9). Moreover, quantitative analysis revealed preferential perinuclear location (72.87±2.66%) also for mitochondria carrying abundant transcripts, such as ATP8 (targeted by probe 6). In addition, perinuclear mitochondria with probes recognizing mtDNA (see below) were observed (80.65±1.54% and 73.37±2.24% for probes 8 and 13, respectively, and 65.47±2.24% for probe 4). In general, the perinuclear localization of mitochondria labelled by 3D-FISH/mTRIP is high in HeLa cells (>50% of the total mitochondrial population). Although a different localization of mitochondrial populations according to the detected type of transcript was also observed in IMR-90 primary fibroblasts, no prevalent perinuclear distribution of mitochondria appears in these cells (30-47%, all probes included; FIG. 2c and FIG. 9). Moreover, mitochondria labelled for various RNAs and DNAs appeared to be more fragmented in IMR-90 fibroblasts than in HeLa cells.

Mitochondrial transcripts exist as processed transcripts of single genes, and unprocessed polycistronic transcripts[1]. The RNA labelling which we observed with 3D-FISH/mTRIP may represent one or both of these types of transcripts. Experiments involving co-labelling with one or more mtDNA probes helped to distinguish between unprocessed RNA molecules and individual transcripts (FIG. 10). Early transcripts on the H-strand appeared largely as unprocessed molecules, whereas late H-strand transcripts appeared frequently as processed molecules.

To analyse further mitochondrial transcription, a new mixture of probes was used (mTRANS: probes 1, 6, and 11) that are distributed evenly along the circular genome. These probes label rRNA and mRNA, and they do not recognize regions involved in the initiation of DNA replication (see below). FISH experiments with mTRANS, in the absence or presence of nucleases, confirmed that this probe set detects only RNA.

Colocalization of 3D-FISH/mTRIP Labelling with Mitochondrial Nucleoid Markers

The inventors then checked the colocalization between mTRANS that labels mitochondrial transcripts, and nucleoid markers TFAM and Polγ, which label submitochondrial structures. Extensive colocalization between immunostaining of either Polγ or TFAM and mTRANS (FIG. 3 A) indicated that transcripts detected by FISH were mostly confined to labelled mitochondrial nucleoids, as suggested above. Indeed the inventors found extensive colocalization in all of the combinations tested here, although in each case a fraction of foci did not show colocalization. TFAM and Polγ colocalized with mTRANS by 83.89±4.7% and by 92.69±4.0%, respectively, indicating that less than one tenth of the mitochondrial nucleoids labelled with these markers did not contain transcript levels detectable by mTRIP. Conversely, mTRANS colocalized by 63.53±4.1% and by 66.23±5.1% with TFAM and Polγ, respectively, indicating that about one third of the mitochondrial transcripts revealed by mTRIP did not appear to be located in nucleoids where either TFAM or Polγ are present at detectable levels. The different extents of colocalization among foci are in agreement with significantly different amounts of TFAM in nucleoids (Chen, 2005; Shutt, 2010; Spelbrink, 2010; Wai, 2008). In this context TFAM has been recently found to act more as a transcription activator than as a core-component of the transcription machinery in vitro (Shutt et al. 2010), and Polγ may be present at low or undetectable levels in transcription-active nucleoids. Therefore, within the limits of resolution of mTRIP, mTRANS largely colocalizes with nucleoid markers. The different levels of colocalization between FISH probes and nucleoid markers might be linked to heterogeneity of nucleoids (DNA and protein content).

FISH Signal was not Limited by Probes Concentration.

To check whether the intensity labelling by 3D-FISH/mTRIP was limited by the amount of probes, the inventors have increased by 5-fold the probe concentration, using 200 ng of mTOT, which corresponds to one of the highest values described in the literature for FISH experiments[33]. It was found that increasing probe concentration did not increase the proportion of labelled mitochondria nor the absolute values of the signal (FIG. 5), indicating that the labelling of a subset of mitochondria by 3D-FISH/mTRIP was not due to limited concentrations of the probe.

The inventors have then co-labelled cells with mTOT and with a probe that targets nuclear Alu sequences[34] (probe Hs Alu) and found that labelling of mitochondrial nucleic acids did not preclude the labelling of nuclear nucleic acids (FIG. 5), indicating that the accumulation of mtDNA labelling in the perinuclear region was not due to inaccessibility of the probe to the nucleus. This experiment also confirmed that labelling with mtDNA probes was specific to mitochondrial nucleic acids.

HeLa cells were also labelled with a further mix of probes, called mTOTΔr, that includes all probes present in mTOT with the exception of probes 1, 2 and 14 that cover the rDNA portion of the mt genome. FIG. 5 shows that the intensity of labelling in the absence of rDNA probes was at least as high as with the probe mTOT, indicating that 3D-FISH labels mitochondrial mRNAs even in the presence of large amounts of rRNAs. The inventors have also observed that mTOTΔr-labelled mitochondria were not mostly located in the perinuclear region as it was the case with the mTOT mix. This experiment suggested that different combinations of mt DNA probes label distinct mitochondrial populations. It also indicated that mTOT-labelled mitochondria located in the perinuclear region largely correspond to organelles that contain rRNAs. This notion was confirmed by experiments with individual probes (see FIG. 2a,b) that showed the highest labelling for 16S rRNA.

Figure 8A:
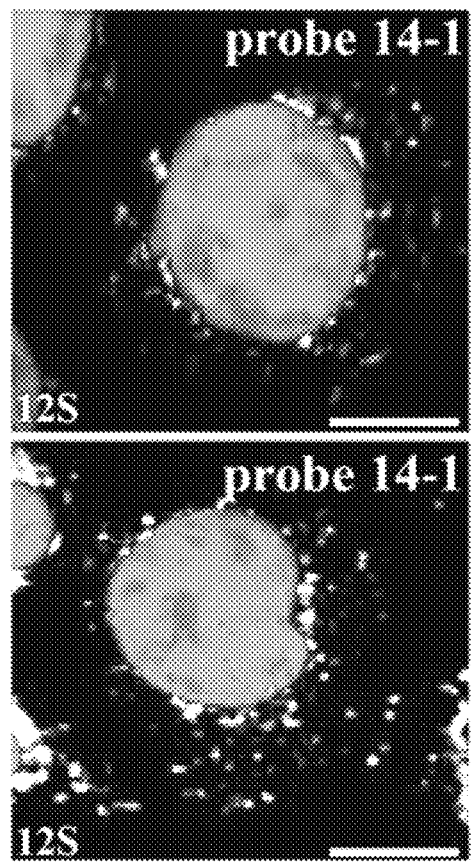
FIGS. 8A and 8B. 3D-FISH on the 12S region using an alternative probe. (A) 3D-FISH/mTRIP of two HeLa cells with the probe 14-1. Scale bar=10 um. (B) Quantification of the fluorescence intensity with the probe 14-1 (data for probes 1 and 14 are from FIG. 2b) in HeLa cells, indicating that the labeling is dramatically lower for the 12S (probes 14 and 14-1) than for the 16S (probe 1) containing region. n=30 from three independent experiments.
Figure 8B:
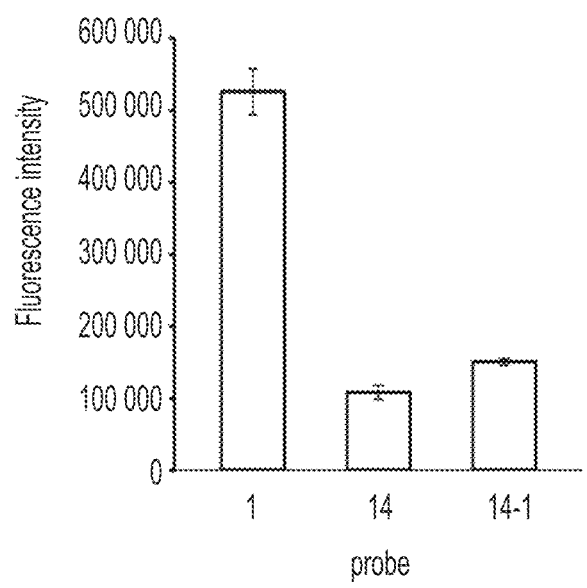

16S but not 12S rRNAs was Present in Larger Amounts than the Other Transcripts and was Produced by a Larger Proportion of Mitochondria 12S and 16S rRNA are transcribed in vitro about 10-30 fold more than the other genes on the H-strand[35]. rRNA transcripts are mostly produced from promoter PH1 and terminate at specific regions located downstream of 16S whereas mRNAs and tRNAs are essentially produced from the PH2 promoter[36], see scheme in FIG. 2a. By 3D-FISH, the inventors have found that transcripts containing 16S rRNA (probes 1 and 2) are present in larger amounts than the other transcripts, as expected, but surprisingly this was not the case for transcripts containing 12S rRNA (probe 14, FIG. 2). This finding was confirmed by quantitative RT-PCR (qRT-PCR) analysis of the 16S and 12S rRNAs (FIG. 6a), and by a second fluorescent probe (14-1) in the region of the 12S RNA (FIG. 8). High levels of 16S but not of 12S rRNA were observed also in human primary fibroblasts (FIG. 2d, FIG. 6b).

High levels of fluorescence were observed, surprisingly, also for probe 3 that essentially covers the ND1 gene localised downstream of 16S on the H-strand. Although the signal for probe 3 was lower than for 16S rRNA (probes 1 and 2), as expected[35], it was at least two-fold higher than for the other genes located downstream of rRNA transcription terminators (FIG. 2B). The elevated fluorescence with probe 3, observed in HeLa cells but not in primary fibroblasts (FIG. 2d), seemed due to the targeting of unprocessed transcripts that also contain 16S (see next section). The intensity of fluorescence labelling dropped by at least one half with probes 4 to 7 that recognize the downstream region of the H-strand (genes ND2 to the COM), and even more with probes 8 to 12 that cover the most downstream region, from ND3 to CytB. Interestingly, low levels of labelling appeared also for probe 13, that recognizes the region with the D-loop. On the L-strand, probe ND6 labels the region containing the ND6 gene with intensity comparable to that of probes 4-7 on the H-strand. It should be noticed that the fluorescence intensity of transcripts detected with probes 4, 8, and 13 was even lower than the actual value, given that these probes also recognize DNA (FIG. 2b).

Figure 7C:
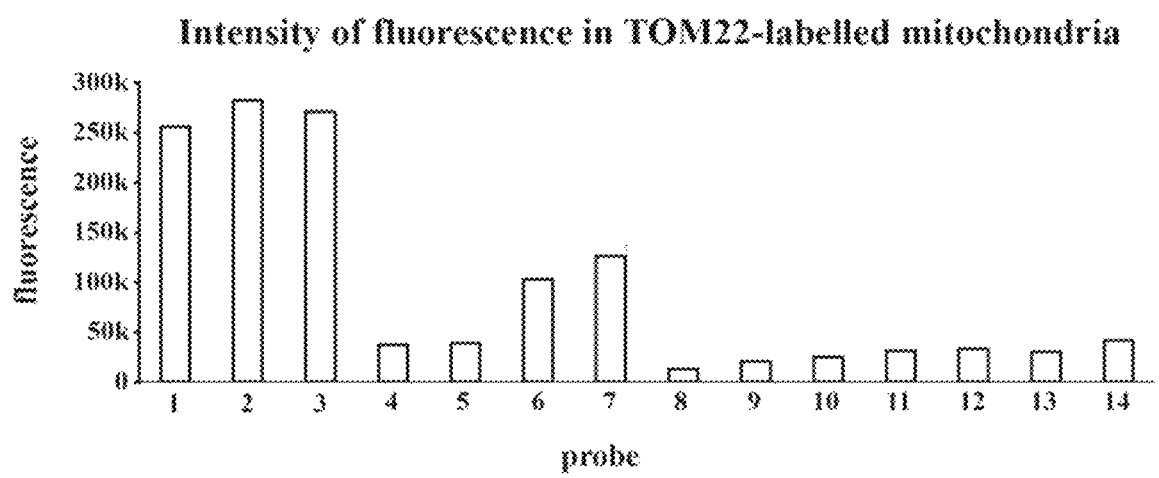

The production of large amounts of a given RNA may originate from elevated transcription by individual mitochondria or from a large number of mitochondria implicated in transcription, or both. To investigate this aspect, the inventors have coupled 3D-FISH/mTRIP of each of the 14 mtDNA probes to immunofluorescence with anti-TOM22, a mitochondrial outer membrane marker that identifies the entire mitochondrial population. First, the percentage (p) of co-localization between anti-TOM22 and each probe was assessed. The inventors have found that a large proportion of mitochondria (49-69%) was labelled with probes 1 to 3, and with probes 6-7, while only 19-38% of mitochondria are labelled with the remaining probes (FIG. 7 a-b). These data indicated that a larger number of mitochondria carry 16S to ND1 RNAs, and COII to COIII RNAs, than of the other mitochondrial transcripts. Then, for each probe the intensity of fluorescence present in TOM22-labelled mitochondria was evaluated, as an indication of the relative amount of transcripts carried by that mitochondrial population. Therefore, for each probe the percentage of labelled mitochondria (value p, see above) was multiplied by the intensity of fluorescence of the probe. It was observed that probes 1 to 3 had the highest values, whereas values were 2.5-fold lower for probes 6-7, and until 20-fold lower for the remaining probes (FIG. 7c). All together, these results indicated that not only 16S and to a minor extent ND1 RNAs were present in a larger proportion of mitochondria than were the other transcripts, but also that mitochondria carried larger amounts of these than of the other transcripts. Conversely, the remaining transcripts were present in a small proportion of mitochondria where they were also present in little amounts. An intermediary situation was observed for CoII to COIIIRNAs (probes 6-7), that were present in a relatively large portion of mitochondria but in small amounts therein.

Labelling of Unprocessed and Processed Transcripts

An intriguing result of 3D-FISH experiments concerned the high levels of RNA labelling for probe 3 that essentially covers ND1 (see above). High levels of ND1 labelling may results from PH1 transcription of rRNAs that did not stop at terminators or, alternatively, from a particularly long-lived RNA, although it was not reported that the ND1 transcript was more long-lived than the other mRNA in HeLa cells[37]. In agreement with the first hypothesis, the levels of ND1 labelling (probe 3) were close to those of 16S rRNA (probes 1-2). The inventors have reasoned that large amounts of ND1 RNA may result from leaky termination of transcription from PH1. To check whether ND1 and 16S RNAs labelled by 3D-FISH were present on the same molecules and, more in general, whether RNA labelling by 3D-FISH targeted polycistronic precursor RNAs and/or processed transcripts the inventors have performed 3D-FISH with two or three probes simultaneously. It was found that labelling with probes 2 and 3 mostly overlapped (92±1.4% of probe 2 colocalized with probe 3, and 84±1.9% of probe 3 colocalized with probe 2, FIG. 10), indicating that 16S and ND1 RNAs were essentially located on the same molecule or on distinct molecules that were present at equimolar amounts on the same mitochondrial entities. This was not the case for probe 4 that targeted the region just downstream of ND1, and that colocalized with probes 2 and 3 in only 23±3.2% and 27±3.2% of cases, respectively, FIG. 10. Thus, if 16S and ND1 RNAs labelled by 3D-FISH were present on the same molecule, then a relevant part of PH1 derived rRNA transcripts may not have stopped at termination signals, but proceeded through ND1, at least in HeLa cells.

The inventors have performed co-labelling with additional pairs of probes to verify the simultaneous presence of transcripts in mitochondria. It was found that probe 14, that labelled 12S rRNA present at the beginning of the H-strand transcript colocalized with probe 12, that labelled CytB present at the end of the same transcript, in 55.6±7% of cases, indicating that mitochondrial entities showing co-localization either contained the 5' and the 3' end of the PH2-directed transcript, i.e. the complete H-strand transcript, or that 12S and CytB processed transcripts were present in equimolar amounts on the same mitochondrial entities (FIG. 10). It was also observed a large overlap (>60%) for labelling with probes 7 and 9 that covered close regions localized in the second half of the H-strand, indicating that most mitochondrial entities contained both transcripts or that these transcripts were present on the same molecule. The levels of colocalization decreased with the adjacent probes 9 and 10, that additionally showed a rather diverse spatial distribution, indicating that these probes mostly labelled transcripts located on different mitochondrial entities or on different molecules (FIG. 10). These results are summarized in FIG. 10f that takes into account the percent of co-localization and the total fluorescence intensity of the tested probe. Although just indicative in quantitative terms, these data nevertheless confirms a relevant co-localization of transcripts targeted by probes 2 and 3 (located in the first quarter of the H-strand), and also by probes 7 and 9 (located in the third quarter of the H-strand). On the contrary, data show a scarce co-localization of transcripts targeted by probes 2-3 and 4, and probes 9 and 10, revealing that most of these transcript pairs were not present in the same mitochondria. In conclusion, colocalization experiments strongly suggested that transcripts labelled by 3H-FISH probes represented both unprocessed RNA molecules, in particular the early transcripts on the H-strand, and processed individual transcripts. This proof of principle showed that processed and unprocessed RNA molecules could be identified for any mitochondrial gene of interest using, appropriate pairs of probes in co-localization experiments.

qPCR Analysis of Mitochondrial Transcripts or Correlation Between 3D-FISH/mTRIP and RT-qPCR Transcript Levels To check whether the proportion of the various transcripts detected with 3D-FISH in distinct mitochondrial populations were consistent with the transcript levels of the mitochondria, the inventors have performed qRT-PCR experiments for each mitochondrial rRNA and mRNA gene (FIG. 6a). A direct comparison of 3D-FISH and qRT-PCR data was not suitable since FISH probes used here cover regions larger than a single gene, with the exception of probes 5 and 10 that cover only COI and ND5, respectively. Nevertheless, quantitative RT-PCR analysis of the other mitochondrial genes analysed showed expression level profiles compatible with those observed by FISH analysis. The transcript levels of ND1 were compatible with FISH using a probe specific for this gene (probe ND1, FIG. 6C) but not with the longer probe 3, which probably labels also unterminated rRNA transcripts (as suggested in the previous section "Labelling of unprocessed and processed transcripts"). In conclusion, a good correlation between RT-qPCR, which detects transcripts of the entire mitochondrial and cellular populations and mTRIP, which reveals RNAs in a fraction of mitochondria and at the single-cell level, was noted.

TABLE 2

Position of the probe on the human mitochondrial genome. The coordinates of the genetic element present at a given position of the mitochondrial genome (NC_012920.1, NCBI or GenBank or MITOMAP accession number) are indicated in column 1 (data from MITOMAP: http://www.mitomap.org/MITOMAP/HumanMitoSeq). The name of the element itself is indicated either on column 2 or 3 (direct and inverse orientation with respect to the direction of transcription of the H-strand, respectively). In the last three columns is/are indicated the probe(s) that hybridize with the indicated region. Even hybridization of a few nucleotides is indicated.

| position | element | element | probe | probe | probe |
| --- | --- | --- | --- | --- | --- |
| 110-441 | | Origin H | | 13 | 13-1 |
| 213-235 | CSB1 | | | 13 | 13-1 |
| 299-31 5 | CSB2 | | | 13 | 13-1 |
| 346-363 | CSB3 | | | 13 | 13-1 |
| 392-445 | | PL (or LSP) | | 13 | 13-1 |
| 545-567 | PH1 | | 14 | 13 | 13-1 |
| 577-647 | tRNAphe | | 14 | 13 | |
| 645 | PH2 | | 14 | | |
| 648-1601 | 12S RNA | | 14 | | |
| 1602-1670 | tRNAval | | 14 | | |
| 1671-3229 | 16s RNA | | 14 | 1 | 2 |
| 3230-3304 | tRNAleu (UUR) | | | | 2 |
| 3307-4262 | ND1 | | | 3 | 2 |
| 4263-4331 | tRNAile | | | 3 | |
| 4365-4400 | | tRNAgln | | 3 | |
| 4402-4469 | tRNAf-met | | | 3 | |
| 4470-5511 | ND2 | | 4 | 3 | |
| 5512-5579 | tRNAtrp | | 4 | | |
| 5587-5655 | | tRNAala | 4 | | |
| 5657-5729 | | tRNAasn | 4 | | |
| 5721-5755 | Origin L | | 4 | | |
| 5761-5826 | | tRNAcys | 4 | | |
| 5826-5891 | | tRNAlys | 4 | | |
| 5904-7745 | COI | | 4 | 5 | 6 |
| 7446-7514 | | tRNAser (UCN) | | | 6 |
| 7518-7585 | tRNAasp | | | | 6 |
| 7586-8329 | con | | | | 6 |
| 8295-8364 | IRNAlys | | | | 6 |
| 8366-8572 | ATP8 | | 7 | | 6 |
| 8527-9207 | ATP6 | | 7 | | |
| 9027-9990 | COIN | | 7 | 8 | |
| 9991-10038 | tRNAglu | | | 8 | |
| 10059-10404 | ND3 | | | 8 | |
| 10405-10469 | tRNAarg | | | 8 | |
| 10470-10766 | ND4L | | | 8 | |
| 10760-12137 | ND4 | | 9 | 8 | |
| 12138-12206 | tRNAhis | | 9 | | |
| 12207-12265 | tRNAser(AGY) | | 9 | | |
| 12266-12336 | tRNAleu(CUN) | | 9 | | |
| 12337-14148 | NAD5 | | 9 | 10 | 11 |
| 14149-14673 | | NAD6 | | | 11 |
| 14674-14742 | | tRNAglu | 12 | | 11 |
| 14747-15887 | CytB | | 12 | 13 | |
| 15888-15953 | tRNAthr | | 12 | 13 | |
| 15956-16023 | | tRNApro | 12 | 13 | 13-1 |
| 16024-191 | | 7SDNA | 12 | 13 | 13-1 |

3D-FISH/mTRIP Revealed mtDNA Initiation of Replication

Figure 11A:
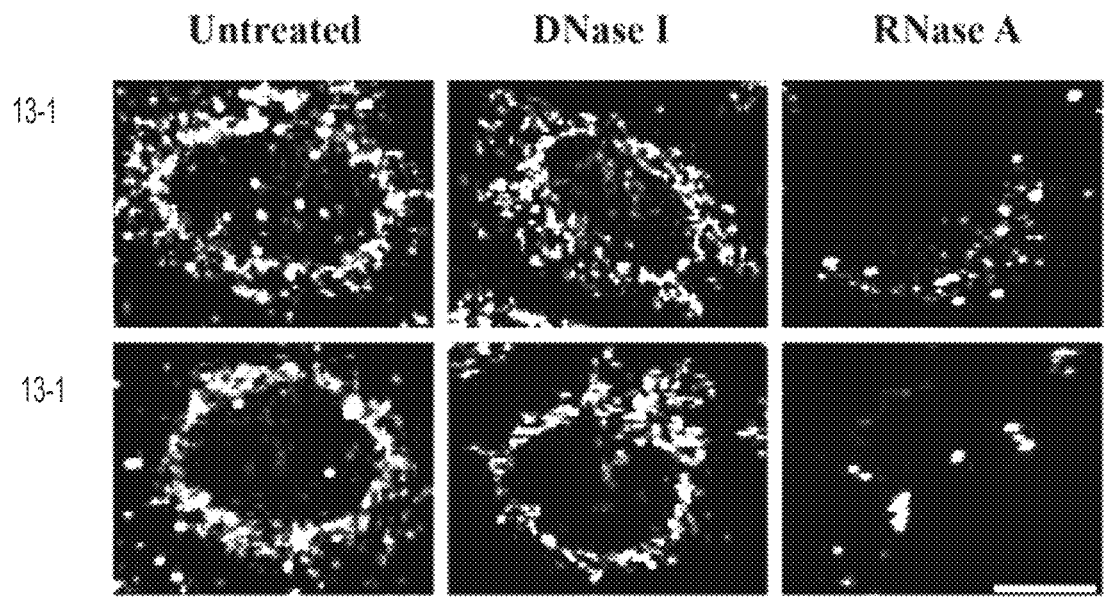
FIGS. 11A and 11B. Analysis of probes to label initiation of mt DNA replication. (a) 3D FISH/mTRIP-reconstructed HeLa cells labeled with probe 13-1 (red) either untreated or treated with nucleases, as indicated. For each condition, two different cells are shown (upper and the lower panel, respectively). Scale bar=10 um. (b) Fluorescence intensity quantification of 3D-reconstructed HeLa labeled with either probe 13, probe 13-1, or probe mREP, indicated on top. The X-axis indicates whether cells were untreated or treated with either DNase I and RNase A. For each probe and for each condition, n=30 from three independent experiments. T-test, compared to untreated cells, () p<0.01; (*) p<0.001. Values for mREP, shown here for direct comparison, are as in FIG. 3B. Treatment with DNaseI induces an increase in the labeling with probe 13-1, indicating that a portion of this probe is normally inhibited from binding because of the presence of a DNA-associated structure. However, this is not the case with the more extended probe 13. The reason for such increase is not clear and the sequence involved has not been identified.
Figure 11B:
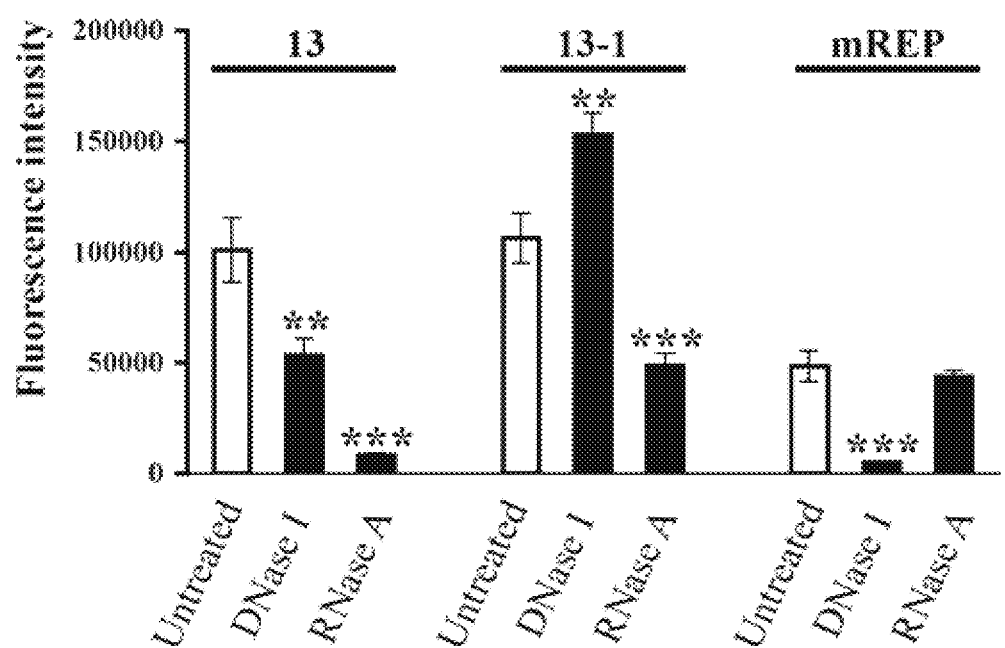

The inventors have observed above (FIG. 2b) that three probes (13, 4 and 8) detected not only RNA but also DNA. Interestingly, probes 13 and 4 included the regions of initiation of replication of the H- and the L-strand, respectively, suggesting that these probes detected DNA regions engaged in the initiation of replication. Probe 8 included the ND4 region, where an additional origin of replication for the L-strand has been observed using atomic force microscopy[13] and which is expected to be activated less frequently than the two major ones. These three origins are located almost symmetrically on the mt genome, as schematized in FIG. 3a. To assess whether DNA labeling by 3D-FISH/mTRIP was associated with initiation of DNA replication, the inventors have investigated the region covered by probe 13 which is unique within the entire mitochondrial genome, as it contains a sequence that is not transcribed, according to the terms used herein, in particular a sequence that is substantially not transcribed, and therefore it should be present only in its DNA form (FIG. 3b). The inventors generated a second probe (13-1) which covered a shorter region than probe 13 and which did not contain genes, and a third probe (mREP) that covered only non-transcribed DNA (FIG. 3b). 3D-FISH/mTRIP with each of the three probes showed that only mREP resulted in fully DNaseI-sensitive and fully RNaseA-resistant labelling (FIG. 3c, FIG. 11) indicating that this probe specifically labelled DNA.

Figure 3D:
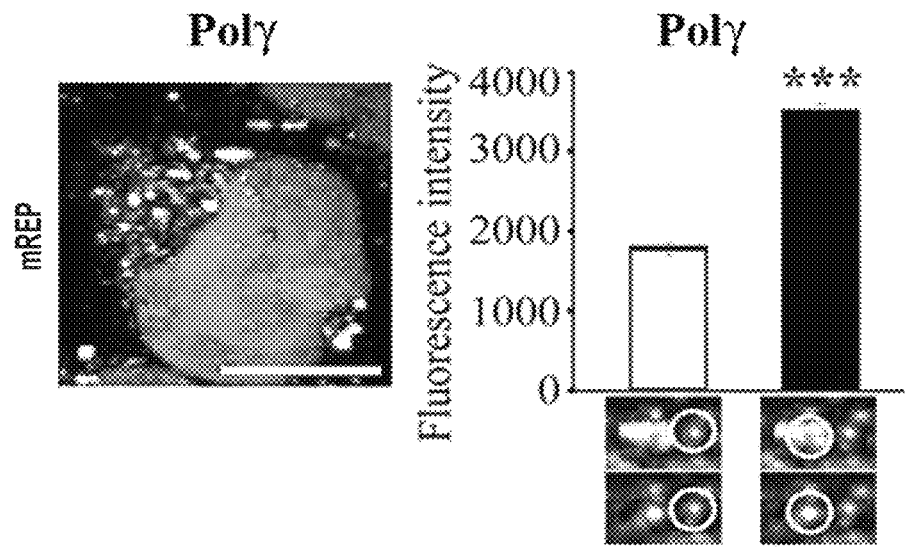
Figure 3E:
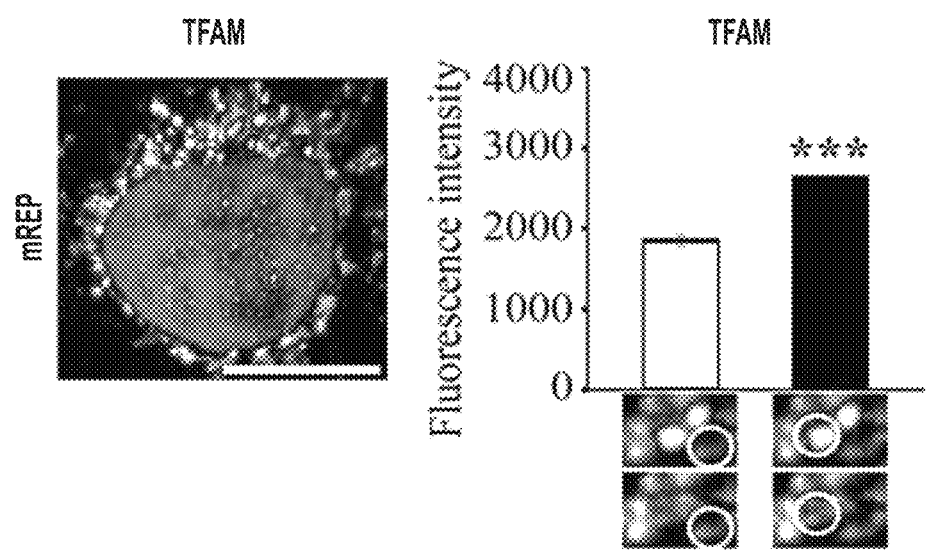

Since the DNA region labelled by mREP is normally present in the genome of all mitochondria, the inventors have reasoned that 3D-FISH/mTRIP labelled only mitochondria where this DNA region was structurally accessible, because of initiation of DNA replication ($O_H$ origin) nearby. To assess whether this was the case, immunostaining of DNA polymerase γ (Polγ), the enzyme responsible for replication mtDNA, was coupled to 3D-FISH/mTRIP. mREP is associated with nucleoids that contain factors involved in DNA replication and transcription. mREP labelling coupled to immunofluorescence with Polγ or TFAM showed that this was the case (74.4±2.5% colocalization of mREP with Polγ, and 71.7±1.5% with TFAM; FIGS. 3D-E), and also that most of the mREP foci were preferentially localized to Polγ and TFAM rich areas (FIG. 3D-E). Moreover, it was found that the intensity of fluorescence of Polγ almost doubled in areas labelled with mREP compared to mREP-negative areas (cells n=30; mt areas n=300, FIG. 3d). Furthermore, mREP-positive mitochondria were associated with higher levels of TFAM immunolabelling compared to mREP-negative mitochondria (FIG. 3e). TFAM is a protein implicated both in transcription of mtDNA and in binding to the mtDNA, and whose levels are correlated with increased mtDNA[14].

mREP Labelling Precedes the Increase of mtDNA Content

Figure 12A:
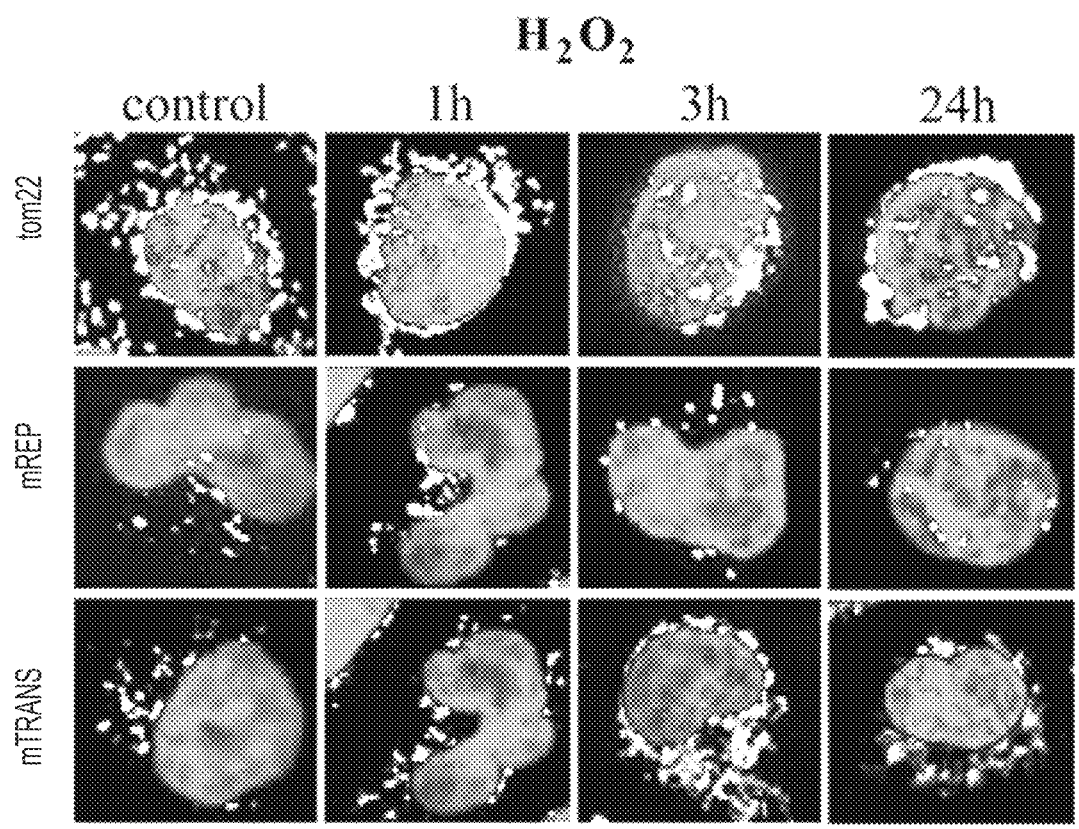
Figure 12B:
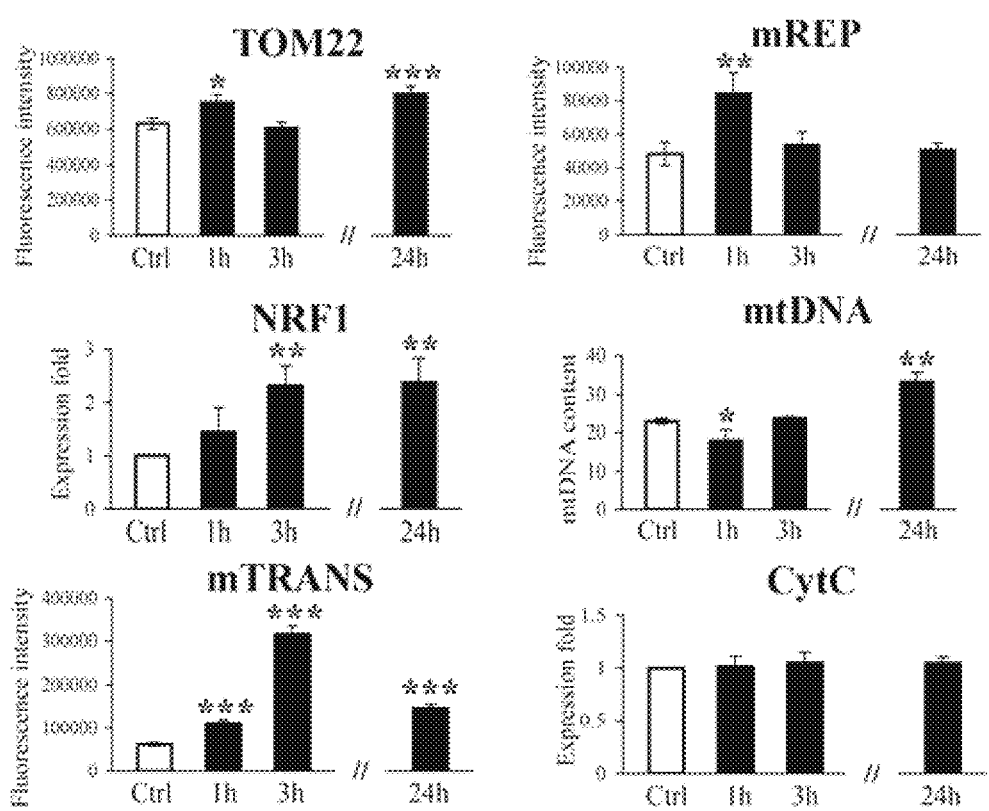
Figure 12D:
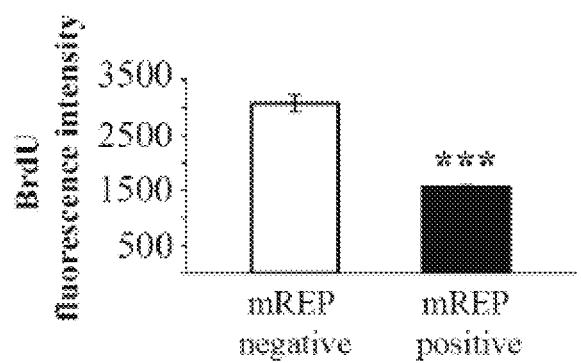

The inventors have reasoned that if mREP labelling is an indicator of mtDNA initiation of replication, it should anticipate the increase in mtDNA content. To assess whether is was the case, HeLa cells were treated in culture with low doses (50 µM) of $H_2O_2$, known to increase the mtDNA copy number and the mitochondrial mass[38]. As expected, treatment with H2O2 resulted in an increase of about 30% of the mitochondrial mass, measured by the intensity of fluorescence of the mitochondrial protein TOM22, and in the increased expression of the mitochondrial biogenesis marker Nrf1 (FIG. 12 a,b). It was observed that mREP labelling increased by about 70% 1 h after treatment, when the DNA content was low probably due to the stress of the treatment, and returned to control values 3 h after treatment when the original mitochondrial DNA content was restored. At 24 h, at high mtDNA content, mREP labelling was as low as in untreated cells. Thus, mREP labelling increased when the mtDNA content was low and returned to original values when the mtDNA content was elevated. Moreover, mREP labelling was followed by a rise in the mtDNA content within 2 hours, compatibly with the time necessary to replicate the mt genome (about 92 minutes for total mtDNA replication[39]), supporting the notion that mREP detected the initiation of mtDNA replication. Under low doses of $H_2O_2$ we also observed an increase of mitochondrial but not nuclear transcription, measured by labelling with the mTRANS probe and CytC expression, respectively.

Furthermore, the inventors have checked BrdU incorporation (10 µM BrdU for 24 h), an indicator of DNA replication, in mitochondria. It was found that mREP-positive entities co-labelled with BrdU, confirming that mREP labelled mitochondria engaged in DNA replication. Importantly, mREP labelled only a subset of BrdU-positive mitochondria, indicating that mREP did not detect extensive or completed replication of the complete mt genome but rather a special event corresponding to initiation of DNA replication. All together these data support the notion that mREP is as a marker of the initiation of mtDNA replication.

In this context, the intensity of BrdU labelling was lower in mREP-positive compared to mREP-negative areas, in agreement with the limited incorporation of a nucleotide analogue at the beginning of replication of the mitochondrial genome. Taken together, these results, and the unique characteristics of the region of the mtDNA recognized by mREP, support the notion that mREP marks initiation of replication.

Whether DNA synthesis proceeds from $O_H$ until the end of the H-strand, or terminates earlier, leading to the formation of the 7S strand and thereby of the D-loop, was not resolved by FISH labelling alone. To assess whether mREP signal indeed corresponds to the labelling of mtDNA or of 7S DNA, or both, the inventors compared endogenous levels of these DNAs by real-time qPCR, as described previously (Antes et al. 2010), in untreated cells and in cells treated with low levels of $H_2O_2$, ad described above. The inventors found that the variations observed in the mtDNA content after exposure to $H_2O_2$ and associated with changes in mREP levels (previously evaluated in the 12S region of the mtDNA are compatible with variations of the mtDNA and not of 7S DNA, which levels keep increasing after the mREP signal returns to normal 3 h after treatment. Thus, although mREP may label both the productive and the abortive initiation of mtDNA replication (formation of the D-loop), variations in mREP are compatible with productive replication of the mtDNA rather than with the formation of the D-loop.

Only a Fraction of Mitochondria are Engaged in Initiation of DNA Replication and/or in Transcription Detected by mTRIP To assess the fraction and the distribution of mtDNA processing activities (i.e. mtDNA transcription and replication) within the mitochondrial network the inventors performed colabelling with mREP, mTRANS, and TOM22. Notably, 58.9±2.7% and 12.9%±1.3% of the mitochondrial mass (TOM22 immunolabelling) colabelled with mTRANS and mREP respectively. Therefore, a significant fraction of the mitochondria were not labelled with either probe indicating that either they are not involved in the transcription of the tested genes and/or in the replication of mtDNA, or that the levels of the target molecules are not detectable with this approach. In addition, 71.3±2.9% of foci labelled by mREP also carried mTRANS transcripts whereas only 8.5±0.8% of foci carrying mTRANS were also mREP-positive. These results reveal that the majority of mitochondria involved in the initiation of replication also carried mTRANS transcripts, whereas only a minority of mitochondria that carried detectable transcripts were also involved in initiation of mtDNA replication in these cells.

Heterogeneous Labelling of the Regulatory D-Loop Region in Mitochondria within Single Cells The inventors reasoned that if mTRIP can identify distinct mitochondrial populations within single cells according to the DNA engaged in initiation of replication and to the transcript content, it should also identify mitochondria with distinct RNA and DNA labelling patterns in the regulatory region, which may be fonctional to the regulation of mtDNA itself. To assess this point, the inventors performed FISH with three probes located in the D-loop region (probes PL-OH and 7S) and at promoters of the H-strand ($P_{H1}$ and $P_{H2}$; probe PH1-2), FIG. 15B. They performed single labelling and colocalization experiments with two probes in the presence and in the absence of nucleases. Quantitative analyses of fluorescence showed that probe PL-OH, located downstream of mREP in the direction of DNA replication, and which includes the $P_L$ and the $O_H$ regions, labels accessible DNA structures (DNaseI-sensitive labelling, FIGS. 15 A and C), which might be part of the $P_L$ transcription bubble, or of the $O_H$ replication bubble, or of both. This last possibility is in agreement with a large set of evidences indicating that transcription from $P_L$ is coupled to H-strand replication (Scarpulla 2008).

Probe PL-OH also labels RNA in RNA/DNA hybrids (reduction of labelling in the presence of RNaseH, FIGS. 15 A and C). These RNA molecules might consist of R-loops, i.e. the RNA primers for DNA synthesis for the $O_H$ origin (Brown et al. 2008), present as processed as well as unprocessed molecules of various lengths, or regular L-strand transcripts, or both. Interestingly, simultaneous treatment with DNAseI and RNaseH resulted in residual labelling (19.89%±1.4%) that disappeared when cell were also treated with RNAseA (FIG. 15A). This experiment indicates that probe PL-OH also labels RNAseH-resistant RNA/DNA hybrids, which RNA becomes accessible to RNaseA after the DNA moiety is removed by the action of DNaseI. This finding is in agreement with the notion that the structure of the RNA/DNA hybrids in R-loops may confer resistance to RNaseH (Brown et al. 2008). An increase in the intensity of labelling in the presence of RNaseA indicates that not only RNA is not a significant target of PL-OH but also that RNA molecules to a certain extent inhibit the labelling of the other targets.

More detailed information on the heterogeneity of the nucleic acids composition of the D-loop region in mitochondria was provided by the direct observation of foci (FIG. 15 C). Indeed, PL-OH labelling consists of small foci with poor fluorescence intensity as well as of large foci of intense fluorescence, and distinct colocalization patterns with the other probes. The large PL-OH foci, which are mostly DNaseI-resistant and RNaseH-sensitive (FIG. 15 A), essentially colocalize with foci of the downstream 7S probe located within the 7S region (FIG. 15 A, lower panels). Differently from PL-OH, however, large 7S foci are essentially RNaseH-resistant. Thus, PL-OH and 7S large foci colocalize but the former probe recognizes RNA/DNA hybrids whereas the latter recognizes RNA. This pattern is compatible with the labelling of transcripts bound to the DNA template proximally to the promoter (probe PL-OH), and of single-strand RNA distally from the promoter (probe 7S, FIG. 15 C), although the limits of resolution of FISH do not define whether labelled nucleic acids are present on the same molecules. In addition to this prevalent type of labelling, large DNaseI-resistant 7S foci and apparently DNaseI-sensitive PL-OH foci were detected (pattern 3 in FIG. 15 C), which are compatible with the decreased PL-OH signal in the presence of DNaseI. These foci reveal accessible DNA structure at the level of PL-OH whereas RNA is present at the level of 7S. Moreover, RNaseH-resistant PL-OH and 7S foci were observed (pattern 5 in FIG. 15 C), which consist either of RNAseH-resistant RNA/DNA hybrids at one or both loci or of DNA (PL-OH) and RNA (7S). The heterogeneity of mTRIP labelling in this region within single cells is summarized in FIG. 15D.

Figure 15A:
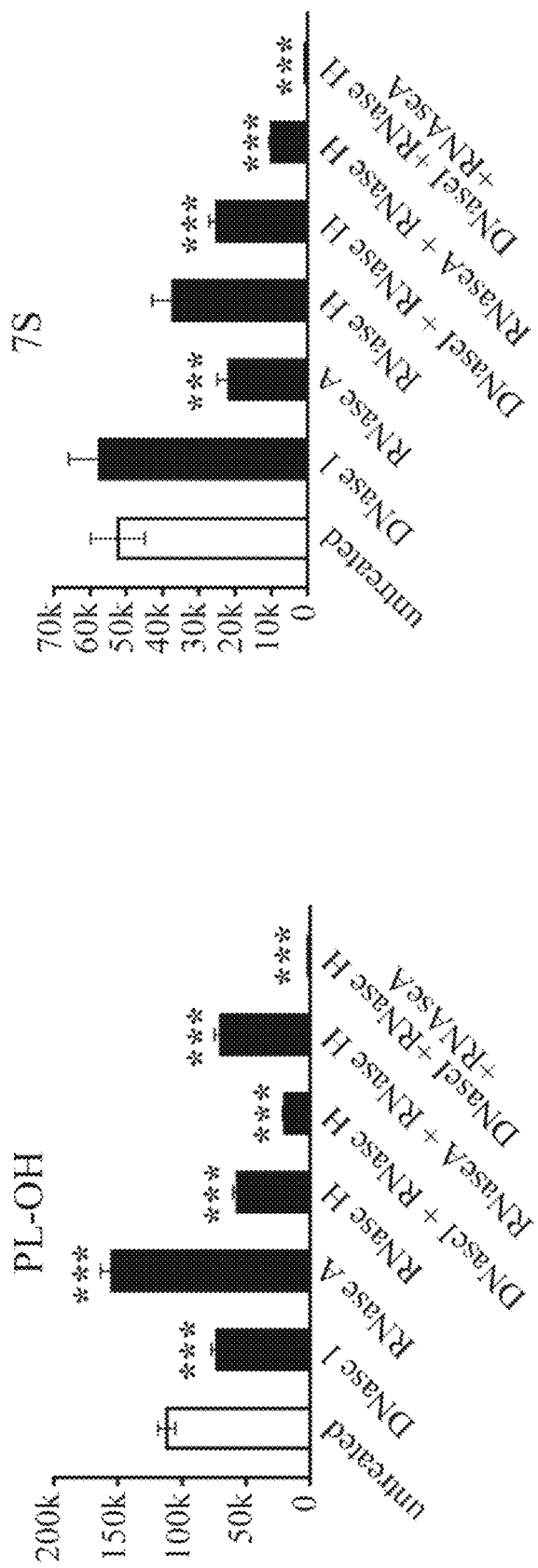
Figure 15B:
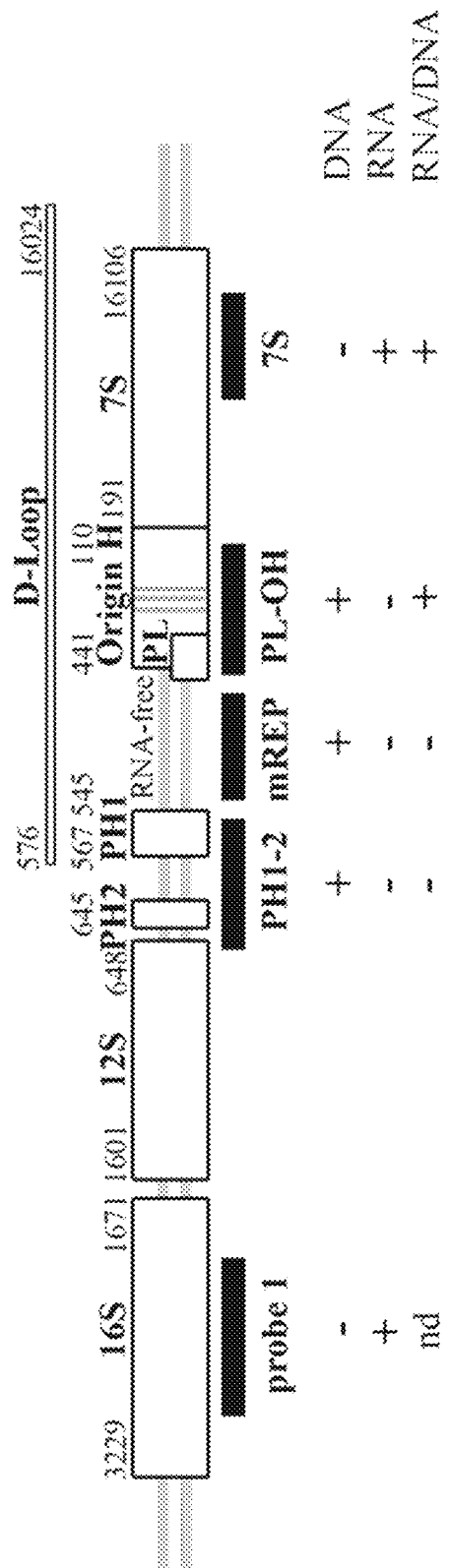
Figure 15C:
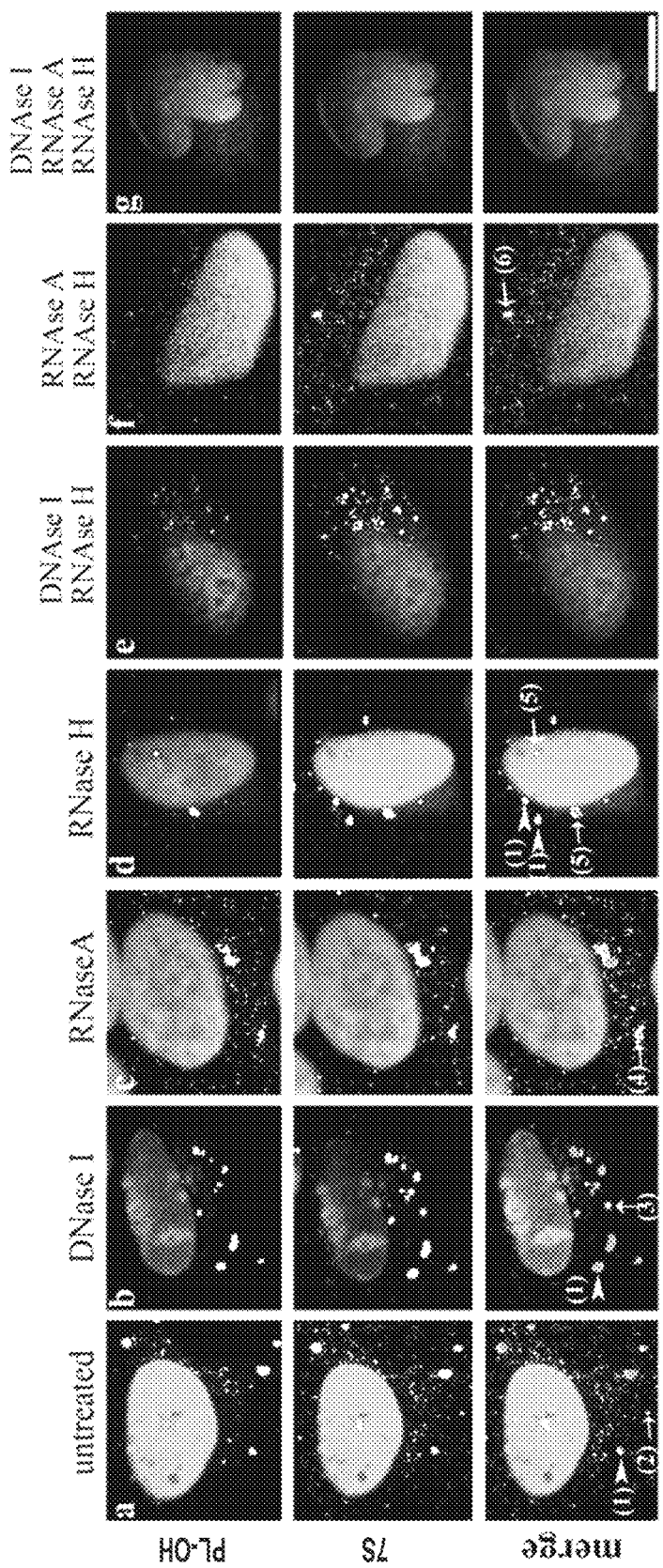
Figure 15E:
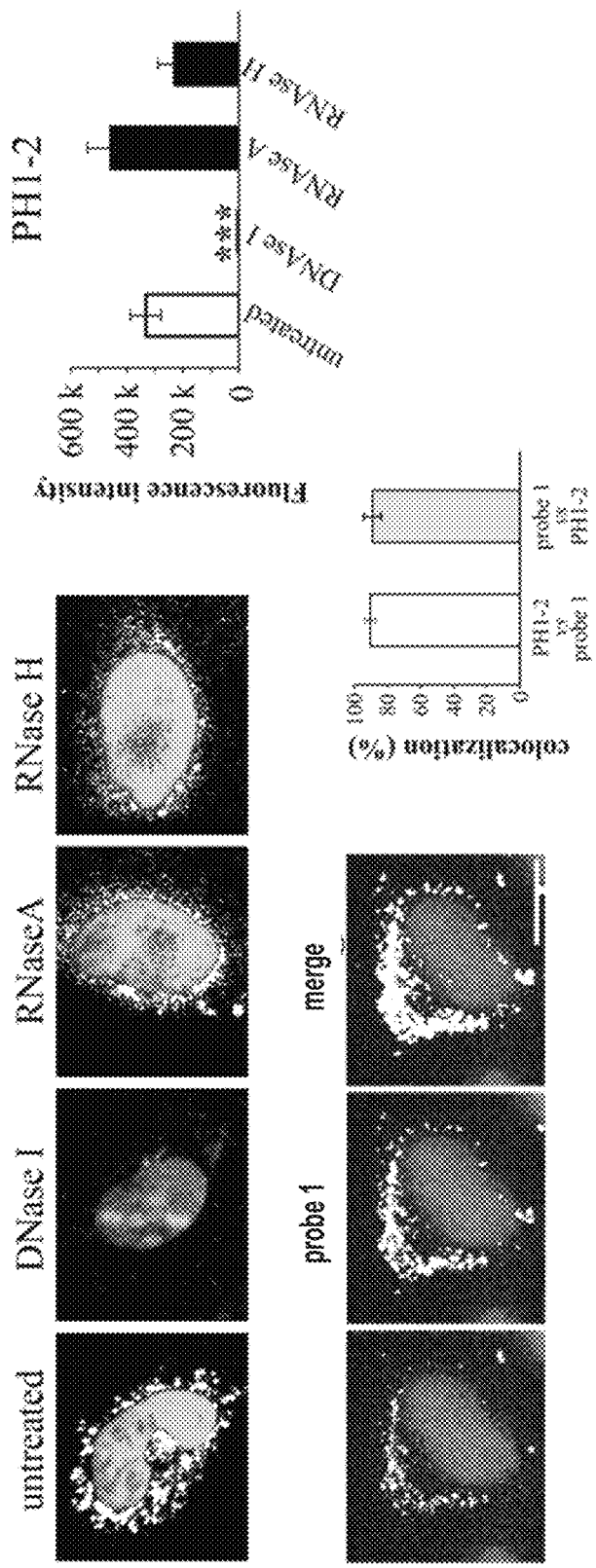
Figure 15F:
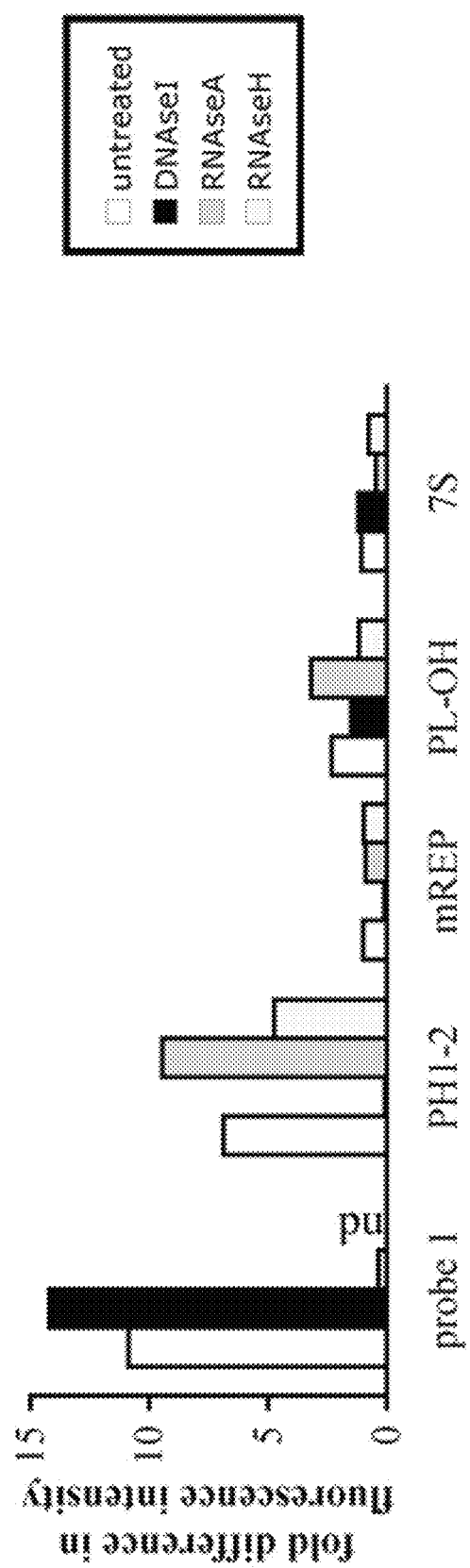

Since treatment with RNaseA did not reduce the labelling with probe 7S to background levels, this probe likely binds other targets than just RNA. Indeed simultaneous treatment with RNAseH and RNaseA resulted in significant decrease of the signal, compared to RNaseA alone (p=0.0013), indicating that some RNA/DNA hybrids were recognized by probe 7S (FIG. 15A).

Figure 4A:
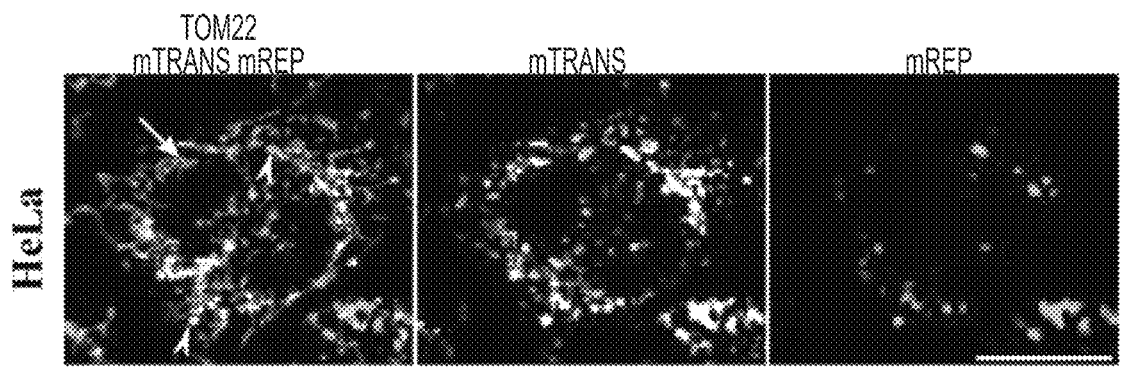
FIGS. 4A to 4C. 3D-FISH reveals mitochondria lacking transcription and initiation of replication activity. (a) 3D-FISH/mTRIP reconstructed HeLa cell also immunolabeled for the mitochondrial protein TOM22 reveals simultaneously mtDNA, mtRNA and the mitochondrial network. Right panel: mREP; middle panel: mTRANS; left panel: merge. In the left panel, mitochondrial transcripts (mTRANS, red, see arrow) are detected as independent entities in the mitochondrial network (anti-TOM22, green), whereas the mt initiation of replication units (probe mREP, blue) essentially colocalize with the transcript carrying units (merge, purple, see arrowheads).
Figure 4B:
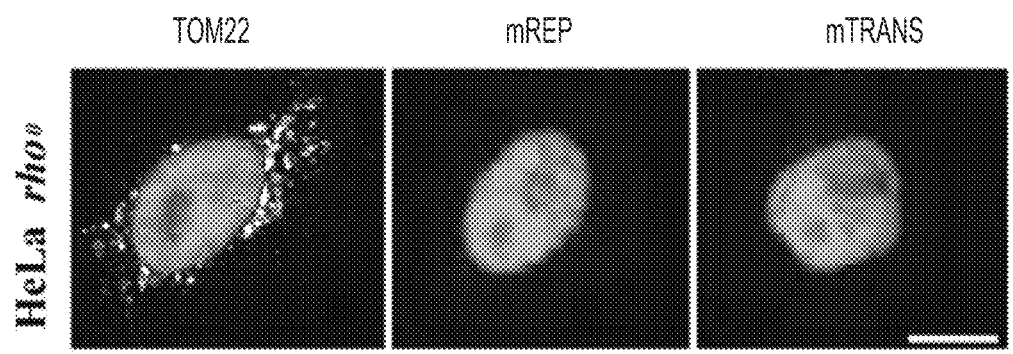
Figure 4C:
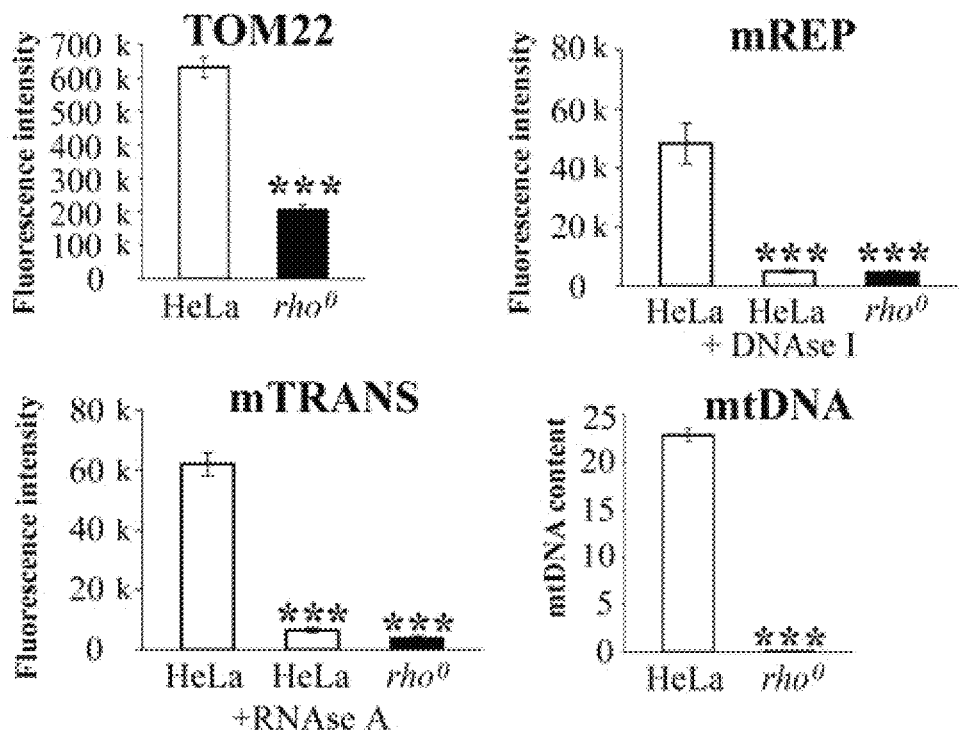

Interestingly, large PL-OH and 7S foci which were greatly reduced in number after treatment with RNaseA alone, essentially disappeared after treatment with RNaseA and RNaseH (FIG. 4C), indicating that RNA is essential to the structures identified by these foci, and that PL-OH and 7S foci are linked. Moreover, large PL-OH and 7S foci disappeared after simultaneous treatment with RNAseH and DNaseI whereas treatment with DNaseI had essentially no effect, and treatment with RNaseH affected only PL-OH foci. This experiment indicates that the RNA and the DNA moieties of RNA/DNA hybrids, at least at the level of 7S, are essential to the formation not only of the structures labelled by probe 7S but also of the structures labelled by probe PL-OH, further supporting the notion that the nucleic acids labeled by the two probes are linked.

Interestingly, in the presence of two nucleases, the disappearance of large PL-OH and 7S foci was replaced by the appearance of small foci (RNaseA and RNaseH) or of foci of reduced size (DNAseI and RNAseH), which displayed some colocalization (FIG. 15D). However, differently from large foci, most other foci did not colocalize indicating that in these cases the nucleic acids labelled by the two probes are not linked.

Importantly, only a limited fraction of mitochondria were labelled with probes PL-OH and 7S (colabelling with mTOT, not shown), indicating that in this regulatory region nucleic acids were not accessible or were accessible below detectable levels in non-labelled mitochondria. Finally, colocalization experiments revealed that not only PL-OH colocalizes by 99.44%±0.05% with 7S, thereby further supporting the notion of a link between the nucleic acids labelled by the two probes, but also that mREP colocalized with 7S by 99.33%±0.07%. This result indicates that mREP, PL-OH and 7S likely label linked although heterogeneous nucleic acid structure(s). Conversely, the majority but not the totality of 7S colocalizes with mREP (59.8%±2.6%), and with PL-OH (69.7%±2.7%), indicating that 7S also labels RNA that is not involved in the structure linked to initiation of replication, compatibly with labelling of L-strand transcripts. In agreement with this notion, the intensity of labelling with PL-OH was 2.3-fold higher than with mREP, compatibly with PL-OH targeting not only DNA in the replication bubble but also transcripts.

In conclusion, probes PL-OH and 7S, identify in a fraction of mitochondria a variety of structures with distinct nucleic acid composition that appear associated with $O_H$ DNA replication and L-strand transcription and that coexist in single cells.

mtDNA Transcription Dynamics in the $P_H$ Promoters Region at the Single Cell Level On the other side of mREP, probe PH1-2, which is located in the region of promoters $P_{H1}$ and $P_{H2}$ (FIG. 15B) is completely sensitive to DNaseI, indicating that it labels essentially DNA (FIG. 15 E). The accessible DNA in this region might result from its opening as a consequence of the nearby $O_H$ replication bubble, or represent the $P_{H1}/P_{H2}$ transcription bubble. The overwhelming colocalization between probe PH1-2 and probe 1, which labels 16S RNA transcribed essentially from $P_{H1}$, (FIG. 4 E) supports the second notion. Moreover, the elevated intensity of fluorescence observed with probe PH1-2, which is compatible with the signal detected with probe 1 (FIG. 4 F), indicates that probe PH1-2 labels DNA in the transcription bubble formed at $P_{H1}$ for the aboundant transcription of rRNAs. Treatment with either RNaseA or RNaseH does not significantly alter the efficiency of labelling, although foci have a different aspect compared to untreated controls, indicating that although RNA and RNA/DNA hybrids do not appear to bind this probe, they might affect the structure of the DNA to which the probe binds.

A large difference in the extent of labelling among probes located in the regulatory region of mtDNA was noted. PH1-2 fluorescence intensity was 6.9-fold higher than mREP, and probe 1 fluorescence intensity, which marks the 16S transcript was 10-fold higher, compatibly with robust transcription of rRNAs (FIG. 15 F). Simultaneous labelling with two probes reveal that 48.73%±3.44% of mREP foci colocalize with PH1-2 foci, indicating that although in certain cases accessible DNAs in these two regulatory regions may be linked, in other cases it is not, compatibly with the notion that transcription of rRNA can be uncoupled from the formation of the DNA structure that promotes replication in the $O_H$ region.

These data are consistent qualitatively and quantitatively (intensity of fluorescence, FIG. 15 F) with the expected replication and transcription activities of the regions examined (Chang and Clayton 1985; Clayton 1991; Falkenberg et al. 2007; Scarpulla 2008). These findings also provide novel information on concomitant DNA replication and transcription activities in the regulatory region of mtDNA in single cells.

C. Discussion

Understanding the dynamics of DNA transcription and replication within the mitochondrial network is essential to assess mitochondrial function. Mitochondria appear to be homogeneous as a population within single cells, although functional differences have been described for synaptic and non-synaptic mitochondria in neurons[20]. The inventors have devised here a novel 3D-FISH approach which identifies a variety of mitochondrial populations in single-cells. These populations differ in the intracellular localization, in the relative amount of transcript that they carry and in their engagement in initiation of DNA replication and in the signal of the regulatory region of mtDNA, indicating that mitochondria are more heterogeneous than previously thought in DNA processing activities.

The novel FISH protocol (mTRIP) described herein identifies a unexpected variety of mitochondrial populations with distinct properties within single-cells. These populations differ in their intracellular localisation, in the relative amount of transcripts that they express, in the initiation of DNA replication, and in the signal of the regulatory region of mtDNA indicating that mitochondria exhibit a greater level of heterogeneity in DNA processing activities than reported previously, including mitochondrial dynamics during mtDNA synthesis (Davis and Clayton 1996). Only 16S rRNA appears to label most of mitochondria, and this with an elevated signal per unit, but all other probes identify distinct and occasionally minor mitochondrial fractions. Within the limits of resolution of this approach, labelling of mtDNAs and RNAs was also shown to be correlated with nucleoids, the mitochondrial substructures involved in mtDNA processing. The inventors observed different levels of colocalization between FISH and nucleoid markers, in agreement with the different amounts of regulatory proteins found in nucleoids and which might have regulatory functions (Chen and Butow 2005; Spelbrink 2010; Shutt et al. 2011).

The 3D-FISH method described herein detected mitochondria and mitochondrial substructures rich in a given transcript, that was present as a processed molecule, a polycistronic RNA, or bound to the DNA template, the latter likely resulting from ongoing transcription. Moreover, RNAseH treatment revealed the presence of another class of transcripts (accounting for 38% of additional signal) that were still bound to the DNA template and likely resulted from ongoing transcription. The variety of RNA molecules labelled by 3D-FISH, which also included truncated and misprocessed transcripts, provided more extensive information compared to full-length transcripts detected by RT-qPCR. Moreover, the 3D-FISH method described herein permitted the detailed investigation of mtDNA dynamics, since it labelled relevant mitochondria in single-cells, whereas RT-qPCR only assessed the transcript levels of entire mitochondrial and cellular populations.

In general, the inventors found a good correlation between RNA levels detected with mTRIP and RT-qPCR, thus validating the FISH approach described herein which allows assessing mitochondrial transcripts within the mitochondrial network in individual cells.

With these novel tools the inventors have found that, unexpectedly, of the two rRNAs produced from the same PH1 promoter[11], 16S, but to a lesser extent 12S, is abundant in mitochondria. RT-qPCR data confirmed the 3D-FISH finding, and this was the case in both HeLa cells and primary fibroblasts. Importantly, variable levels of 16S versus 12S rRNA were detected in liver cells[21] and, in their adenylated form, 16S RNA was more abundant than 12S RNA in the skeletal muscle[22], indicating that lower levels of 12S versus 16S RNA detected with the present analysis, represented a physiological situation.

Importantly, it was observed that mtDNA processing was not alike in all cell types. It was found that in HeLa cells mitochondria carrying abundant transcripts (16S, ND1 and and to a certain extent ATP8) were mainly located in the perinuclear region, whereas the less abundant transcripts of the last third of the H-strand appeared progressively distributed in the cytoplasm and in more fragmented mitochondrial entities. The perinuclear localisation of mitochondria may be required for the nuclear uptake of molecules necessary for intensive mitochondrial transcription and/or DNA replication, or for buffering $Ca^{2+}$ fluctuations from the cytoplasm[23]. However, perinuclear localization of mitochondria has been also described in cells of patients with myopathic and neurodegenerative diseases characterized by mitochondrial dysfunctions[24,25]. In this context, it was interesting to note that perinuclear distribution of most mitochondria, and in particular of the organelles that produce the predominant 16S RNA, was not observed in primary fibroblasts, thus raising the possibility that such localization is associated with mitochondrial impairment. Additional differences characterize mitochondrial DNA in primary cells versus cancer-derives cell lines. The 3D-FISH method described herein detected high levels of ND1 RNA in HeLa cells but not in primary fibroblasts. This transcript was present probably as polycistronic RNA consequent to leaky termination from promoter PH1, indicating that mitochondrial rRNA transcription termination may be altered in HeLa cells.

Labelling of DNA by the 3D-FISH method described herein appears limited to locally open structures, as in transcription complexes after disruption of the RNA moiety, and in DNA engaged in initiation of replication. Interestingly, a third mitochondrial replication origin previously detected with atom force microscopy and expected to be activated only occasionally[13] was revealed in the experiments that were conducted and its position in the mitochondrial genome defined at a higher resolution. To date, identification of mitochondrial initiation of replication in single cells has been elusive. Importantly, the inventors have defined the characteristics necessary for a probe to specifically mark the initiation of DNA replication, and proposed a specific probe, mREP, which is an efficient marker of initiation of mtDNA replication. Mitochondria engaged in DNA replication could therefore be detected and analysed in cells and under experimental conditions of biological relevance.

The combination of mtDNA transcription and initiation of replication labelling can provide information on mitochondrial dynamics in a variety of physiological processes. (e.g., the dynamics of mitochondrial DNA transcription and replication during the cell cycle, Chatre & Ricchetti, in preparation). Moreover, the 3D-FISH method which is described herein can provide novel information on alterations of mtDNA dynamics and represents a novel tool which can impact on disease screening related to the mitochondrial function.

Investigation of mtDNA regulatory regions by mTRIP identified DNA, RNA, and RNA-DNA hybrids at the expected locations according to current knowledge on global mitochondrial populations (Chang and Clayton 1985; Clayton 1991; Falkenberg et al. 2007; Scarpulla 2008), thus further validating this approach, which however operates at the single-cell level. Indeed colocalization between probes pairs reveals structures that contain accessible DNA upstream of the replication origin and comprising the promoters $P_L$ on one side and $P_{H1}$ and $P_{H2}$ on the other side. Conversely, RNA is the almost exclusive target in the 16S region, as expected for the $P_{H1}$ transcript, and in the 7S region where it probably represents the L-strand transcript. RNA/DNA hybrids are detected at the level of the $P_L$ promoter compatibly with the formation of R-loops, that provide the RNA primers for DNA replication, and also at a minor extent at the level of 7S where they mat represent L-transcripts bound to the DNA template. Moreover, the intensity of colocalization among probes reveals comparable levels of labelling for the region mREP, that according to our experiments indicates initiation of replication, and the region that that comprises the $O_H$ replication and the downstream 7S transcript, in agreement with the notion that L-strand transcription and replication are coupled. Our data suggest that these two processes are not only temporally but also quantitatively linked. In addition to these aspects, our findings provide novel information on the dynamics of the key regulatory regions of the mtDNA within the mitochondrial populations.

First, accessible DNA in the $O_H$ replication origin and L-strand promoter may be linked to accessible DNA in the H-strand promoters (about one half of the relative signals colocalize), whereas the two types of events appear uncoupled for the remaining half of the signal, indicating that in these cases rRNA transcription is not linked to $O_H$ replication/L-strand transcription. Colocalization between these foci and mREP foci (mREP is located in the middle of the opposite promoters $P_L$ and $PH_{1-2}$, and also upstream of the main replication origin $O_H$) suggest that rather than being a passive region, mREP appears as an indicator or a key regulator region not only of the main replication origin, but also of transcription of both the H- and the L-strands.

Furthermore, mTRIP identifies within a single-cell a variety of labellings that include a prevalent pattern, and also distinct patterns that show either higher levels of accessible DNA at the level of the origin of replication, or RNAseH resistant structures at the level of the origin of replication, or else DNA labelled at the level of the transcription of 7S, compatibly with the activities expected at these foci.

In conclusion, by mTRIP the dynamics of mtDNA transcription and initiation of replication are exposed with unprecedented resolution at the single-cell level, which may help in further elucidating the link between mitochondrial transcription and replication, and which may be used for future investigations of mtDNA processing under physiological and pathological conditions.

D. Conclusion

Mitochondrial DNA (mtDNA) replication and transcription are crucial for cell function, but these processes are poorly understood at the single-cell level. By modified fluorescence in situ hybridization, called 3D-FISH, the inventors have identified mitochondria engaged in initiation of DNA replication in human cells. Mitochondria were also distinctly marked according to transcription profiles. Thus, the inventors have documented the existence of mitochondrial subpopulations in single cells according to the prevalent mtDNA processing activity, indicating that mitochondria may not be functionally alike. Importantly, the inventors have proposed an in situ hybridization procedure, and more particularly a 3D-FISH protocol that can be coupled to immunofluorescence, and they were thus able for the first time to monitor mtDNA, mtRNA and proteins simultaneously in single cells and demonstrate significant heterogeneities that have been previously missed. With this approach, novel information can be provided on the dynamics of mtDNA processing during physiological and pathological processes. These findings have implications for the optimization of diagnostic tools for mitochondrial diseases, in particular those involving mtDNA depletion and mtDNA loss.

Since currently available tools including recent improvements[7], cannot identify mitochondria engaged in DNA replication, they cannot discriminate the transcription profiles of organelles in single cells. Moreover, although sequential RNA and DNA labelling[8], as well labelling of either RNA or DNA, and proteins[9, 10] have been performed, immunofluorescence was not directly coupled to FISH to simultaneously detect proteins and mitochondrial DNA and RNA. Thus, proteins of interest could not be monitored during mtDNA transcription and replication. As a consequence, it remained unclear how mtDNA processing is coordinated among the many organelles present in each cell and whether this process is deregulated in subpopulations during disease. Using a novel approach, the inventors have identified mitochondrial subpopulations engaged in the initiation of mtDNA replication and in RNA processing, and assessed their dynamics in single cells. Theses findings revealed significant heterogeneities within single cells that have been missed previously, and this can impact on how mitochondrial functions are assessed. Mitochondria with altered processing of DNA and RNA, as in diseases involving mtDNA loss, can be identified with this novel approach.

E. Applications

The present invention is of particular interest for analyzing the processing of DNA, RNA or metabolites in cell(s) or tissue(s), and/or analyzing the dynamics of said cell(s) or tissue(s), and/or detecting specific diseases.

As stated above, mitochondrial misfunction is associated with a variety of diseases (cancers, myopathies, neuropathologies, infections), and with the ageing process, and can be found in a number of mitochondrial diseases.

Mitochondrial diseases are diagnosed in 11.5/100 000 adults and children per year in the world (~800 000 patients/year), and 1/4 000 (25/100 000) USA children.

Mitochondrial diseases are difficult to diagnose. Referral to an appropriate research center is critical. If experienced physicians are involved, however, diagnoses can be made through a combination of clinical observations, laboratory evaluation, cerebral imaging, and muscle biopsies. Despite these advances, many cases do not receive a specific diagnosis.

Most hospitals do not have a metabolic laboratory and therefore can run only the most basic tests. In addition, a single blood or urine lab test with normal results does not rule out a mitochondrial disease. This is true for organic acids, lactic acid, carnitine analysis and amino acid analysis. Even muscle biopsies are not 100% accurate.

To date, most of the studies on mitochondria are based on molecular biology assays (PCR, qPCR, Southern blot), biochemistry (Western blot, ATP/Reactive Oxygen Species (ROS)/membrane potential detection assays), and electron microscopy (for the mitochondrial ultrastructure).

For example, current diagnostic tools for the mitochondrial diseases encompass Metabolic Screening in Blood and Urine (complete blood count, lactate, pyruvate, plasma amino acids, liver enzymes, ammonia, urine organic acids . . . ), Metabolic Screening in Spinal fluid (lactate, pyruvate, amino acids, cell count, glucose, protein), Characterization of Systemic Involvement (echocardiogram, ophthalmologic exam, brain MRI, electrocardiogram, audiology testing), Clinical Neurogenetics Evaluation (karyotype, child neurology consultation, fragile X test, genetics consultation).

There is therefore a need for simple, reliable and fast methods and tools for including in diagnosis protocols of mitochondrial diseases and mitochondrial dysfunctions.

In addition, fluorescence imaging tracks separately mitochondrial DNA (mtDNA), mitochondrial RNA (mtRNA), by fluorescence in situ hybridization (FISH), and proteins, by immunofluorescence (IF), in fixed cells. However, two aspects restrain the potency of fluorescence imaging of mitochondria. First, even using a combination of different imaging procedures (for instance IF and RNA FISH, or IF and DNA FISH, of RNA and DNA FISH), it is not possible to detect in the same cell DNA, RNA and proteins. This can be due to cross-reaction of chemicals and damages of the samples during the procedure(s). For example, when IF and FISH are combined, FISH provokes damages to the proteins resulting in a reduced fluorescence signal for the proteins that cannot be interpreted correctly. Second, the prior art FISH procedure for the detection of mtDNA contains large DNA probes (i.e. more than 3 kbp), which generate high levels of a specific staining and thus decrease the overall resolution.

Therefore, the development of a novel FISH labeling approach of cells that allows the tracking of mitochondrial DNA initiation of replication at the single-cell resolution is of particular interest to reveal dysfunctions at this level. In addition, the present invention further allows the simultaneous detection of mitochondrial RNA, and thus the monitoring of transcription events. Bi-dimensional or three-dimensional imaging can also be performed. Moreover, since the developed FISH procedure does not damage the epitope/antigen, it permits also the simultaneous analysis of mitochondrial and/or cellular proteins. In its 3D version, this technique has been called called 3D-Fluorescence In Situ Hybridization coupled ImmunoFluorescence (3D-FISH coupled IF) and results in a drastic modification of the classic FISH procedure in term of cell fixation, permeabilization, mtDNA probes design, size and fluorescence labeling, cell and DNA probes denaturation.

Moreover, although the depletion of mitochondrial DNA is currently detected by real time quantitative PCR on biopsies (preferentially muscle biopsies, because of the richness in mitochondria in this tissue and the relatively harmless surgical procedure), these tests only indicate the average mitochondrial DNA content present in the entire mitochondria population, and this in all the cells contained in the biopsy, including non-muscle cells present in the biopsy. By contrast, the present invention enables to detect i) alterations in mitochondrial DNA transcription and replication in any single type of cell, including cells extracted from a buccal sample, which avoids biopsies; ii) the impairment in mtDNA replication and transcription (which are the outcome of the mitochondrial DNA molecule) in a portion or in the totality of mitochondria; iii) the impairment in mtDNA replication and transcription in a specific number or in the totality of tested cells. At present, there are indeed no indications whether mitochondrial depletion disease cells are equally or differently affected in their mitochondrial DNA content and activity. Moreover, the present invention enables to reveal the proportion of mitochondria that display at the same time mitochondrial DNA transcription and replication signal, which indicates efficient cell activity, see FIG. 14. These data might be of interest or directly useful to follow the progression or even anticipate the progression of mitochondrial diseases.

The method of the invention, the probes described herein and kits encompassing said probes or permitting to carry out the method of the invention can also be used in the analysis and detection of neoplasic diseases(s) or cancer(s).

The invention provides means useful for the detection and diagnosis of neoplasic or tumoral cell(s) or tissue(s), and especially to distinguish said cell(s) or tissue(s) among healthy cell(s) or tissue(s).

Further experiments have shown a tight association of mt initiation of DNA replication and mt transcripts in healthy primary cells but not in cancer-derived cell lines (FIG. 14). In these experiments co-labelling with mTRANS and mREP probes (purple spots, FIG. 14)) was performed to reveal the association of mt initiation of DNA replication and mt transcripts. These experiments demonstrated that in HeLa cells about 92% of mitochondrial transcripts were NOT associated with mt DNA replication), and that in primary fibroblasts only about 27% of mitochondrial transcripts were NOT associated with mt DNA replication (n=30, from 3 independent experiments). These results were confirmed in other tumor-derived cell lines and primary fibroblasts (data not shown).

Thus, in tested healthy cells mitochondria that are active in DNA replication were also rich in transcripts (a sign of efficient mitochondrial activity) while in cancer cell lines this occurred only in a small fraction of mitochondria.

Figure 14A:
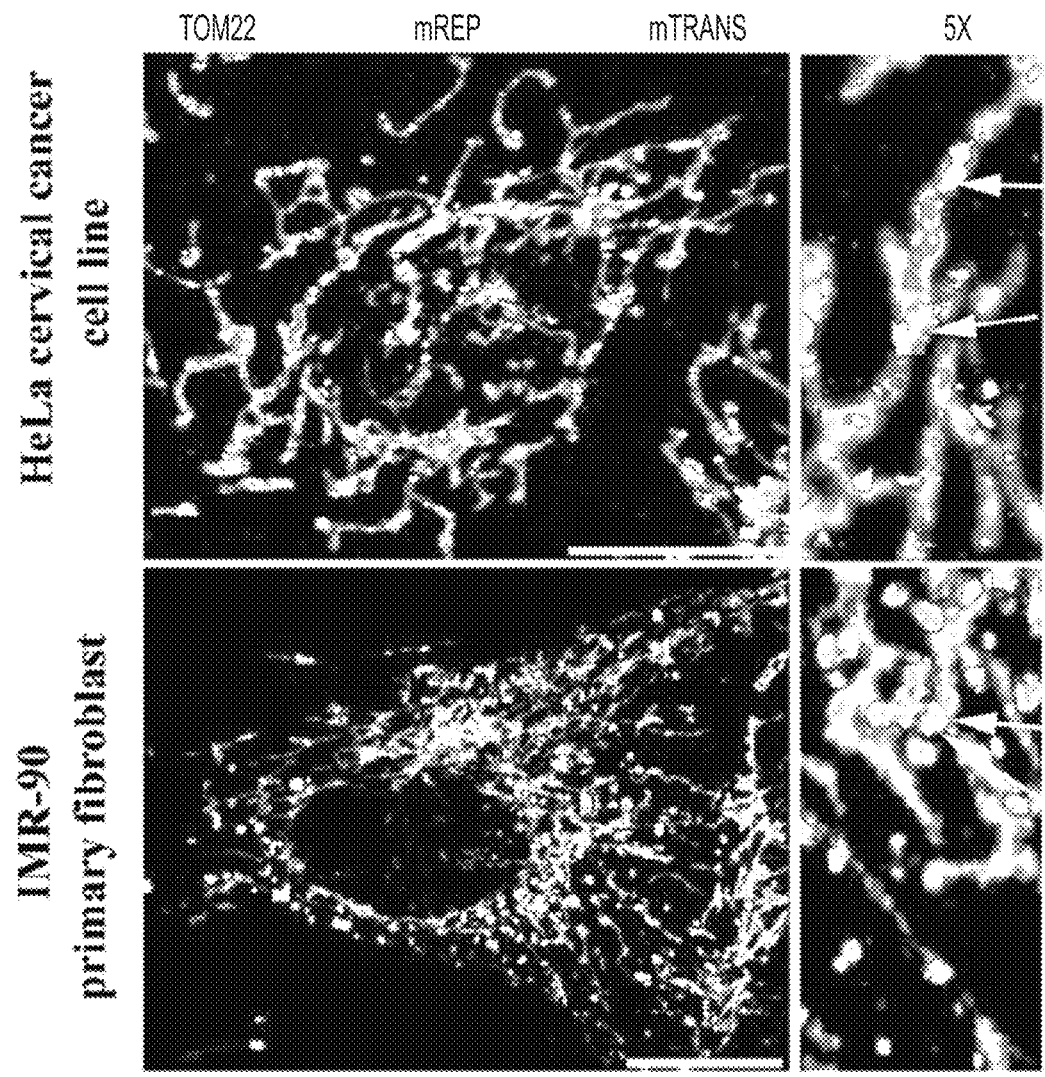
FIGS. 14A to 14E. (A) Experiment disclosing a tight association of mt initiation of DNA replication and mt transcripts in healthy primary cells but not in cancer-derived cell-lines: 3D-FISH/mTRIP-reconstructed HeLa cell (upper panel) and primary human fibroblast IMR-90 (lower panel) also immunolabeled for the mitochondrial protein TOM22. Mitochondrial transcripts (probe mTRANS, red) are detected as independent entities in the mitochondrial network (anti-TOM22, green), whereas the mt initiation of replication units (probe mREP, blue) essentially colocalize with the transcript carrying units (merge, purple). Right panels represent details of the left panels (5× magnification). White arrows indicate purple foci where mTRANS and mREP co-localize (col-localization of transcription and initiation of replication signals). Note that in primary fibroblasts mitochondrial transcripts essentially co-localize with initiation of replication units and are almost not detected as independent units. Scale bar=10 μm. (B) Quantification of co-labelling of either mTRANS or mREP with anti-TOM22 in HeLa cells and IMR-90 primary fibroblasts expressed in percentage of col-labelling. (C) Quantification of co-labelling of mTRANS with mREP (mitochondrial entities carrying transcripts and being involved in initiation of replication) white columns, and of mREP with mTRANS (mitochondrial entities involved in initiation of replication that also carry transcripts), grey columns in Hela cells (left panel) and IMR-90 primary fibroblasts (right panel). For each condition, n=30 cells; three independent experiments. (D) Expression level of mitochondrial transcripts in cancer cells (E) Expression level of mitochondrial transcripts in healthy cells. For each condition, n=30 cells; three independent experiments.
Figure 14B:
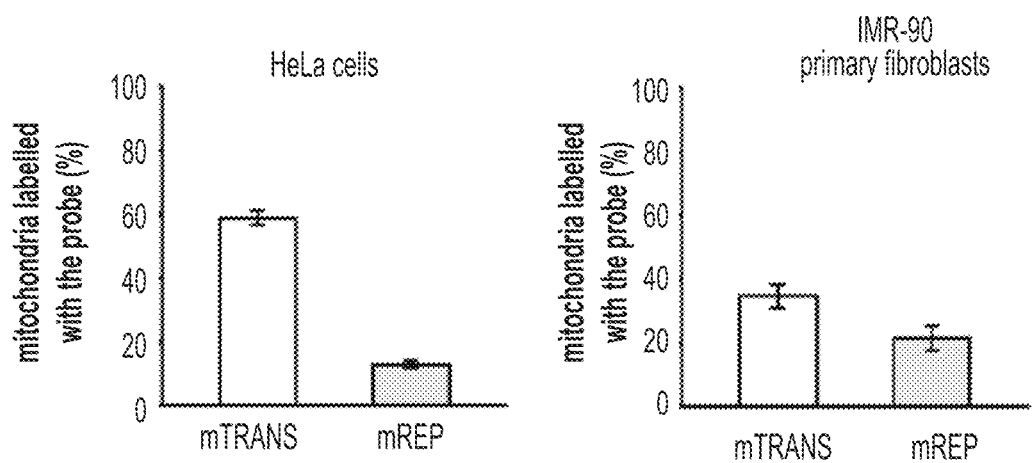
Figure 14C:
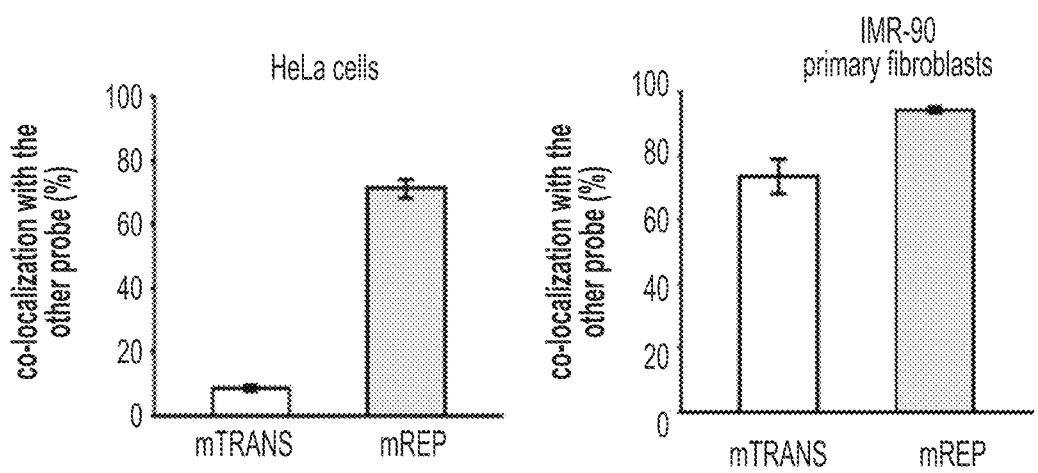
Figure 14D:
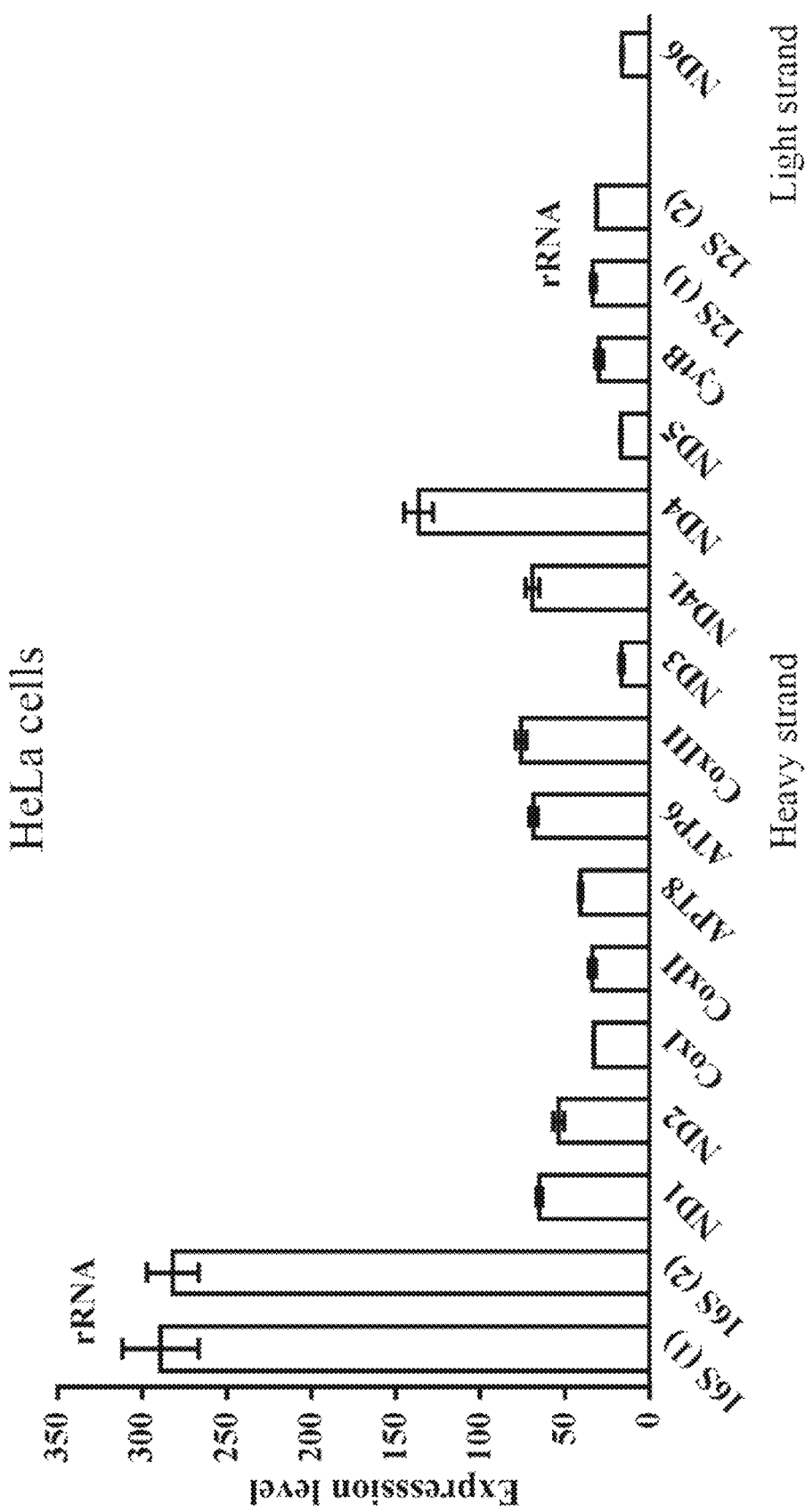
Figure 14E:
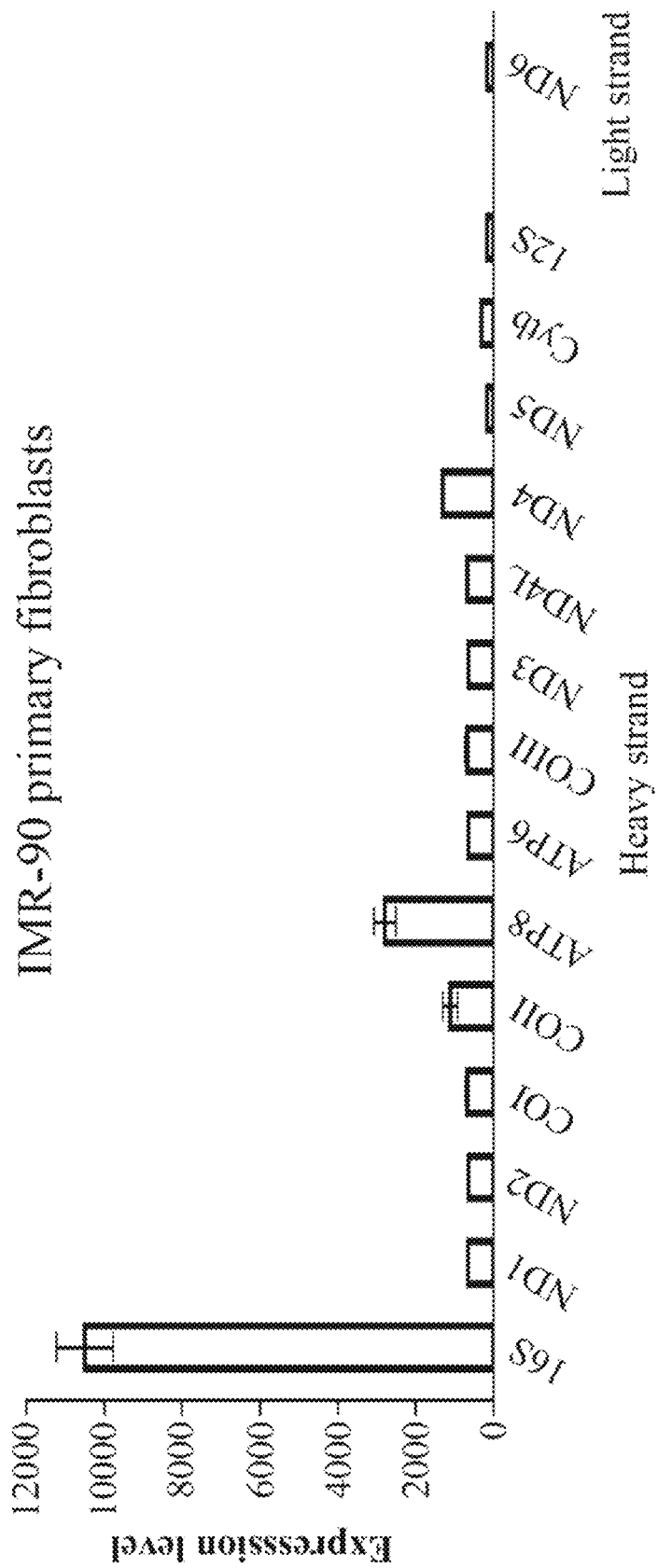

The robust activity of mitochondria in healthy cells was confirmed by high levels of mitochondrial transcripts (10 to 76-fold higher than in the cancer-derived cell line, see FIG. 14b), a result that is in agreement with the reduced mitochondrial activity in cancer cells (known as «Warburg effect»).

Thus, the co-labelling of mitochondria with mTRANS and mREP (never performed before) measured the efficiency of mitochondrial DNA processing in single cells.

The method of the invention could therefore be used as an indicator of reduced mitochondrial activity, characteristic of cancer cells.

Alterations in mtDNA Processing in Cells with Perturbed mtDNA Content

To assess whether mTRIP detects alterations of DNA processing in cells with mitochondrial perturbations the inventors examined HeLa rho⁰ cells where mtDNA is lacking (Parfait et al. 1998), and HeLa cells treated with ethidium bromide (EtBr) for three days to reduce their mtDNA content (King and Attardi 1996). Notably, HeLa rho0 cells contained about one third of the mitochondrial mass (TOM22 immunolabelling) compared to regular HeLa cells, but no signal was detected with either mTRANS or mREP, confirming the absence of mtDNA transcription and initiation of replication in these cells (FIG. 16 A). In contrast, cells treated with EtBr, which had a reduced mtDNA content, maintained a regular mitochondrial mass and displayed a 9.3-fold and a 5.9-fold increase in the levels of mREP and mTRANS, respectively, compared to untreated cells (FIG. 16 A). High levels of transcripts were confirmed by RT-qPCR of mitochondrial 16S rRNA and CytB. These data indicate that in spite of mtDNA depletion, EtBr-treated cells dramatically increased their mtDNA replication and transcription activities, likely to compensate for the low DNA content, in agreement with previous studies on transcription (Seidel-Rogol and Shadel 2002).

Finally, the inventors also examined cells depleted in mtDNA, as is the case for several diseases (Rotig and Poulton 2009), for example, Rrm2b fibroblasts, carrying a mutation that is associated with a mtDNA depletion syndrome (Bourdon et al. 2007).

Primary fibroblasts mutated in RRM2B were analyzed. The p53-inducible ribonucleotide reductase subunit which is essential for mtDNA synthesis and is associated with mtDNA depletion syndrome (Bourdon et al. 2007). The inventors found that Rrm2b fibroblasts in spite of a 44% reduction in the mitochondrial mass display a 4-fold reduction in mREP and a 3-fold reduction in mTRANS signals compared to normal fibroblasts (FIG. 15 B).

Here, reduced mtDNA transcription and replication were observed using mTRIP. In addition, we noted dramatically increased mitochondrial transcription and replication signals in cells with depleted mtDNA content following treatment with EtBr. This situation likely mimics the normal amounts of mitochondrial transcripts observed in cells with induced mtDNA depletion (Seidel-Rogol and Shadel 2002). Moreover, it is likely also representative of cells from patients with a particularly severe mtDNA depletion, which displayed steady-state levels of mt transcription and had a surprisingly slow progression of the disease compared to other mtDNA depletion syndromes (Barthelemy et al. 2001). Thus, mTRIP reveals qualitative and quantitative alterations, which provide additional tools for elucidating mitochondrial dysfunction in diseases.

Taken together, the analysis of three different cell types showed that mREP and mTRANS labelling identify altered or loss of mtDNA processing, which affects mitochondrial function, thus validating mTRIP for monitoring disease states both qualitatively and quantitatively.

Assays on samples of patients diagnosed with mitochondrial diseases have also been performed. Results are given in FIG. 17. Conclusions are that the reduction of the mitochondrial mass can be associated with either reduction or increase of mDNA processing activities. This proves the potential of the tool for its implementation in myopathies monitoring and/or diagnosis.

Figure 18A:
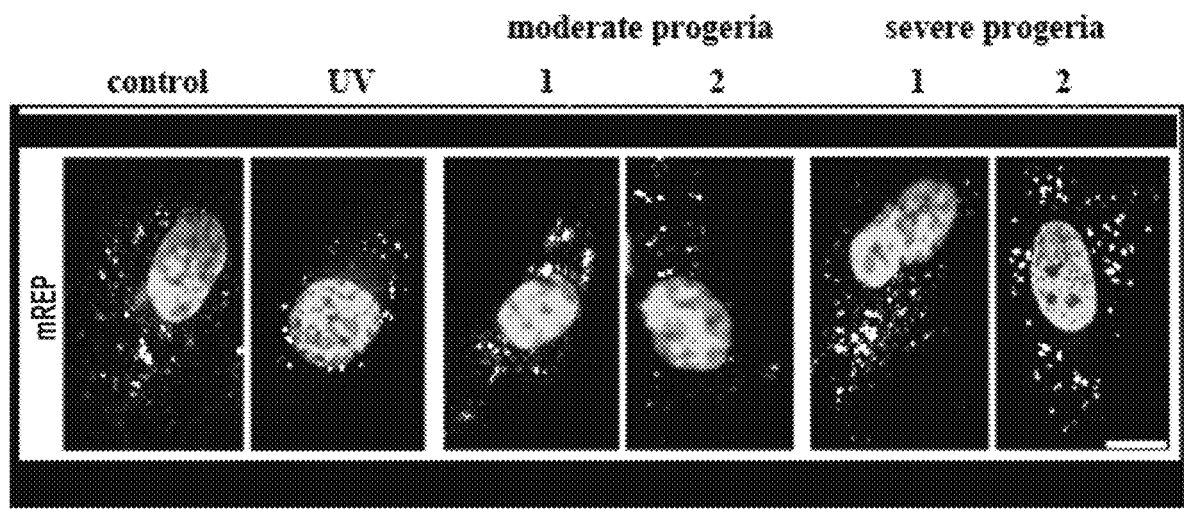
Figure 18B:
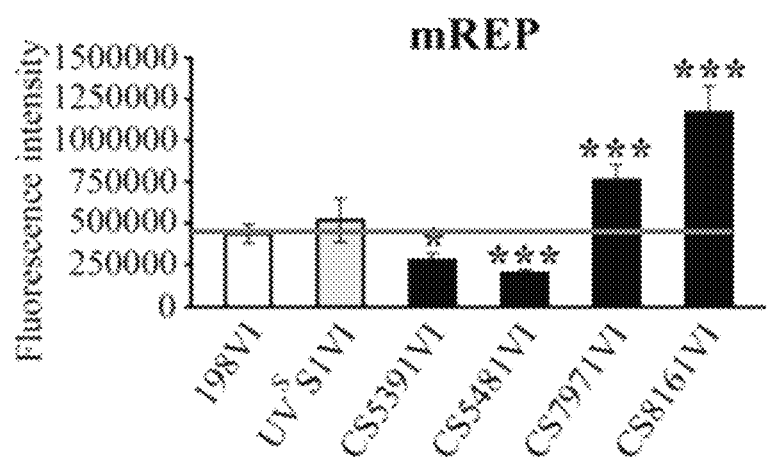
Figure 19A:
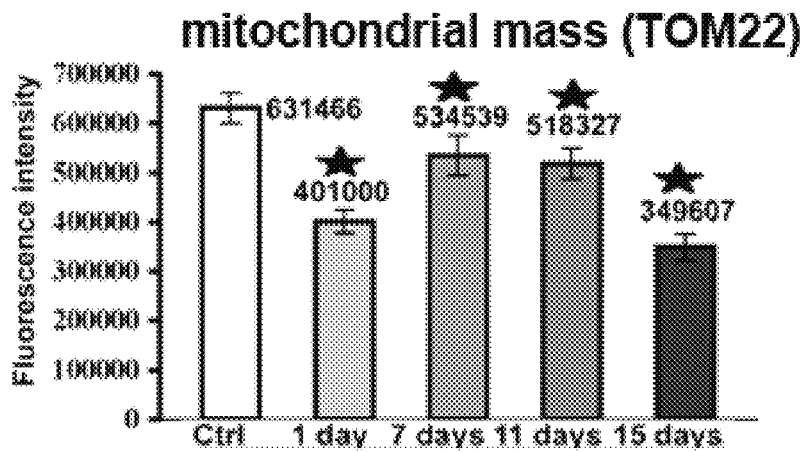
Figure 19B:
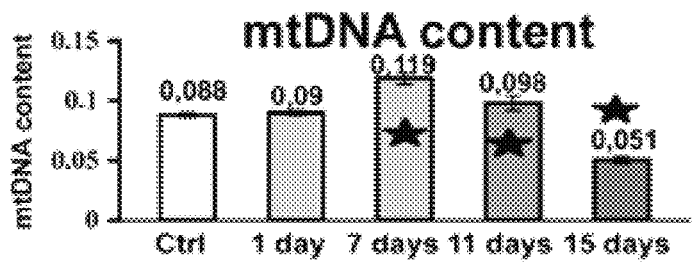
Figure 19C:
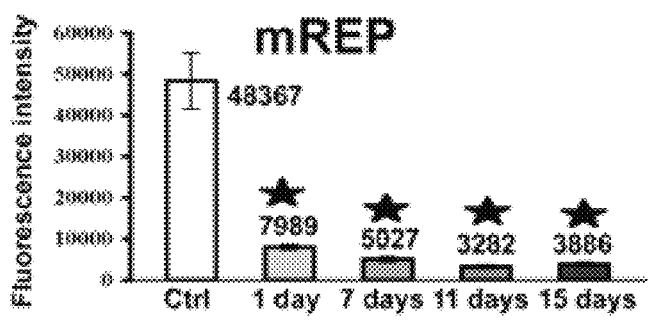
Figure 19D:
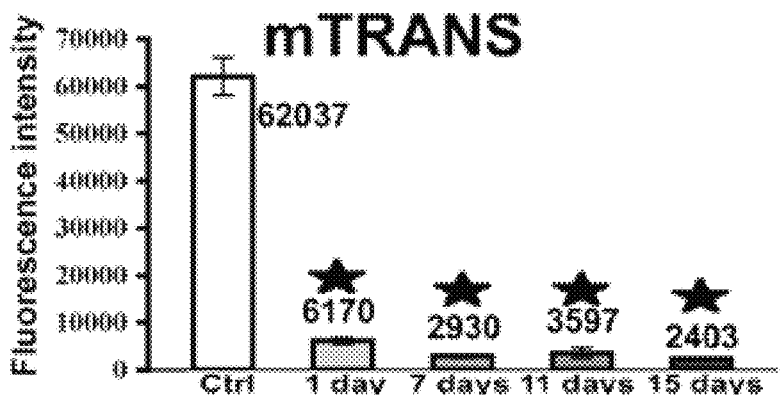

Assays on samples of patients diagnosed with diseases not yet known to be mitochondrial-related were also performed, with the aim to link the disease to mitochondrial function. Results are given in FIG. 18. Different mtDNA processing was observed in the "moderate" and "severe" forms of the Cokayne syndrome. As a consequence, mTRIP appears useful also for the detection of some diseases which display impaired mitochondrial function (including diseases not known for primary mitochondrial alterations).

The present invention is also of particular interest for testing the cytotoxicity of organic or chemical compounds, especially drugs.

Indeed, the present invention can be used in particular to assay tissues and organs whose cells are rich in mitochondria, as it is the case for cardiac and skeletal muscle, as well as liver. Therefore the induction of cytotoxicity by drugs or treatments affecting directly or indirectly these tissues/organs, can be identified and measured by checking mitochondrial DNA transcription and replication. Although lethal cytotoxicity can be evaluated with a number of available tests, the present invention provides for the detection and quantification of non-lethal and transitory cytotoxicity (the one which can have effect on the long term). To this end, the inventors have shown in HeLa cells that a mild cytotoxic agent (50 µM of $H_2O_2$—) known to reduce the mtDNA content[32] results in increase of mREP and mTRANS after a few hours of treatment, and that these events were associated with increase of the mitochondrial mass as well as of the transcription of a mitochondrial biogenesis factor (FIG. 12B). Since the inventors have used HeLa cells, which are not particularly rich in mitochondria as muscle and liver cells are, this experiment indicates that the invention enables the detection of cytotoxic effects in any type of cells. A more pronounced detection in mitochondria-rich cells is therefore expected.

$H_2O_2$ is considered as a low oxidative stress. To check whether mTRIP can be used to assess mitochondria dysfunction as a cytotoxicity test (preferential use for long term treatments and for products that progressively weaken cell function, i.e. anti-inflammatory drugs), the developed mTRIP protocol was also applied to the monitoring of HIV treatment by AZT. It was demonstrated that mTRIP anticipates the detection of mitochondrial alterations due to AZT treatment that are not visible at the level of the mitochondrial function and mitochondrial mass. Results are given in FIG. 19. Long term treatment with AZT is known to affect mitochondrial function, in particular in the muscle. With mTRIP, the inventors found that AZT greatly affects mtDNA processing in time, in spite of relatively normal values of mtDNA content and mt mass. This experiment proves the usefulness of the invention for use in in vitro detection of progressive myopathies associated with antiviral (AZT) HIV treatment. Possibly before the clinical appearance of the myopathy.

Similarly, affected mtDNA processing was demonstrated in cells treated with rifampicin (clinical antibiotic). We consider this treatment also as a cytotoxic stress. Results are given in FIG. 20.

These experiments are validating the fact that the invention enables the detection of mitochondrial impairments due to the use of drugs.

The invention thus also concerns a method for detection of altered mitochondrial activity in cells comprising the step of detecting the level of mitochondrial initation of DNA replication with a first probe of the invention and detecting the level of mitochondrial transcripts with a second probe of the invention.

The method may be used to detect at the level of single cells especially, cells having impaired activity such as cancer cells.

Accordingly, assays on samples of patients diagnosed with cancers were also performed. Results are given in FIG. 21. Detection of the labelling in specific normal and cancer cells (blood cancer cells and smears of solid cancer cells) was performed, allowing to conclude to different levels of mtDNA processing in cancer vs normal cells. These experiments have also allowed concluding to mitochondrial-dependent ATP production in cancer cell lines vs normal cells, demonstrating the usefulness of the developed tool for this purpose.

BIBLIOGRAPHY

1. Ojala, D., Montoya, J. & Attardi, G. *Nature* 290, 470-474 (1981).
2. Chang, D. D. & Clayton, D. A. *Proc Natl Acad Sci USA* 82, 351-355 (1985).
3. Clayton, D. A. *AnnuRev Cell Biol* 7, 453-478 (1991).
4. Holt, I. J., Lorimer, H. E. & Jacobs, H. T. *Cell* 100, 515-524 (2000).
5. Falkenberg, M., Larsson, N. G. & Gustafsson, C. M. *Annu Rev Biochem* 76, 679-699 (2007).
6. Scarpulla, R. C. *Physiol Rev* 88, 611-638 (2008).
7. Alan, L., Zelenka, J., Jezek, J., Dlaskova, A. & Jezek, P. *Acta Biochim Pol*. (2010) in press
8. Masny, P. S. et al. *Eur J Hum Genet* 18, 448-456 (2010)
9. Arabi, A. et al. *Nat Cell Biol* 7, 303-310 (2005).
10. de Planell-Saguer, M., Rodicio, M. C. & Mourelatos, Z. *Nat Protoc* 5, 1061-1073 (2010)
11. Gelfand, R. & Attardi, G. *Mol Cell Biol* 1, 497-511 (1981).
12. Montoya, J., Gaines, G. L. & Attardi, G. *Cell* 34, 151-159 (1983).
13. Brown, T. A., Cecconi, C., Tkachuk, A. N., Bustamante, C&Clayton, D. A. *Genes Dev* 19, 2466-2476 (2005).
14. Poulton, J. et al. *Hum Mol Genet* 3, 1763-1769 (1994).
15. Lee, C. F., Liu, C. Y., Hsieh, R. H. & Wei, Y. H. *Ann N Y Acad Sci* 1042, 246-254 (2005).
16. Korhonen, J. A., Pham, X. H., Pellegrini, M. & Falkenberg, M. *EMBO J* 23, 2423-2429 (2004).
17. Holt, I. J. *Trends Genet* 26, 103-109.
18. Arnaudo, E. et al *Lancet* 337, 508-510 (1991).
19. Parfait, B., Rustin, P., Munnich, A. & Rotig, A. *Biochem Biophys Res Commun* 247, 57-59 (1998).
20. Li, Z., Okamoto, K., Hayashi, Y. & Sheng, M. *Cell* 119, 873-887 (2004).
21. Fernandez-Vizarra, E., Enriquez, J. A., Perez-Martos, A., Montoya, J. & Fernandez-Silva, P. *Curr Genet* 54, 13-22 (2008).
22. Welle, S., Bhatt, K. & Thornton, C. A. *Genome Res* 9, 506-513 (1999).
23. Park, M. K., Ashby, M. C., Erdemli, G., Petersen, O. H. & Tepikin, A. V. *EMBO J* 20, 1863-1874 (2001).
24. Bonda, D. J., Wang, X., Perry, G., Smith, M. A. & Zhu, X. *Drugs Aging* 27, 181-192.
25. Wu, Y. T., Wu, S. B., Lee, W. Y. & Wei, Y. H. *Ann NY Acad Sci* 1201, 147-156.
26. Mitra, K., Wunder, C., Roysam, B., Lin, G. & Lippincott-Schwartz, J. *Proc Natl Acad Sci USA* 106, 11960-11965 (2009).
27. Moralli, D. & Monaco, Z. L. *PLoS One* 4, e4483 (2009).
28. Bolte, S. & Cordelieres, F. P. *J Microsc* 224, 213-232 (2006).
29. Schmittgen, T. D. & Livak, K. J. *Nat Protoc* 3, 1101-1108 (2008).
30. Ozawa, T., Natori, Y., Sato, M. & Umezawa, Y. *Nat Methods* 4, 413-419 (2007)
31. Sbisa, E et al. *Gene* 205(1-2), 125-140 (1997).
32. Lee, C. F., Liu, C. Y., Hsieh, R. H. & Wei, Y. H. *Ann NY Acad Sci* 1042, 246-254 (2005)
33. van Raamsdonk, C. D. & Tilghman, S. M. *Nucleic Acids Res* 29, E42-42 (2001).
34. Batzer, M. A. & Deininger, P. L. *Nat Rev Genet* 3, 370-379 (2002).
35. Gelfand, R. & Attardi, G. *Mol Cell Bbl* 1, 497-511 (1981).
36. Montoya, J., Gaines, G. L. & Attardi, G. *Cell* 34, 151-159 (1983).
37. Piechota, J. et al. *Acta Biochim Pol* 53, 157-168 (2006).
38. Lee, C. F., Liu, C. Y., Hsieh, R. H. & Wei, Y. H. *Ann NY Acad Sci* 1042, 246-254 (2005).
39. Korhonen, J. A., Pham, X. H., Pellegrini, M. & Falkenberg, M. *EMBO J* 23, 2423-2429 (2004).

Alam, T. I., T. Kanki, T. Muta, K. Ukaji, Y. Abe, H. Nakayama, K. Takio, N. Hamasaki, and D. Kang. 2003. Human mitochondrial DNA is packaged with TFAM. *Nucleic Acids Res.* 31:1640-5.

Antes, A., I. Tappin, S. Chung, R. Lim, B. Lu, A. M. Parrott, H. Z. Hill, C. K. Suzuki, and C. G. Lee. 2010. Differential regulation of full-length genome and a single-stranded 7S DNA along the cell cycle in human mitochondria. *Nucleic Acids Res.* 38:6466-76.

Barthelemy, C., H. Ogier de Baulny, J. Diaz, M. A. Cheval, P. Frachon, N. Romero, F. Goutieres, M. Fardeau, and A. Lombes. 2001. Late-onset mitochondrial DNA depletion: DNA copy number, multiple deletions, and compensation. *Ann Neurol.* 49:607-17.

Bellot, G., P. F. Cartron, E. Er, L. Oliver, P. Juin, L. C. Armstrong, P. Bornstein, K. Mihara, S. Manon, and F. M. Vallette. 2007. TOM22, a core component of the mitochondria outer membrane protein translocation pore, is a mitochondrial receptor for the proapoptotic protein Bax. *Cell Death Differ.* 14:785-94.

Bjursell, G., and P. Reichard. 1973. Effects of thymidine on deoxyribonucleoside triphosphate pools and deoxyribonucleic acid synthesis in Chinese hamster ovary cells. *J Biol Chem.* 248:3904-9.

Bogenhagen, D., and D. A. Clayton. 1977. Mouse L cell mitochondrial DNA molecules are selected randomly for replication throughout the cell cycle. *Cell.* 11:719-27.

Bonawitz, N. D., D. A. Clayton, and G. S. Shadel. 2006. Initiation and beyond:

multiple functions of the human mitochondrial transcription machinery. *Mol Cell.* 24:813-25.

Bourdon, A., L. Minai, V. Serre, J. P. Jais, E. Sarzi, S. Aubert, D. Chretien, P. de Lonlay, V. Paquis-Flucklinger, H. Arakawa, Y. Nakamura, A. Munnich, and A. Rotig. 2007. Mutation of RRM2B, encoding p53-controlled ribonucleotide reductase (p53R2), causes severe mitochondrial DNA depletion. *Nat Genet.* 39:776-80.

Brown, T. A., C. Cecconi, A. N. Tkachuk, C. Bustamante, and D. A. Clayton. 2005. Replication of mitochondrial DNA occurs by strand displacement with alternative light-strand origins, not via a strand-coupled mechanism. *Genes Dev.* 19:2466-76.

Brown, T. A., Tkachuk, A. N., and Clayton, D. A. 2008. Native R-loops persist throughout the mouse mitochondrial DNA genome. *J Biol Chem* 283(52): 36743-36751.

Chan, D. C. 2006. Mitochondrial fusion and fission in mammals. *Annu Rev Cell Dev Biol.* 22:79-99.

Chang, D. D. and Clayton, D. A. 1985. Priming of human mitochondrial DNA replication occurs at the light-strand promoter. *Proc Natl Acad Sci USA* 82(2): 351-355.

Chen, X. J., and R. A. Butow. 2005. The organization and inheritance of the mitochondrial genome. *Nat Rev Genet.* 6:815-25.

Clayton, D. A. 1991. Replication and transcription of vertebrate mitochondrial DNA. *Annu Rev Cell Biol* 7: 453-478.

Davis, A. F., and D. A. Clayton. 1996. In situ localization of mitochondrial DNA replication in intact mammalian cells. *J Cell Biol.* 135:883-93.

Falkenberg, M., Larsson, N. G., and Gustafsson, C. M. 2007. DNA replication and transcription in mammalian mitochondria. *Annu Rev Biochem* 76: 679-699.

Gonzalez-Vioque, E., J. Torres-Torronteras, A. L. Andreu, and R. Marti. 2011. Limited dCTP availability accounts for mitochondrial DNA depletion in mitochondrial neurogastrointestinal encephalomyopathy (MNGIE). *PLoS Genet.* 7:e1002035.

Harper, J. V. 2005. Synchronization of cell populations in G1/S and G2/M phases of the cell cycle. *Methods Mol Biol.* 296:157-66.

Karbowski, M., J. H. Spodnik, M. Teranishi, M. Wozniak, Y. Nishizawa, J. Usukura, and T. Wakabayashi. 2001. Opposite effects of microtubule-stabilizing and microtubule-destabilizing drugs on biogenesis of mitochondria in mammalian cells. *J Cell Sci.* 114:281-91.

King, M. P., and G. Attardi. 1996. Isolation of human cell lines lacking mitochondrial DNA. *Methods Enzymol.* 264: 304-13.

Lee, S., S. Kim, X. Sun, J. H. Lee, and H. Cho. 2007. Cell cycle-dependent mitochondrial biogenesis and dynamics in mammalian cells. *Biochem Biophys Res Commun.* 357:111-7.

Lee, S. H., H. Sterling, A. Burlingame, and F. McCormick. 2008. Tpr directly binds to Mad1 and Mad2 and is important for the Mad1-Mad2-mediated mitotic spindle checkpoint. *Genes Dev.* 22:2926-31.

Liu, X., S. Yan, T. Zhou, Y. Terada, and R. L. Erikson. 2004. The MAP kinase pathway is required for entry into mitosis and cell survival. *Oncogene.* 23:763-76.

Magnusson, J., M. Orth, P. Lestienne, and J. W. Taanman. 2003. Replication of mitochondrial DNA occurs throughout the mitochondria of cultured human cells. *Exp Cell Res.* 289:133-42.

Martinez-Diez, M., G. Santamaria, A. D. Ortega, and J. M. Cuezva. 2006. Biogenesis and dynamics of mitochondria during the cell cycle: significance of 3'UTRs. *PLoS One.* 1:e107.

Mitra, K., Wunder, C., Roysam, B., Lin, G., and Lippincott-Schwartz, J. 2009. A hyperfused mitochondrial state achieved at G1-S regulates cyclin E buildup and entry into S phase. *Proc Natl Acad Sci USA* 106(29): 11960-11965.

Ozawa, T., Natori, Y., Sato, M., and Umezawa, Y. 2007. Imaging dynamics of endogenous mitochondrial RNA in single living cells. *Nat Methods* 4(5): 413-419.

Pardee, A. B., and K. Keyomarsi. 1992. Modification of cell proliferation with inhibitors. *Curr Opin Cell Biol.* 4:186-91.

Parfait, B., Rustin, P., Munnich, A., and Rotig, A. 1998. Co-amplification of nuclear pseudogenes and assessment of heteroplasmy of mitochondrial DNA mutations. *Biochem Biophys Res Commun* 247(1): 57-59.

Parone, P. A., S. Da Cruz, D. Tondera, Y. Mattenberger, D. I. James, P. Maechler, F. Barja, and J. C. Martinou. 2008. Preventing mitochondrial fission impairs mitochondrial function and leads to loss of mitochondrial DNA. *PLoS One.* 3: e3257.

Pica-Mattoccia, L., and G. Attardi. 1972. Expression of the mitochondrial genome in HeLa cells. IX. Replication of mitochondrial DNA in relationship to cell cycle in HeLa cells. *J Mol Biol.* 64:465-84.

Poulton, J., Morten, K., Freeman-Emmerson, C., Potter, C., Sewry, C., Dubowitz, V., Kidd, H., Stephenson, J., Whitehouse, W., Hansen, F. J. et al. 1994. Deficiency of the human mitochondrial transcription factor h-mtTFA in infantile mitochondrial myopathy is associated with mtDNA depletion. *Hum Mol Genet* 3(10): 1763-1769.

Posakony, J. W., J. M. England, and G. Attardi. 1977. Mitochondrial growth and division during the cell cycle in HeLa cells. *J Cell Biol.* 74:468-91.

Rotig, A., and J. Poulton. 2009. Genetic causes of mitochondrial DNA depletion in humans. *Biochim Biophys Acta.* 1792:1103-8.

Scarpulla, R. C. 2008. Transcriptional paradigms in mammalian mitochondrial biogenesis and function. *Physiol Rev* 88(2): 611-638.

Seidel-Rogol, B. L., and G. S. Shadel. 2002. Modulation of mitochondrial transcription in response to mtDNA depletion and repletion in HeLa cells. *Nucleic Acids Res.* 30:1929-34.

Shutt, T. E., M. Bestwick, and G. S. Shadel. 2011. The core human mitochondrial transcription initiation complex: It only takes two to tango. *Transcription.* 2:55-59.

Shutt, T. E., M. F. Lodeiro, J. Cotney, C. E. Cameron, and G. S. Shadel. 2010. Core human mitochondrial transcription apparatus is a regulated two-component system in vitro. *Proc Natl Acad Sci USA.* 107:12133-8.

Spelbrink, J. N. 2010. Functional organization of mammalian mitochondrial DNA in nucleoids: history, recent developments, and future challenges. *IUBMB Life.* 62:19-32.

Urbani, L., S. W. Sherwood, and R. T. Schimke. 1995. Dissociation of nuclear and cytoplasmic cell cycle progression by drugs employed in cell synchronization. *Exp Cell Res.* 219:159-68.

Volpe, P., and T. Eremenko. 1973. Nuclear and cytoplasmic DNA synthesis during the mitotic cycle of HeLa cells. *Eur J Biochem.* 32:227-32.

von Wurmb-Schwark, N., L. Cavelier, and G. A. Cortopassi. 2006. A low dose of ethidium bromide leads to an increase of total mitochondrial DNA while higher concentrations induce the mtDNA 4997 deletion in a human neuronal cell line. *Mutat Res.* 596:57-63.

Xia, P., H. X. An, C. X. Dang, R. Radpour, C. Kohler, E. Fokas, R. Engenhart-Cabillic, W. Holzgreve, and X. Y. Zhong. 2009. Decreased mitochondrial DNA content in blood samples of patients with stage I breast cancer. *BMC Cancer.* 9:454.

Yano, M., N. Hoogenraad, K. Terada, and M. Mori. 2000. Identification and functional analysis of human Tom22 for protein import into mitochondria. *Mol Cell Biol.* 20:7205-13.

The invention claimed is:

1. A nucleic acid molecule that consists of the sequence of SEQ ID NO:1, wherein said nucleic acid molecule is directly labelled with a fluorescent group.

2. The nucleic acid molecule of claim 1, wherein the fluorescent group is fluorescein.

3. The nucleic acid molecule of claim 1, wherein the fluorescent group is Texas Red.

4. The nucleic acid molecule of claim 1, wherein the fluorescent group is rhodamine.

* * * * *

SEQUENCE LISTING

<160> NUMBER OF SEQ ID NOS: 68

<210> SEQ ID NO 1
<211> LENGTH: 99
<212> TYPE: DNA
<213> ORGANISM: Homo sapiens
<220> FEATURE:
<221> NAME/KEY: misc_feature
<222> LOCATION: (1)..(99)
<223> OTHER INFORMATION: Sequence name: mREP sequence (HSmREP or HS),
      coordinates 446-544 on the sequence of the human mitochondrial
      genome (accession number NC_012920.1, NCBI, GenBank or MITOMAP)
<220> FEATURE:
<221> NAME/KEY: misc_feature
<222> LOCATION: (1)..(99)
<223> OTHER INFORMATION: Polymorphism(s), e.g. nucleotide(s)
      substitution(s), may be observed on positions 2, 5, 8, 10-11,
      13-17, 19, 21, 23-24, 26, 30, 32, 35-37, 40, 42, 44-46, 48-50,
      52-54, 56-57, 62-63, 66-80, 82-83, 85, 88-90, 93, 96-97, 99

<400> SEQUENCE: 1
acattatttt cccctcccac tcccatacta ctaatctcat caatacaacc cccgcccatc    60
ctacccagca cacacacacc gctgctaacc ccataccc                           99

<210> SEQ ID NO 2
<211> LENGTH: 98
<212> TYPE: DNA
<213> ORGANISM: Pan troglodytes
<220> FEATURE:
<221> NAME/KEY: misc_feature
<222> LOCATION: (1)..(98)
<223> OTHER INFORMATION: Sequence name: Pt, coordinates 16424-16521 on
      the sequence Nc_001643.1 (NCBI or GenBank accession number)

<400> SEQUENCE: 2
acatgccctc cccctcaac tcccattcta ctagccccag caacgtaacc ccctactcac     60
cctactcaac acatataccg ctgctaaccc cataccct                           98

<210> SEQ ID NO 3
<211> LENGTH: 98
<212> TYPE: DNA
<213> ORGANISM: Pan paniscus
<220> FEATURE:
<221> NAME/KEY: misc_feature
<222> LOCATION: (1)..(98)
<223> OTHER INFORMATION: sequence name: Panp, coordinates 16433-16530 on
      the sequence NC_001644.1 (NCBI or GenBank accession number)

<400> SEQUENCE: 3
acatgtcctc cccctcaac tcccattcca ctagccccaa caacataacc ccctgcccac     60
cccactcagc acatataccg ctgctaaccc tataccct                           98

<210> SEQ ID NO 4
<211> LENGTH: 100
<212> TYPE: DNA
<213> ORGANISM: Gorilla gorilla
<220> FEATURE:
<221> NAME/KEY: misc_feature
<222> LOCATION: (1)..(100)
<223> OTHER INFORMATION: name: Grg, coordinates 16233-16332 on the
      sequence NC_001645.1 (NCBI or GenBank accession number)

<400> SEQUENCE: 4
gtatgcactt ttaacagtca ccccctcaact aacatagtca gcccaccagt acaaccccg    60 cccgccctag caacacacac tgctgctgat cctatacccc                         100

<210> SEQ ID NO 5
<211> LENGTH: 111
<212> TYPE: DNA
<213> ORGANISM: Pongo pygmaeus
<220> FEATURE:
<221> NAME/KEY: misc_feature
<222> LOCATION: (1)..(111)
<223> OTHER INFORMATION: sequence name: Pp, coordinates 16247-16357 on
      the sequence NC_001646.1 (NCBI or GenBank accession number)

<400> SEQUENCE: 5
atgtgcactt tcaacaggca cccctcaact aacacaaccc acttttaatt tccacctacc      60
aacccatcct gccctgcctt cccacaaaca ccactactac ccccacacct c             111

<210> SEQ ID NO 6
<211> LENGTH: 99
<212> TYPE: DNA
<213> ORGANISM: Hybolates lar
<220> FEATURE:
<221> NAME/KEY: misc_feature
<222> LOCATION: (1)..(99)
<223> OTHER INFORMATION: sequence name: Hl, coordinates 16148-16246 on
      the sequence NC_002082.1 (NCBI or GenBank accession number)

<400> SEQUENCE: 6
acattccata ttccagccga gcatccaatc cactaaaggt gctaattaat tcatgcttgt      60
tggacatagc aataaccaac caacgtaacc ccaaaccac                            99

<210> SEQ ID NO 7
<211> LENGTH: 99
<212> TYPE: DNA
<213> ORGANISM: Cebus albifrons
<220> FEATURE:
<221> NAME/KEY: misc_feature
<222> LOCATION: (1)..(99)
<223> OTHER INFORMATION: sequence name: Ca, coordinates 15946-16044 on
      the sequence NC_002763.1 (NCBI or GenBank accession number)

<400> SEQUENCE: 7
gcatttggtt cctacctcag ggccatctca ctaagaccgt gtccacgttc ctcttaaata      60
agacatcacg atggtgtggc gctatcaccc tcttaaccg                            99

<210> SEQ ID NO 8
<211> LENGTH: 112
<212> TYPE: DNA
<213> ORGANISM: Capra hircus
<220> FEATURE:
<221> NAME/KEY: misc_feature
<222> LOCATION: (1)..(112)
<223> OTHER INFORMATION: sequence name: Ch, coordinates 15519-15630 on
      the sequence NC_005044.2 (NCBI or Genbank accession number)

<400> SEQUENCE: 8
acacaaactt cccactccac aagcttacag acatgccaac aacccacacg tataaaaaca      60
tcccaatcct aacccaactt agatacccac acaaacgcca acaccacaca at            112

<210> SEQ ID NO 9
<211> LENGTH: 104
<212> TYPE: DNA
<213> ORGANISM: Mus musculus
<220> FEATURE:
<221> NAME/KEY: misc_feature
<222> LOCATION: (1)..(104)
<223> OTHER INFORMATION: sequence name: Mm, coordinates 15654-15757 on
      the sequence NC_005089.1 (NCBI or GenBank accession number)

<400> SEQUENCE: 9
atatgactat cccctteccc atttggtcta ttaatctacc atcctccgtg aaaccaacaa       60
cccgcccacc aatgccccte ttctcgctcc gggcccatta aact                       104

<210> SEQ ID NO 10
<211> LENGTH: 101
<212> TYPE: DNA
<213> ORGANISM: Oryctolagus cuniculus
<220> FEATURE:
<221> NAME/KEY: misc_feature
<222> LOCATION: (1)..(101)
<223> OTHER INFORMATION: sequence name: Oc, coordinates 15767-15867 on
      the sequence NC_001913.1 (NCBI or GenBank accession number)

<400> SEQUENCE: 10
agaccatcaa atctacacac accactcaac tcttacccat acgactatcc ctctccccca       60
gtcctctcac aacttaccat cctccgtgaa accaacaacc c                          101

<210> SEQ ID NO 11
<211> LENGTH: 100
<212> TYPE: DNA
<213> ORGANISM: Canis lupus
<220> FEATURE:
<221> NAME/KEY: misc_feature
<222> LOCATION: (1)..(100)
<223> OTHER INFORMATION: sequence name Cl, coordinates 16456-16555 ono
      the sequence NC_008092.1 (NCBI or GenBank accession number)

<400> SEQUENCE: 11
acttatacaa acccccctta cccccgtaa actcatgtca tctattatac acttatttat        60
gtcccgccaa accccaaaaa caggactaag tgcatacaat                            100

<210> SEQ ID NO 12
<211> LENGTH: 102
<212> TYPE: DNA
<213> ORGANISM: Rattus sordidus
<220> FEATURE:
<221> NAME/KEY: misc_feature
<222> LOCATION: (1)..(102)
<223> OTHER INFORMATION: Sequence name: Rs, coordinates 15643-15744 on
      the sequence NC_014871.1 (NCBI or GenBank accession number)

<400> SEQUENCE: 12
tcataaacct ttctcttcca tatgactatc cctgaccccca attggtctat atttctacca     60
tcctccgtga aatcaacaac ccgcccacta gtcccctct cc                          102

<210> SEQ ID NO 13
<211> LENGTH: 106
<212> TYPE: DNA
<213> ORGANISM: Felis catus
<220> FEATURE:
<221> NAME/KEY: misc_feature
<222> LOCATION: (1)..(106)
<223> OTHER INFORMATION: Sequence name: Fc, coordinates 759-864 on the
      sequence NC_001700.1 (NCBI or GenBank accession number)

<400> SEQUENCE: 13
atactaaatc ataactctgt tcgcagttat ctatagatat accgacctga ctctaattcg      60
tccctatcga acaacatttt acatgtctac gttagcccca catccc                     106

<210> SEQ ID NO 14
<211> LENGTH: 102
<212> TYPE: DNA

```
<213> ORGANISM: Castor canadensis
<220> FEATURE:
<221> NAME/KEY: misc_feature
<222> LOCATION: (1)..(102)
<223> OTHER INFORMATION: Sequence name Cc, coordinates 15766-15866 on
      the sequence NC_015108.1 (NCBI or GenBank accession number)

<400> SEQUENCE: 14
acagtctctt aatctaccat cctccgtgaa accagcaacc cgctcgggga atgtcccctc      60
ttctcgctcc gggcccatac aacttggggg tttctattct ga                       102

<210> SEQ ID NO 15
<211> LENGTH: 100
<212> TYPE: DNA
<213> ORGANISM: Gallus gallus
<220> FEATURE:
<221> NAME/KEY: misc_feature
<222> LOCATION: (1)..(100)
<223> OTHER INFORMATION: Sequence name: Gg, coordinates 473-571 on the
      sequence NC_001323.1 (NCBI or GenBank accession number)

<400> SEQUENCE: 15
ccattctttc ccctacacc cctcgccta cttgccttcc accgtacctc tggttcctcg       60
gtcaggcaca tcccatgcat aactcctgaa ctttctcact                          100

<210> SEQ ID NO 16
<211> LENGTH: 99
<212> TYPE: DNA
<213> ORGANISM: Danio rerio
<220> FEATURE:
<221> NAME/KEY: misc_feature
<222> LOCATION: (1)..(99)
<223> OTHER INFORMATION: Sequence name: Dr, coordinates 682-782 on the
      sequence NC_002333.2 (NCBI or GenBank accession number)

<400> SEQUENCE: 16
actatatatt attatctccc cctttggta tacgcgcgac aaaccccctt accccttac       60 gtccagcgat tcctgttatc cttgtcaaac ccctaaacc                            99

<210> SEQ ID NO 17
<211> LENGTH: 201
<212> TYPE: DNA
<213> ORGANISM: Homo sapiens
<220> FEATURE:
<221> NAME/KEY: misc_feature
<222> LOCATION: (1)..(201)
<223> OTHER INFORMATION: sequence of the PL-OH probe (position 225-425)
      according to the reference human mitochondrial sequence NC_012920,
      GenBank

<400> SEQUENCE: 17
gtaggacata ataataacaa ttgaatgtct gcacagccac tttccacaca gacatcataa     60 caaaaattt ccaccaaacc cccctcccc cgcttctggc cacagcactt aaacacatct     120
ctgccaaacc ccaaaaacaa agaaccctaa caccagccta accagatttc aaattttatc   180
ttttggcggt atgcactttt a                                             201

<210> SEQ ID NO 18
<211> LENGTH: 202
<212> TYPE: DNA
<213> ORGANISM: Homo sapiens
<220> FEATURE:
<221> NAME/KEY: misc_feature
<222> LOCATION: (1)..(202)
```

<223> OTHER INFORMATION: sequence of the 7S probe (position 16366-16566)
      according to the reference human mitochondrial sequence NC_012920,
      GenBank

<400> SEQUENCE: 18
catggatgac cccctcaga tagggtccc ttgaccacca tcctccgtga aatcaatatc        60
ccgcacaaga gtgctactct cctcgctccg ggcccataac acttgggggt agctaaagtg      120
aactgtatcc gacatctggt tcctacttca gggtcataaa gcctaaatag cccacacgtt     180
ccccttaaat aagacatcac ga                                              202

<210> SEQ ID NO 19
<211> LENGTH: 991
<212> TYPE: DNA
<213> ORGANISM: Homo sapiens
<220> FEATURE:
<221> NAME/KEY: misc_feature
<222> LOCATION: (1)..(991)
<223> OTHER INFORMATION: mt DNA fragment between coordinates 16024 and
      445 of the circular human mt gDNA: concatenation of fragment
      16024 -16568 and fragment 1-445 H strand numerotation), from
      Genbank sequence reference NC_012920.1
<220> FEATURE:
<221> NAME/KEY: misc_feature
<222> LOCATION: (546)..(546)
<223> OTHER INFORMATION: position 16568
<220> FEATURE:
<221> NAME/KEY: misc_feature
<222> LOCATION: (547)..(547)
<223> OTHER INFORMATION: position 1

<400> SEQUENCE: 19
ttctttcatg gggaagcaga tttgggtacc acccaagtat tgactcaccc atcaacaacc      60
gctatgtatt tcgtacatta ctgccagcca ccatgaatat tgtacggtac cataaatact    120
tgaccacctg tagtacataa aaacccaatc cacatcaaaa cccccctccc atgcttacaa    180
gcaagtacag caatcaaccc tcaactatca cacatcaact gcaactccaa agccaccccct   240 cacccactag gataccaaca aacctaccca cccttaacag tacatagtac ataaagccat    300
ttaccgtaca tagcacatta cagtcaaatc ccttctcgtc cccatggatg accccccctca   360 gatagggggtc ccttgaccac catcctccgt gaaatcaata tcccgcacaa gagtgctact   420
ctcctcgctc cgggcccata acacttgggg gtagctaaag tgaactgtat ccgacatctg    480
gttcctactt cagggtcata aagcctaaat agcccacacg ttccccttaa ataagacatc    540
acgatggatc acaggtctat caccctatta accactcacg ggagctctcc atgcatttgg    600
tattttcgtc tggggggtat gcacgcgata gcattgcgag acgctggagc cggagcaccc    660
tatgtcgcag tatctgtctt tgattcctgc ctcatcctat tatttatcgc acctacgttc    720
aatattacag gcgaacatac ttactaaagt gtgttaatta attaatgctt gtaggacata    780
ataataacaa ttgaatgtct gcacagccac tttccacaca gacatcataa caaaaatttt    840
ccaccaaacc cccctcccc cgcttctggc cacagcactt aaacacatct ctgccaaacc     900
ccaaaaacaa agaaccctaa caccagccta accagatttc aaattttatc ttttggcggt    960
atgcactttt aacagtcacc ccccaactaa c                                   991

<210> SEQ ID NO 20
<211> LENGTH: 20
<212> TYPE: DNA
<213> ORGANISM: Artificial Sequence
<220> FEATURE:
<223> OTHER INFORMATION: forward primer - probe TBP

```
<400> SEQUENCE: 20
ctcacaggtc aaaggtttac                                            20

<210> SEQ ID NO 21
<211> LENGTH: 20
<212> TYPE: DNA
<213> ORGANISM: Artificial Sequence
<220> FEATURE:
<223> OTHER INFORMATION: reverse primer - probe TBP

<400> SEQUENCE: 21
gctgaggttg caggaattga                                            20

<210> SEQ ID NO 22
<211> LENGTH: 20
<212> TYPE: DNA
<213> ORGANISM: Artificial Sequence
<220> FEATURE:
<223> OTHER INFORMATION: forward primer - probe 12S (1)

<400> SEQUENCE: 22
ctgctcgcca gaacactacg                                            20

<210> SEQ ID NO 23
<211> LENGTH: 20
<212> TYPE: DNA
<213> ORGANISM: Artificial Sequence
<220> FEATURE:
<223> OTHER INFORMATION: reverse primer - probe 12S (1)

<400> SEQUENCE: 23
tgagcaagag gtggtgaggt                                            20

<210> SEQ ID NO 24
<211> LENGTH: 20
<212> TYPE: DNA
<213> ORGANISM: Artificial Sequence
<220> FEATURE:
<223> OTHER INFORMATION: forward primer - probe 12S (2)

<400> SEQUENCE: 24
aaactgctcg ccagaacact                                            20

<210> SEQ ID NO 25
<211> LENGTH: 20
<212> TYPE: DNA
<213> ORGANISM: Artificial Sequence
<220> FEATURE:
<223> OTHER INFORMATION: reverse primer - probe 12S (2)

<400> SEQUENCE: 25
catgggctac accttgacct                                            20

<210> SEQ ID NO 26
<211> LENGTH: 20
<212> TYPE: DNA
<213> ORGANISM: Artificial Sequence
<220> FEATURE:
<223> OTHER INFORMATION: forward primer - probe 16S (1)

<400> SEQUENCE: 26
gtatgaatgg ctccacgagg                                            20

<210> SEQ ID NO 27
<211> LENGTH: 20
```

```
<212> TYPE: DNA
<213> ORGANISM: Artificial Sequence
<220> FEATURE:
<223> OTHER INFORMATION: reverse primer - probe 16S (1)

<400> SEQUENCE: 27
ggtcttctcg tcttgctgtg                                            20

<210> SEQ ID NO 28
<211> LENGTH: 20
<212> TYPE: DNA
<213> ORGANISM: Artificial Sequence
<220> FEATURE:
<223> OTHER INFORMATION: forward primer - probe 16S (2)

<400> SEQUENCE: 28
gctaaaccta gccccaaacc                                            20

<210> SEQ ID NO 29
<211> LENGTH: 20
<212> TYPE: DNA
<213> ORGANISM: Artificial Sequence
<220> FEATURE:
<223> OTHER INFORMATION: reverse primer - probe 16S (2)

<400> SEQUENCE: 29
ttggctctcc ttgcaaagtt                                            20

<210> SEQ ID NO 30
<211> LENGTH: 20
<212> TYPE: DNA
<213> ORGANISM: Artificial Sequence
<220> FEATURE:
<223> OTHER INFORMATION: forward primer - probe ND1

<400> SEQUENCE: 30
tggccaacct cctactcctc                                            20

<210> SEQ ID NO 31
<211> LENGTH: 20
<212> TYPE: DNA
<213> ORGANISM: Artificial Sequence
<220> FEATURE:
<223> OTHER INFORMATION: reverse primer - probe  ND1

<400> SEQUENCE: 31
atggcgtcag cgaagggttg                                            20

<210> SEQ ID NO 32
<211> LENGTH: 20
<212> TYPE: DNA
<213> ORGANISM: Artificial Sequence
<220> FEATURE:
<223> OTHER INFORMATION: forward primer - probe ND2

<400> SEQUENCE: 32
actgcgctaa gctcgcactg                                            20

<210> SEQ ID NO 33
<211> LENGTH: 20
<212> TYPE: DNA
<213> ORGANISM: Artificial Sequence
<220> FEATURE:
<223> OTHER INFORMATION: reverse primer - probe ND2
```

```
<400> SEQUENCE: 33
attatggatg cggttgcttg                                               20

<210> SEQ ID NO 34
<211> LENGTH: 20
<212> TYPE: DNA
<213> ORGANISM: Artificial Sequence
<220> FEATURE:
<223> OTHER INFORMATION: forward primer - probe COI

<400> SEQUENCE: 34
accctagacc aaacctacgc                                               20

<210> SEQ ID NO 35
<211> LENGTH: 20
<212> TYPE: DNA
<213> ORGANISM: Artificial Sequence
<220> FEATURE:
<223> OTHER INFORMATION: reverse primer - probe COI

<400> SEQUENCE: 35
taggccgaga aagtgttgtg                                               20

<210> SEQ ID NO 36
<211> LENGTH: 20
<212> TYPE: DNA
<213> ORGANISM: Artificial Sequence
<220> FEATURE:
<223> OTHER INFORMATION: forward primer - probe COII

<400> SEQUENCE: 36
acagatgcaa ttcccggacg                                               20

<210> SEQ ID NO 37
<211> LENGTH: 20
<212> TYPE: DNA
<213> ORGANISM: Artificial Sequence
<220> FEATURE:
<223> OTHER INFORMATION: reverse primer - probe COII

<400> SEQUENCE: 37
ggcatgaaac tgtggtttgc                                               20

<210> SEQ ID NO 38
<211> LENGTH: 18
<212> TYPE: DNA
<213> ORGANISM: Artificial Sequence
<220> FEATURE:
<223> OTHER INFORMATION: forward primer - probe ATP8

<400> SEQUENCE: 38
atgccccaac taaatact                                                 18

<210> SEQ ID NO 39
<211> LENGTH: 18
<212> TYPE: DNA
<213> ORGANISM: Artificial Sequence
<220> FEATURE:
<223> OTHER INFORMATION: reverse primer - probe ATP8

<400> SEQUENCE: 39
ttgtgggggc aatgaatg                                                 18

<210> SEQ ID NO 40
```

```
<211> LENGTH: 20
<212> TYPE: DNA
<213> ORGANISM: Artificial Sequence
<220> FEATURE:
<223> OTHER INFORMATION: forward primer - probe ATP6

<400> SEQUENCE: 40
cccacttctt accacaaggc                                                 20

<210> SEQ ID NO 41
<211> LENGTH: 20
<212> TYPE: DNA
<213> ORGANISM: Artificial Sequence
<220> FEATURE:
<223> OTHER INFORMATION: reverse primer - probe ATP6

<400> SEQUENCE: 41
gtaggtggcc tgcagtaatg                                                 20

<210> SEQ ID NO 42
<211> LENGTH: 20
<212> TYPE: DNA
<213> ORGANISM: Artificial Sequence
<220> FEATURE:
<223> OTHER INFORMATION: forward primer - probe COIII

<400> SEQUENCE: 42
acttccactc cataacgctc                                                 20

<210> SEQ ID NO 43
<211> LENGTH: 20
<212> TYPE: DNA
<213> ORGANISM: Artificial Sequence
<220> FEATURE:
<223> OTHER INFORMATION: reverse primer - probe COIII

<400> SEQUENCE: 43
tggccttggt atgtgctttc                                                 20

<210> SEQ ID NO 44
<211> LENGTH: 20
<212> TYPE: DNA
<213> ORGANISM: Artificial Sequence
<220> FEATURE:
<223> OTHER INFORMATION: forward primer - probe ND3

<400> SEQUENCE: 44
ctaccatgag ccctacaaac                                                 20

<210> SEQ ID NO 45
<211> LENGTH: 20
<212> TYPE: DNA
<213> ORGANISM: Artificial Sequence
<220> FEATURE:
<223> OTHER INFORMATION: reverse primer - probe ND3

<400> SEQUENCE: 45
actcataggc cagacttagg                                                 20

<210> SEQ ID NO 46
<211> LENGTH: 20
<212> TYPE: DNA
<213> ORGANISM: Artificial Sequence
<220> FEATURE:
<223> OTHER INFORMATION: forward primer - probe ND4L
```

```
<400> SEQUENCE: 46
tatcgctcac acctcatatc                                               20

<210> SEQ ID NO 47
<211> LENGTH: 20
<212> TYPE: DNA
<213> ORGANISM: Artificial Sequence
<220> FEATURE:
<223> OTHER INFORMATION: reverse primer - probe ND4L

<400> SEQUENCE: 47
aggcggcaaa gactagtatg                                               20

<210> SEQ ID NO 48
<211> LENGTH: 20
<212> TYPE: DNA
<213> ORGANISM: Artificial Sequence
<220> FEATURE:
<223> OTHER INFORMATION: forward primer - probe ND4

<400> SEQUENCE: 48
acaagctcca tctgcctacg                                               20

<210> SEQ ID NO 49
<211> LENGTH: 20
<212> TYPE: DNA
<213> ORGANISM: Artificial Sequence
<220> FEATURE:
<223> OTHER INFORMATION: reverse primer - probe ND4

<400> SEQUENCE: 49
ttatgagaat gactgcgccg                                               20

<210> SEQ ID NO 50
<211> LENGTH: 20
<212> TYPE: DNA
<213> ORGANISM: Artificial Sequence
<220> FEATURE:
<223> OTHER INFORMATION: forward primer - probe ND5

<400> SEQUENCE: 50
ggtttcatcc tcgccttagc                                               20

<210> SEQ ID NO 51
<211> LENGTH: 20
<212> TYPE: DNA
<213> ORGANISM: Artificial Sequence
<220> FEATURE:
<223> OTHER INFORMATION: reverse primer - probe ND5

<400> SEQUENCE: 51
acctaattgg gctgatttgc                                               20

<210> SEQ ID NO 52
<211> LENGTH: 20
<212> TYPE: DNA
<213> ORGANISM: Artificial Sequence
<220> FEATURE:
<223> OTHER INFORMATION: forward primer - probe CYTB

<400> SEQUENCE: 52
ctcccgtgag gccaaatatc                                               20

<210> SEQ ID NO 53
```

```
<211> LENGTH: 20
<212> TYPE: DNA
<213> ORGANISM: Artificial Sequence
<220> FEATURE:
<223> OTHER INFORMATION: reverse primer - probe CYTB

<400> SEQUENCE: 53
gaatcgtgtg agggtgggac                                              20

<210> SEQ ID NO 54
<211> LENGTH: 20
<212> TYPE: DNA
<213> ORGANISM: Artificial Sequence
<220> FEATURE:
<223> OTHER INFORMATION: forward primer - probe ND6

<400> SEQUENCE: 54
attggtgctg tgggtgaaag                                              20

<210> SEQ ID NO 55
<211> LENGTH: 20
<212> TYPE: DNA
<213> ORGANISM: Artificial Sequence
<220> FEATURE:
<223> OTHER INFORMATION: reverse primer - probe ND6

<400> SEQUENCE: 55
ggatcctccc gaatcaaccc                                              20

<210> SEQ ID NO 56
<211> LENGTH: 20
<212> TYPE: DNA
<213> ORGANISM: Artificial Sequence
<220> FEATURE:
<223> OTHER INFORMATION: forward primer - probe NRF1

<400> SEQUENCE: 56
ggagtgatgt ccgcacagaa                                              20

<210> SEQ ID NO 57
<211> LENGTH: 20
<212> TYPE: DNA
<213> ORGANISM: Artificial Sequence
<220> FEATURE:
<223> OTHER INFORMATION: reverse primer - probe NRF1

<400> SEQUENCE: 57
cgctgttaag cgccatagtg                                              20

<210> SEQ ID NO 58
<211> LENGTH: 20
<212> TYPE: DNA
<213> ORGANISM: Artificial Sequence
<220> FEATURE:
<223> OTHER INFORMATION: forward primer - probe POLG

<400> SEQUENCE: 58
gagaaggccc agcagatgta                                              20

<210> SEQ ID NO 59
<211> LENGTH: 18
<212> TYPE: DNA
<213> ORGANISM: Artificial Sequence
<220> FEATURE:
<223> OTHER INFORMATION: reverse primer - probe POLG
```

```
<400> SEQUENCE: 59
atccgacagc cgatacca                                                    18

<210> SEQ ID NO 60
<211> LENGTH: 20
<212> TYPE: DNA
<213> ORGANISM: Artificial Sequence
<220> FEATURE:
<223> OTHER INFORMATION: forward primer - probe TFAM

<400> SEQUENCE: 60
gacttctgcc agcataatac                                                  20

<210> SEQ ID NO 61
<211> LENGTH: 19
<212> TYPE: DNA
<213> ORGANISM: Artificial Sequence
<220> FEATURE:
<223> OTHER INFORMATION: reverse primer - probe TFAM

<400> SEQUENCE: 61
gagttctgcc tgctttatg                                                   19

<210> SEQ ID NO 62
<211> LENGTH: 20
<212> TYPE: DNA
<213> ORGANISM: Artificial Sequence
<220> FEATURE:
<223> OTHER INFORMATION: forward primer - probe 18S

<400> SEQUENCE: 62
gagaaacggc taccacatcc                                                  20

<210> SEQ ID NO 63
<211> LENGTH: 20
<212> TYPE: DNA
<213> ORGANISM: Artificial Sequence
<220> FEATURE:
<223> OTHER INFORMATION: reverse primer - probe 18S

<400> SEQUENCE: 63
gcctcgaaag agtcctgtat                                                  20

<210> SEQ ID NO 64
<211> LENGTH: 20
<212> TYPE: DNA
<213> ORGANISM: Artificial Sequence
<220> FEATURE:
<223> OTHER INFORMATION: forward primer - probe 12S

<400> SEQUENCE: 64
gctcgccaga acactacgag                                                  20

<210> SEQ ID NO 65
<211> LENGTH: 20
<212> TYPE: DNA
<213> ORGANISM: Artificial Sequence
<220> FEATURE:
<223> OTHER INFORMATION: reverse primer  - probe 12S

<400> SEQUENCE: 65
cagggtttgc tgaagatggc                                                  20

<210> SEQ ID NO 66
```

```
<211> LENGTH: 20
<212> TYPE: DNA
<213> ORGANISM: Artificial Sequence
<220> FEATURE:
<223> OTHER INFORMATION: forward primer - probe A

<400> SEQUENCE: 66
gtggctttgg agttgcagtt                                               20

<210> SEQ ID NO 67
<211> LENGTH: 21
<212> TYPE: DNA
<213> ORGANISM: Artificial Sequence
<220> FEATURE:
<223> OTHER INFORMATION: reverse primer - probe B1

<400> SEQUENCE: 67
cagccaccat gaatattgta c                                             21

<210> SEQ ID NO 68
<211> LENGTH: 20
<212> TYPE: DNA
<213> ORGANISM: Artificial Sequence
<220> FEATURE:
<223> OTHER INFORMATION: reverse primer - probe B2

<400> SEQUENCE: 68
gaagcagatt tgggtaccac                                               20
```